US009108340B2

(12) United States Patent
Yang et al.

(10) Patent No.: US 9,108,340 B2
(45) **Date of Patent: *Aug. 18, 2015**

(54) PROCESS FOR MANUFACTURING A RESULTING MULTI-LAYER PHARMACEUTICAL FILM

(71) Applicant: MonoSol Rx, LLC, Warren, NJ (US)

(72) Inventors: Robert K. Yang, Henderson, NV (US); Richard C. Fuisz, Beverly Hills, CA (US); Garry L. Myers, Kingsport, TN (US); Joseph M. Fuisz, Surfside, FL (US)

(73) Assignee: MonoSol Rx, LLC, Warren, NJ (US)

( * ) Notice: Subject to any disclaimer, the term of this patent is extended or adjusted under 35 U.S.C. 154(b) by 241 days.

This patent is subject to a terminal disclaimer.

(21) Appl. No.: 13/974,413

(22) Filed: Aug. 23, 2013

(65) Prior Publication Data

US 2014/0008832 A1 Jan. 9, 2014

Related U.S. Application Data

(63) Continuation of application No. 13/853,276, filed on Mar. 29, 2013, which is a continuation of application No. 13/035,328, filed on Feb. 25, 2011, now abandoned, which is a continuation of application No.

(Continued)

(51) Int. Cl.

*B29C 39/14* (2006.01)
*B29C 39/00* (2006.01)
*A61K 9/00* (2006.01)

(Continued)

(52) U.S. Cl.

CPC ............... *B29C 39/003* (2013.01); *A61K 9/006* (2013.01); *A61K 9/7007* (2013.01); *B29C 39/14* (2013.01); *B29C 71/02* (2013.01)

(58) Field of Classification Search

None

See application file for complete search history.

(56) References Cited

U.S. PATENT DOCUMENTS

| | | | |
|---|---|---|---|
| 26,401 | A | 12/1859 | Brashear et al. |
| 307,537 | A | 11/1884 | Foulks |
| 476,085 | A | 5/1892 | Smith |

(Continued)

FOREIGN PATENT DOCUMENTS

| | | | |
|---|---|---|---|
| AU | 741362 | B2 | 11/2001 |
| CA | 2274910 | C | 7/2005 |

(Continued)

OTHER PUBLICATIONS

Al-Ghananeem et al., "Effect of pH on Sublingual Absorption of Oxycodone Hydrochloride", AAPS PharmSciTech; Article 23, 7(1) (2006) (http://www.aapspharmscitec.org).

(Continued)

*Primary Examiner* — Edmund Lee
(74) *Attorney, Agent, or Firm* — Hoffmann & Baron, LLP

(57) ABSTRACT

The invention relates to the film products and methods of their preparation that demonstrate a non-self-aggregating uniform heterogeneity. Desirably, the films disintegrate in water and may be formed by a controlled drying process, or other process that maintains the required uniformity of the film. The films contain a polymer component, which includes polyethylene oxide optionally blended with hydrophilic cellulosic polymers. Desirably, the films also contain a pharmaceutical and/or cosmetic active agent with no more than a 10% variance of the active agent pharmaceutical and/or cosmetic active agent per unit area of the film.

30 Claims, 34 Drawing Sheets

Related U.S. Application Data

12/614,928, filed on Nov. 9, 2009, now Pat. No. 7,897,080, which is a continuation of application No. 10/856,176, filed on May 28, 2004, now Pat. No. 7,666,337, which is a continuation-in-part of application No. 10/768,809, filed on Jan. 30, 2004, now Pat. No. 7,357,891, which is a continuation-in-part of application No. PCT/US02/32575, filed on Oct. 11, 2002, which is a continuation of application No. 10/074,272, filed on Feb. 14, 2002, now Pat. No. 7,425,292, said application No. 10/768,809 is a continuation-in-part of application No. PCT/US02/32594, filed on Oct. 11, 2002, which is a continuation of application No. 10/074,272, filed on Feb. 14, 2002, now Pat. No. 7,425,292, said application No. 10/768,809 is a continuation-in-part of application No. PCT/US02/32542, filed on Oct. 11, 2002, which is a continuation of application No. 10/074,272, filed on Feb. 14, 2002, now Pat. No. 7,425,292.

(60) Provisional application No. 60/473,902, filed on May 28, 2003, provisional application No. 60/371,940, filed on Apr. 11, 2002, provisional application No. 60/443,741, filed on Jan. 30, 2003, provisional application No. 60/328,868, filed on Oct. 12, 2001, provisional application No. 60/386,937, filed on Jun. 7, 2002, provisional application No. 60/414,276, filed on Sep. 27, 2002.

(51) Int. Cl.
*A61K 9/70* (2006.01)
*B29C 71/02* (2006.01)

(56) References Cited

U.S. PATENT DOCUMENTS

| | | | |
|---|---|---|---|
| 492,417 | A | 2/1893 | McAlister |
| 503,070 | A | 8/1893 | Broadwell et al. |
| 596,302 | A | 12/1897 | McMahon |
| 688,446 | A | 10/1901 | Stempel, Jr. |
| 1,110,546 | A | 9/1914 | Hewitt |
| 1,827,354 | A | 10/1931 | Cooper |
| 2,142,537 | A | 1/1939 | Tiaxa |
| 2,277,038 | A | 3/1942 | Curtis |
| 2,352,691 | A | 7/1944 | Curtis |
| 2,376,656 | A | 5/1945 | Leonia |
| 2,501,544 | A | 3/1950 | Shrontz |
| 2,612,165 | A | 9/1952 | Szukerski |
| 2,980,554 | A | 4/1961 | Gentile et al. |
| 3,007,848 | A | 11/1961 | Stroop |
| 3,044,338 | A | 7/1962 | Horton et al. |
| 3,131,068 | A | 4/1964 | Grief |
| 3,142,217 | A | 7/1964 | Busse |
| 3,189,174 | A | 6/1965 | Cormack |
| 3,237,596 | A | 3/1966 | Grass, Jr. et al. |
| 3,242,959 | A | 3/1966 | Glass |
| 3,249,109 | A | 5/1966 | Maeth et al. |
| 3,324,754 | A | 6/1967 | Peavy |
| 3,370,497 | A | 2/1968 | Busse |
| 3,419,137 | A | 12/1968 | Walck, III |
| 3,444,858 | A | 5/1969 | Russell |
| 3,451,539 | A | 6/1969 | Wysocki |
| 3,536,809 | A | 10/1970 | Applezwig |
| 3,539,605 | A | 11/1970 | Oberhofer |
| 3,551,556 | A | 12/1970 | Kliment et al. |
| 3,598,122 | A | 8/1971 | Zaffaroni |
| 3,610,248 | A | 10/1971 | Davidson |
| 3,625,351 | A | 12/1971 | Eisenberg |
| 3,632,740 | A | 1/1972 | Robinson et al. |
| 3,640,741 | A | 2/1972 | Etes |
| 3,641,237 | A | 2/1972 | Gould et al. |
| 3,650,461 | A | 3/1972 | Hutcheson |
| 3,677,866 | A | 7/1972 | Pickett et al. |
| 3,731,683 | A | 5/1973 | Zaffaroni |
| 3,753,732 | A | 8/1973 | Boroshok |
| 3,755,558 | A | 8/1973 | Scribner |
| 3,768,725 | A | 10/1973 | Pilaro |
| 3,795,527 | A | 3/1974 | Stone et al. |
| 3,809,220 | A | 5/1974 | Arcudi |
| 3,814,095 | A | 6/1974 | Lubens |
| 3,825,014 | A | 7/1974 | Wroten |
| 3,835,995 | A | 9/1974 | Haines |
| 3,840,657 | A | 10/1974 | Norfleet |
| 3,892,905 | A | 7/1975 | Albert |
| 3,911,099 | A | 10/1975 | DeFoney et al. |
| 3,933,245 | A | 1/1976 | Mullen |
| 3,972,995 | A | 8/1976 | Tsuk et al. |
| 3,979,839 | A | 9/1976 | Blanie |
| 3,996,934 | A | 12/1976 | Zaffaroni |
| 3,998,215 | A | 12/1976 | Anderson et al. |
| 4,015,023 | A | 3/1977 | Lamberti et al. |
| 4,022,924 | A | 5/1977 | Mitchell et al. |
| 4,029,757 | A | 6/1977 | Mlodozeniec et al. |
| 4,029,758 | A | 6/1977 | Mlodozeniec et al. |
| 4,031,200 | A | 6/1977 | Reif |
| 4,049,848 | A | 9/1977 | Goodale et al. |
| 4,053,046 | A | 10/1977 | Roark |
| 4,067,116 | A | 1/1978 | Bryner et al. |
| 4,105,116 | A | 8/1978 | Jones et al. |
| 4,123,592 | A | 10/1978 | Rainer et al. |
| 4,126,503 | A | 11/1978 | Gardner |
| 4,128,445 | A | 12/1978 | Sturzenegger et al. |
| 4,136,145 | A | 1/1979 | Fuchs et al. |
| 4,136,162 | A | 1/1979 | Fuchs et al. |
| 4,139,627 | A | 2/1979 | Lane et al. |
| 4,202,966 | A | 5/1980 | Misaki et al. |
| 4,226,848 | A | 10/1980 | Nagai et al. |
| 4,251,400 | A | 2/1981 | Columbus |
| 4,251,561 | A | 2/1981 | Gajewski |
| 4,284,194 | A | 8/1981 | Flatau |
| 4,292,299 | A | 9/1981 | Suzuki et al. |
| 4,294,820 | A | 10/1981 | Keith et al. |
| 4,302,465 | A | 11/1981 | AF Ekenstam et al. |
| 4,307,075 | A | 12/1981 | Martin |
| 4,307,117 | A | 12/1981 | Leshik |
| 4,325,855 | A | 4/1982 | Dickmann et al. |
| 4,341,563 | A | 7/1982 | Kurihara et al. |
| 4,365,423 | A | 12/1982 | Arter et al. |
| 4,373,036 | A | 2/1983 | Chang et al. |
| 4,390,450 | A | 6/1983 | Gibson et al. |
| 4,406,708 | A | 9/1983 | Hesselgren |
| 4,432,975 | A | 2/1984 | Libby |
| 4,438,258 | A | 3/1984 | Graham |
| 4,451,260 | A | 5/1984 | Mitra |
| 4,460,532 | A | 7/1984 | Cornell |
| 4,460,562 | A | 7/1984 | Keith et al. |
| 4,466,973 | A | 8/1984 | Rennie |
| 4,478,658 | A | 10/1984 | Wittwer |
| 4,503,070 | A | 3/1985 | Eby, III |
| 4,511,592 | A | 4/1985 | Percel et al. |
| 4,515,162 | A | 5/1985 | Yamamoto et al. |
| 4,517,173 | A | 5/1985 | Kizawa et al. |
| 4,529,301 | A | 7/1985 | Rountree |
| 4,529,601 | A | 7/1985 | Broberg et al. |
| 4,529,748 | A | 7/1985 | Wienecke |
| 4,562,020 | A | 12/1985 | Hijiya et al. |
| 4,569,837 | A | 2/1986 | Suzuki et al. |
| 4,572,832 | A | 2/1986 | Kigasawa et al. |
| 4,582,835 | A | 4/1986 | Lewis et al. |
| 4,588,592 | A | 5/1986 | Elias |
| 4,593,053 | A | 6/1986 | Jevne et al. |
| 4,598,089 | A | 7/1986 | Hadvary et al. |
| 4,608,249 | A | 8/1986 | Otsuka et al. |
| 4,613,497 | A | 9/1986 | Chavkin |
| 4,615,697 | A | 10/1986 | Robinson |
| 4,619,701 | A | 10/1986 | Angrick et al. |
| 4,621,482 | A | 11/1986 | Crevasse et al. |
| 4,623,394 | A | 11/1986 | Nakamura et al. |
| 4,631,837 | A | 12/1986 | Magoon |
| 4,639,367 | A | 1/1987 | Mackles |

(56) References Cited

U.S. PATENT DOCUMENTS 4,648,509 A 3/1987 Alves
4,659,714 A 4/1987 Watt-Smith
4,661,359 A 4/1987 Seaborne et al.
4,675,009 A 6/1987 Hymes et al.
4,695,465 A 9/1987 Kigasawa et al.
4,704,119 A 11/1987 Shaw et al.
4,705,174 A 11/1987 Goglio
4,712,460 A 12/1987 Allen et al.
4,713,239 A 12/1987 Babaian et al.
4,713,243 A 12/1987 Schiraldi et al.
4,713,251 A 12/1987 Seighman
4,716,802 A 1/1988 O'Connor et al.
4,722,761 A 2/1988 Cartmell et al.
4,727,064 A 2/1988 Pitha
4,740,365 A 4/1988 Yukimatsu et al.
4,748,022 A 5/1988 Busciglio
4,752,465 A 6/1988 Mackles
4,762,230 A 8/1988 Croce
4,765,983 A 8/1988 Takayanagi et al.
4,772,470 A 9/1988 Inoue et al.
4,777,046 A 10/1988 Iwakura et al.
4,780,309 A 10/1988 Geria et al.
4,781,294 A 11/1988 Croce
4,787,517 A 11/1988 Martin
4,789,667 A 12/1988 Makino et al.
4,802,924 A 2/1989 Woznicki et al.
4,828,841 A 5/1989 Porter et al.
4,849,246 A 7/1989 Schmidt
4,851,394 A 7/1989 Kubodera
4,860,754 A 8/1989 Sharik et al.
4,861,632 A 8/1989 Caggiano
RE33,093 E 10/1989 Schiraldi et al.
4,872,270 A 10/1989 Fronheiser et al.
4,876,092 A 10/1989 Mizobuchi et al.
4,876,970 A 10/1989 Bolduc
4,880,416 A 11/1989 Horiuchi et al.
4,888,354 A 12/1989 Chang et al.
4,894,232 A 1/1990 Reul et al.
4,900,552 A 2/1990 Sanvordeker et al.
4,900,554 A 2/1990 Yangibashi et al.
4,900,556 A 2/1990 Wheatley et al.
4,910,247 A 3/1990 Haldar et al.
4,915,950 A 4/1990 Miranda et al.
4,925,670 A 5/1990 Schmidt
4,927,634 A 5/1990 Sorrentino et al.
4,927,636 A 5/1990 Hijiya et al.
4,929,447 A 5/1990 Yang
4,937,078 A 6/1990 Mezei et al.
4,940,587 A 7/1990 Jenkins et al.
4,948,580 A 8/1990 Browning
4,958,580 A 9/1990 Asaba et al.
4,978,531 A 12/1990 Yamazaki et al.
4,980,169 A 12/1990 Oppenheimer et al.
4,981,693 A 1/1991 Higashi et al.
4,981,875 A 1/1991 Leusner et al.
4,993,586 A 2/1991 Taulbee et al.
5,023,082 A 6/1991 Friedman et al.
5,023,271 A 6/1991 Vigne et al.
5,024,701 A 6/1991 Desmarais
5,025,692 A 6/1991 Reynolds
5,028,632 A 7/1991 Fuisz
5,044,241 A 9/1991 Labrecque
5,044,761 A 9/1991 Yuhki et al.
5,045,445 A 9/1991 Schultz
5,047,244 A 9/1991 Sanvordeker et al.
5,049,322 A 9/1991 Devissaguet et al.
5,056,584 A 10/1991 Seaton
5,064,717 A 11/1991 Suzuki et al.
5,072,842 A 12/1991 White
5,078,734 A 1/1992 Noble
5,089,307 A 2/1992 Ninomiya et al.
5,100,591 A 3/1992 Leclef et al.
5,107,734 A 4/1992 Armbruster
5,116,140 A 5/1992 Hirashima
5,118,508 A 6/1992 Kikuchi et al.
5,126,160 A 6/1992 Giddey et al.
5,137,729 A 8/1992 Kuroya et al.
5,158,825 A 10/1992 Altwirth
5,166,233 A 11/1992 Kuroya et al.
5,176,705 A 1/1993 Noble
5,184,771 A 2/1993 Jud et al.
5,186,938 A 2/1993 Sablotsky et al.
5,188,838 A 2/1993 Deleuil et al.
5,196,436 A 3/1993 Smith
5,229,164 A 7/1993 Pins et al.
5,230,441 A 7/1993 Kaufman et al.
5,234,957 A 8/1993 Mantelle
5,264,024 A 11/1993 Bosvot et al.
5,271,940 A 12/1993 Cleary et al.
5,272,191 A 12/1993 Ibrahim et al.
5,316,717 A 5/1994 Koepff et al.
5,325,968 A 7/1994 Sowden
5,328,942 A 7/1994 Akhtar et al.
5,344,676 A 9/1994 Kim et al.
5,346,701 A 9/1994 Heiber et al.
5,354,551 A 10/1994 Schmidt
5,360,629 A 11/1994 Milbourn et al.
5,369,131 A 11/1994 Poli et al.
5,375,930 A 12/1994 Tani
5,380,529 A 1/1995 Heusser et al.
5,393,528 A 2/1995 Staab
5,405,637 A 4/1995 Martinez et al.
5,407,278 A 4/1995 Beer
5,411,945 A 5/1995 Ozaki et al.
5,413,792 A 5/1995 Ninomiya et al.
5,422,127 A 6/1995 Dube et al.
5,423,423 A 6/1995 Sato et al.
5,433,960 A 7/1995 Meyers
5,451,419 A 9/1995 Schwab et al.
5,455,043 A 10/1995 Fischel-Ghodsian
5,458,884 A 10/1995 Britton et al.
5,462,749 A 10/1995 Rencher
5,472,704 A 12/1995 Santus et al.
5,479,408 A 12/1995 Will
5,489,436 A 2/1996 Hoy et al.
5,506,046 A 4/1996 Andersen et al.
5,518,902 A 5/1996 Ozaki et al.
5,529,782 A 6/1996 Staab
5,530,861 A 6/1996 Diamant et al.
5,550,178 A 8/1996 Desai et al.
5,551,033 A 8/1996 Foster et al.
5,560,538 A 10/1996 Sato et al.
5,567,431 A 10/1996 Vert et al.
5,573,783 A 11/1996 Desieno et al.
5,582,342 A 12/1996 Jud
5,587,175 A 12/1996 Viegas et al.
5,588,009 A 12/1996 Will
5,589,357 A 12/1996 Martinez et al.
5,593,697 A 1/1997 Barr et al.
5,601,605 A 2/1997 Crowe et al.
5,605,696 A 2/1997 Eury et al.
5,605,698 A 2/1997 Ueno
5,613,779 A 3/1997 Niwa
5,614,212 A 3/1997 D'Angelo et al.
5,620,757 A 4/1997 Ninomiya et al.
5,629,003 A 5/1997 Horstmann et al.
5,629,021 A 5/1997 Wright
5,633,006 A 5/1997 Catania et al.
5,641,093 A 6/1997 Dolin et al.
5,641,536 A 6/1997 Lech et al.
D380,836 S 7/1997 Fitzpatrick et al.
5,647,431 A 7/1997 Takeshita et al.
5,653,993 A 8/1997 Ghanta et al.
5,656,296 A 8/1997 Khan et al.
5,656,297 A 8/1997 Bernstein et al.
5,670,168 A 9/1997 Baichwal et al.
5,679,145 A 10/1997 Andersen et al.
5,681,873 A 10/1997 Norton et al.
5,689,550 A 11/1997 Garson et al.
5,698,181 A 12/1997 Luo
5,698,217 A 12/1997 Wilking
5,700,478 A 12/1997 Biegajski et al.
5,700,479 A 12/1997 Lundgren
5,725,648 A 3/1998 Brown et al.

(56) References Cited

U.S. PATENT DOCUMENTS 5,733,575 A 3/1998 Mehra et al.
5,738,211 A 4/1998 Ichino et al.
5,742,905 A 4/1998 Pepe et al.
5,750,145 A 5/1998 Patell
5,750,157 A 5/1998 Grosswald et al.
5,750,585 A 5/1998 Park et al.
5,759,599 A 6/1998 Wampler et al.
5,761,525 A 6/1998 Williams
5,764,639 A 6/1998 Staples et al.
5,764,899 A 6/1998 Eggleston et al.
5,765,004 A 6/1998 Foster et al.
5,766,332 A 6/1998 Graves et al.
5,766,525 A 6/1998 Andersen et al.
5,766,620 A 6/1998 Heiber et al.
5,766,839 A 6/1998 Johnson et al.
5,771,353 A 6/1998 Eggleston et al.
5,785,180 A 7/1998 Dressel et al.
5,792,494 A 8/1998 Kanca et al.
5,800,832 A 9/1998 Tapolsky et al.
5,806,284 A 9/1998 Gifford
5,815,398 A 9/1998 Dighe et al.
5,822,526 A 10/1998 Waskiewicz
5,830,437 A 11/1998 Ascione et al.
5,830,884 A 11/1998 Kasica et al.
5,846,557 A 12/1998 Eisenstadt et al.
5,847,023 A 12/1998 Viegas et al.
5,862,915 A 1/1999 Plezia et al.
5,864,684 A 1/1999 Nielsen
5,881,476 A 3/1999 Strobush et al.
5,891,461 A 4/1999 Jona et al.
5,891,845 A 4/1999 Myers
5,894,930 A 4/1999 Faughey et al.
5,900,247 A 5/1999 Rault et al.
5,906,742 A 5/1999 Wang et al.
5,937,161 A 8/1999 Mulligan et al.
5,941,393 A 8/1999 Wilfong, Jr.
5,945,651 A 8/1999 Chorosinski et al.
5,948,430 A 9/1999 Zerbe et al.
5,955,097 A 9/1999 Tapolsky et al.
5,965,154 A 10/1999 Haralambopoulos
5,980,554 A 11/1999 Lenker et al.
5,992,742 A 11/1999 Sullivan et al.
5,995,597 A 11/1999 Woltz et al.
6,004,996 A 12/1999 Shah et al.
6,024,975 A 2/2000 D'Angelo et al.
6,030,616 A 2/2000 Waters et al.
6,031,895 A 2/2000 Cohn et al.
6,036,016 A 3/2000 Arnold
6,047,484 A 4/2000 Bolland et al.
6,051,253 A 4/2000 Zettler et al.
6,054,119 A 4/2000 Hurme et al.
6,064,990 A 5/2000 Goldsmith
6,072,100 A 6/2000 Mooney et al.
6,074,097 A 6/2000 Hayashi et al.
6,077,558 A 6/2000 Euber
6,090,401 A 7/2000 Gowan, Jr. et al.
6,099,871 A 8/2000 Martinez
6,103,266 A 8/2000 Tapolsky et al.
6,106,930 A 8/2000 Ludwig
6,143,276 A 11/2000 Unger
6,148,708 A 11/2000 Pfeiffer
6,152,007 A 11/2000 Sato
6,153,210 A 11/2000 Roberts et al.
6,153,220 A 11/2000 Cumming et al.
6,159,498 A 12/2000 Tapolsky et al.
6,161,129 A 12/2000 Rochkind
6,177,066 B1 1/2001 Pataut et al.
6,177,092 B1 1/2001 Lentini et al.
6,177,096 B1 1/2001 Zerbe et al.
6,183,808 B1 2/2001 Grillo et al.
6,197,329 B1 3/2001 Hermelin et al.
6,203,566 B1 3/2001 Alanen et al.
6,219,694 B1 4/2001 Lazaridis et al.
6,227,359 B1 5/2001 Truluck
6,230,894 B1 5/2001 Danville
6,231,957 B1 5/2001 Zerbe et al.
6,238,700 B1 5/2001 Dohner et al.
6,264,981 B1 7/2001 Zhang et al.
6,267,808 B1 7/2001 Grillo et al.
6,268,048 B1 7/2001 Topolkaraev et al.
6,284,264 B1 9/2001 Zerbe et al.
6,287,595 B1 9/2001 Loewy et al.
6,294,206 B1 9/2001 Barrett-Reis et al.
6,311,627 B1 11/2001 Draper et al.
6,338,407 B2 1/2002 Danville
6,344,088 B1 2/2002 Kamikihara et al.
6,374,715 B1 4/2002 Takatsuka
6,375,963 B1 4/2002 Repka et al.
6,391,294 B1 5/2002 Dettmar et al.
6,394,306 B1 5/2002 Pawlo et al.
6,395,299 B1 5/2002 Babich et al.
6,413,792 B1 7/2002 Sauer et al.
6,419,903 B1 7/2002 Xu et al.
6,419,906 B1 7/2002 Xu et al.
6,428,825 B2 8/2002 Sharma et al.
6,432,460 B1 8/2002 Zietlow et al.
6,436,464 B1 8/2002 Euber
6,454,788 B1 9/2002 Ashton
6,467,621 B1 10/2002 Ishida
6,468,516 B1 10/2002 Geria et al.
6,472,003 B2 10/2002 Barrett-Reis et al.
6,482,517 B1 11/2002 Anderson
6,488,963 B1 12/2002 McGinity et al.
6,495,599 B2 12/2002 Auestad et al.
6,503,532 B1 1/2003 Murty et al.
6,509,072 B2 1/2003 Bening et al.
6,534,090 B2 3/2003 Puthli et al.
6,552,024 B1 4/2003 Chen et al.
6,575,999 B1 6/2003 Rohrig
6,589,576 B2 7/2003 Borschel et al.
6,592,887 B2 7/2003 Zerbe et al.
6,596,298 B2 7/2003 Leung et al.
6,596,302 B2 7/2003 O'Connor et al.
6,599,542 B1 7/2003 Abdel-Malik et al.
6,610,338 B2 8/2003 Tang
6,620,440 B1 9/2003 Hsia et al.
6,655,112 B1 12/2003 Cremer et al.
6,656,493 B2 12/2003 Dzija et al.
6,660,292 B2 12/2003 Zerbe et al.
6,667,060 B1 12/2003 Vandecruys et al.
6,668,839 B2 12/2003 Williams
6,708,826 B1 3/2004 Ginsberg et al.
6,709,671 B2 3/2004 Zerbe et al.
6,720,006 B2 4/2004 Hanke et al.
6,726,054 B2 4/2004 Fagen et al.
6,730,319 B2 5/2004 Maeder et al.
6,752,824 B2 6/2004 Yancy
6,776,157 B2 8/2004 Williams et al.
6,797,283 B1 9/2004 Edgren et al.
6,800,329 B2 10/2004 Horstmann et al.
6,824,829 B2 11/2004 Berry et al.
6,865,860 B2 3/2005 Arakawa et al.
6,905,016 B2 6/2005 Kanios et al.
6,913,766 B1 7/2005 Krumme et al.
6,929,399 B2 8/2005 Nokura
6,929,400 B2 8/2005 Razeti et al.
7,005,142 B2 2/2006 Leon et al.
7,040,503 B2 5/2006 Leichter et al.
7,067,116 B1 6/2006 Bess et al.
7,093,736 B2 8/2006 Maietta et al.
7,115,507 B2 10/2006 Kawase
7,179,788 B2 2/2007 DeFelippis et al.
7,241,411 B2 7/2007 Berry et al.
7,357,891 B2 4/2008 Yang et al.
7,390,503 B1 6/2008 Ahmed et al.
7,425,292 B2 9/2008 Yang et al.
7,428,859 B2 9/2008 Fujita et al.
7,484,640 B2 2/2009 von Falkenhausen et al.
7,531,191 B2 5/2009 Zion et al.
7,579,019 B2 8/2009 Tapolsky et al.
7,591,801 B2 9/2009 Brauker et al.
7,665,896 B1 2/2010 Higgs
7,666,337 B2 2/2010 Yang et al.
7,694,617 B2 4/2010 Habra et al.

(56) References Cited

U.S. PATENT DOCUMENTS

| | | | |
|---|---|---|---|
| 7,824,588 | B2 | 11/2010 | Yang et al. |
| 7,910,031 | B2 | 3/2011 | Yang et al. |
| 8,017,150 | B2 | 9/2011 | Yang et al. |
| 8,051,983 | B2 | 11/2011 | Simon et al. |
| 8,147,866 | B2 | 4/2012 | Finn et al. |
| 2001/0006677 | A1 | 7/2001 | McGinity et al. |
| 2001/0022964 | A1 | 9/2001 | Leung et al. |
| 2001/0046511 | A1 | 11/2001 | Zerbe et al. |
| 2002/0006677 | A1 | 1/2002 | Egermeier et al. |
| 2002/0012689 | A1 | 1/2002 | Stillman |
| 2002/0045582 | A1 | 4/2002 | Margolin et al. |
| 2002/0098198 | A1 | 7/2002 | Watts et al. |
| 2002/0104774 | A1 | 8/2002 | Hammond |
| 2002/0127254 | A1 | 9/2002 | Fotinos et al. |
| 2002/0131990 | A1 | 9/2002 | Barkalow et al. |
| 2002/0147201 | A1 | 10/2002 | Chen et al. |
| 2002/0170567 | A1 | 11/2002 | Rizzotto et al. |
| 2002/0177380 | A1 | 11/2002 | Forman et al. |
| 2003/0035841 | A1 | 2/2003 | Dzija et al. |
| 2003/0044511 | A1 | 3/2003 | Zerbe et al. |
| 2003/0054039 | A1 | 3/2003 | Zyck et al. |
| 2003/0068378 | A1 | 4/2003 | Chen et al. |
| 2003/0069263 | A1 | 4/2003 | Breder et al. |
| 2003/0072865 | A1 | 4/2003 | Bindels et al. |
| 2003/0077315 | A1 | 4/2003 | Lee et al. |
| 2003/0107149 | A1 | 6/2003 | Yang et al. |
| 2003/0118649 | A1 | 6/2003 | Gao et al. |
| 2003/0121932 | A1 | 7/2003 | Wajda |
| 2003/0124176 | A1 | 7/2003 | Hsu et al. |
| 2003/0140760 | A1 | 7/2003 | Bory |
| 2003/0147956 | A1 | 8/2003 | Shefer et al. |
| 2003/0161926 | A1 | 8/2003 | Kemp et al. |
| 2003/0183643 | A1 | 10/2003 | Fagen et al. |
| 2003/0224044 | A1 | 12/2003 | Weibel |
| 2004/0013731 | A1 | 1/2004 | Chen et al. |
| 2004/0024003 | A1 | 2/2004 | Asmussen et al. |
| 2004/0044367 | A1 | 3/2004 | Yancy |
| 2004/0058457 | A1 | 3/2004 | Huang et al. |
| 2004/0091677 | A1 | 5/2004 | Topolkaraev |
| 2004/0096569 | A1 | 5/2004 | Barkalow et al. |
| 2004/0102867 | A1 | 5/2004 | Palanisamy et al. |
| 2004/0111275 | A1 | 6/2004 | Kroll et al. |
| 2004/0120991 | A1 | 6/2004 | Gardner et al. |
| 2004/0136924 | A1 | 7/2004 | Boyd et al. |
| 2004/0137458 | A1 | 7/2004 | Archambault et al. |
| 2004/0156901 | A1 | 8/2004 | Thakur et al. |
| 2004/0191302 | A1 | 9/2004 | Davidson |
| 2004/0209057 | A1 | 10/2004 | Enlow et al. |
| 2004/0219109 | A1 | 11/2004 | Hatch |
| 2004/0241242 | A1 | 12/2004 | Fuisz et al. |
| 2005/0003048 | A1 | 1/2005 | Pearce et al. |
| 2005/0011776 | A1 | 1/2005 | Nagel |
| 2005/0019588 | A1 | 1/2005 | Berry et al. |
| 2005/0035133 | A1 | 2/2005 | Gerulski et al. |
| 2005/0037055 | A1 | 2/2005 | Yang et al. |
| 2005/0048102 | A1 | 3/2005 | Tapolsky et al. |
| 2005/0055123 | A1 | 3/2005 | Franz |
| 2005/0089548 | A1 | 4/2005 | Virgalitto et al. |
| 2005/0095272 | A1 | 5/2005 | Augello |
| 2005/0115862 | A1 | 6/2005 | Maietta |
| 2005/0118217 | A1 | 6/2005 | Barnhart et al. |
| 2005/0118271 | A1 | 6/2005 | Schliecker et al. |
| 2005/0136115 | A1 | 6/2005 | Kulkarni et al. |
| 2005/0147658 | A1 | 7/2005 | Tapolsky et al. |
| 2005/0163714 | A1 | 7/2005 | Sukhishvili et al. |
| 2005/0170138 | A1 | 8/2005 | Berry |
| 2005/0191349 | A1 | 9/2005 | Boehm et al. |
| 2005/0192309 | A1 | 9/2005 | Palermo et al. |
| 2005/0214251 | A1 | 9/2005 | Pohl et al. |
| 2005/0222781 | A1 | 10/2005 | Yue et al. |
| 2005/0232977 | A1 | 10/2005 | Khan et al. |
| 2005/0239845 | A1 | 10/2005 | Proehl et al. |
| 2006/0023976 | A1 | 2/2006 | Alvater et al. |
| 2006/0039958 | A1 | 2/2006 | Fuisz et al. |
| 2006/0071057 | A1 | 4/2006 | Aschenbrenner et al. |
| 2006/0073190 | A1 | 4/2006 | Carroll et al. |
| 2006/0083786 | A1 | 4/2006 | Chaudhari et al. |
| 2006/0093679 | A1 | 5/2006 | Mayer et al. |
| 2006/0104910 | A1 | 5/2006 | Lerner |
| 2006/0147493 | A1 | 7/2006 | Yang et al. |
| 2006/0163269 | A1 | 7/2006 | Anderson et al. |
| 2006/0180604 | A1 | 8/2006 | Ginsberg et al. |
| 2006/0182796 | A1 | 8/2006 | Wu et al. |
| 2006/0189772 | A1 | 8/2006 | Scheibel et al. |
| 2006/0198790 | A1 | 9/2006 | Dugger, III et al. |
| 2006/0198885 | A1 | 9/2006 | Dharmadhikari et al. |
| 2006/0210610 | A1 | 9/2006 | Davidson et al. |
| 2006/0213348 | A1 | 9/2006 | Loibl |
| 2006/0215941 | A1 | 9/2006 | Golbert |
| 2006/0246141 | A1 | 11/2006 | Liversidge et al. |
| 2006/0264448 | A1 | 11/2006 | Pryde |
| 2006/0281775 | A1 | 12/2006 | Kelly, II et al. |
| 2006/0286108 | A1 | 12/2006 | Bell |
| 2007/0027213 | A1 | 2/2007 | Oberegger et al. |
| 2007/0045148 | A1 | 3/2007 | Saclier et al. |
| 2007/0069416 | A1 | 3/2007 | Yang et al. |
| 2007/0087036 | A1 | 4/2007 | Durschlag et al. |
| 2007/0098746 | A1 | 5/2007 | Nichols et al. |
| 2007/0122455 | A1 | 5/2007 | Myers et al. |
| 2007/0138049 | A1 | 6/2007 | Bitner |
| 2007/0148097 | A1 | 6/2007 | Finn et al. |
| 2007/0170196 | A1 | 7/2007 | Libohova et al. |
| 2007/0205127 | A1 | 9/2007 | Barndt et al. |
| 2007/0231368 | A1 | 10/2007 | Wang et al. |
| 2007/0267433 | A1 | 11/2007 | Fuisz et al. |
| 2007/0281003 | A1 | 12/2007 | Fuisz et al. |
| 2008/0044454 | A1 | 2/2008 | Yang et al. |
| 2008/0073235 | A1 | 3/2008 | Harada et al. |
| 2008/0075825 | A1 | 3/2008 | Fuisz et al. |
| 2008/0081071 | A1 | 4/2008 | Sanghvi et al. |
| 2008/0105582 | A1 | 5/2008 | Ludwig et al. |
| 2008/0233174 | A1 | 9/2008 | Myers et al. |
| 2008/0242558 | A1 | 10/2008 | Belcher et al. |
| 2008/0242736 | A1 | 10/2008 | Fuisz |
| 2008/0254105 | A1 | 10/2008 | Tapolsky et al. |
| 2008/0260805 | A1 | 10/2008 | Yang et al. |
| 2008/0260809 | A1 | 10/2008 | Yang et al. |
| 2008/0268116 | A1 | 10/2008 | Kring |
| 2008/0290106 | A1 | 11/2008 | van der Klaauw et al. |
| 2008/0299197 | A1 | 12/2008 | Tongeguzzo et al. |
| 2008/0300173 | A1 | 12/2008 | DeFrees |
| 2008/0308449 | A1 | 12/2008 | Intini |
| 2009/0004254 | A1 | 1/2009 | Maibach |
| 2009/0009332 | A1 | 1/2009 | Nunez et al. |
| 2009/0014491 | A1 | 1/2009 | Fuisz et al. |
| 2009/0029074 | A1 | 1/2009 | Sasine et al. |
| 2009/0074333 | A1 | 3/2009 | Griebel et al. |
| 2009/0104270 | A1 | 4/2009 | Myers et al. |
| 2009/0146336 | A1 | 6/2009 | Masi |
| 2009/0181075 | A1 | 7/2009 | Gordon et al. |
| 2009/0192075 | A1 | 7/2009 | Steiner |
| 2009/0196907 | A1 | 8/2009 | Bunick et al. |
| 2009/0297614 | A1 | 12/2009 | Rademacher et al. |
| 2010/0015128 | A1 | 1/2010 | Lee et al. |
| 2010/0087470 | A1 | 4/2010 | Oksche et al. |
| 2010/0092545 | A1 | 4/2010 | Yang et al. |
| 2010/0178254 | A1 | 7/2010 | Hariharan et al. |
| 2010/0221309 | A1 | 9/2010 | Myers et al. |
| 2010/0297232 | A1 | 11/2010 | Myers et al. |
| 2011/0189259 | A1 | 8/2011 | Vasisht et al. |
| 2011/0262522 | A1 | 10/2011 | Finn et al. |

FOREIGN PATENT DOCUMENTS

| | | | |
|---|---|---|---|
| CA | 2317491 | C | 6/2008 |
| CH | 639619 | A5 | 11/1983 |
| CN | 1118254 | A | 3/1996 |
| DE | 2449865 | B2 | 6/1981 |
| DE | 2432925 | C3 | 11/1985 |
| DE | 3630603 | C2 | 6/1989 |
| DE | 19646392 | A1 | 5/1998 |
| DE | 202004003781 | U1 | 5/2004 |
| EP | 0021178 | B1 | 1/1981 |
| EP | 0095892 | A1 | 12/1983 |

(56) References Cited

FOREIGN PATENT DOCUMENTS

| | | | |
|---|---|---|---|
| EP | 0065370 | B1 | 1/1985 |
| EP | 0248548 | B1 | 5/1987 |
| EP | 0285568 | A2 | 3/1988 |
| EP | 0274431 | A2 | 7/1988 |
| EP | 0219762 | B1 | 12/1990 |
| EP | 0259749 | B1 | 8/1991 |
| EP | 0200508 | B1 | 10/1991 |
| EP | 0241178 | B1 | 1/1992 |
| EP | 0514691 | A2 | 4/1992 |
| EP | 0273069 | B1 | 10/1992 |
| EP | 0250187 | B1 | 9/1993 |
| EP | 0452446 | B1 | 12/1993 |
| EP | 0598606 | A1 | 5/1994 |
| EP | 0381194 | B1 | 8/1994 |
| EP | 0440462 | B1 | 12/1994 |
| EP | 0636364 | A1 | 1/1995 |
| EP | 0450141 | B1 | 5/1995 |
| EP | 0460588 | B1 | 8/1995 |
| EP | 0514691 | B1 | 1/1996 |
| EP | 0598606 | B1 | 6/1999 |
| EP | 1143940 | | 7/2000 |
| EP | 1110546 | A1 | 6/2001 |
| EP | 1177788 | A2 | 2/2002 |
| EP | 1219291 | A1 | 3/2002 |
| EP | 1243523 | A1 | 9/2002 |
| EP | 0949925 | B1 | 1/2004 |
| EP | 1504765 | A1 | 2/2005 |
| EP | 1267829 | B1 | 5/2006 |
| EP | 1674078 | A2 | 6/2006 |
| EP | 1852041 | A2 | 11/2007 |
| EP | 1897543 | A1 | 3/2008 |
| EP | 1591106 | B1 | 7/2009 |
| EP | 2105389 | A1 | 9/2009 |
| EP | 2253224 | A1 | 11/2010 |
| EP | 2305310 | A1 | 4/2011 |
| FR | 2716098 | A1 | 8/1995 |
| GB | 1061557 | | 3/1967 |
| GB | 1154317 | | 6/1969 |
| GB | 1510999 | | 5/1978 |
| GB | 2447016 | A | 9/2009 |
| JP | 56100714 | A | 8/1981 |
| JP | 62126950 | A | 6/1987 |
| JP | 2265444 | A | 10/1990 |
| JP | 473268 | A | 3/1992 |
| JP | 5147140 | A | 6/1993 |
| JP | 7322812 | A | 12/1995 |
| JP | 11255247 | A | 9/1999 |
| JP | 2001048196 | A | 2/2001 |
| JP | 2001225851 | A | 8/2001 |
| JP | 2001279100 | A | 10/2001 |
| JP | 2003312688 | A | 11/2003 |
| JP | 2004222663 | A | 8/2004 |
| JP | 2006143335 | A | 6/2006 |
| JP | 2008011194 | A | 1/2008 |
| WO | 9105540 | A1 | 5/1991 |
| WO | 9215289 | A1 | 9/1992 |
| WO | 9505416 | A2 | 2/1995 |
| WO | 9518046 | A1 | 7/1995 |
| WO | 9530601 | A1 | 11/1995 |
| WO | 9615903 | A1 | 5/1996 |
| WO | 9625150 | A1 | 8/1996 |
| WO | 9731621 | A1 | 9/1997 |
| WO | 9732573 | A1 | 9/1997 |
| WO | 9810993 | A1 | 3/1998 |
| WO | 9817251 | A1 | 4/1998 |
| WO | 9935051 | A1 | 7/1999 |
| WO | 9955312 | A2 | 11/1999 |
| WO | 0018365 | A2 | 4/2000 |
| WO | 0024647 | A1 | 5/2000 |
| WO | 0042992 | A2 | 7/2000 |
| WO | 0103917 | A2 | 1/2001 |
| WO | 0130288 | A1 | 5/2001 |
| WO | 0143728 | A1 | 6/2001 |
| WO | 0156904 | A1 | 8/2001 |
| WO | 0168452 | A1 | 9/2001 |
| WO | 0170194 | A1 | 9/2001 |
| WO | 0170197 | A2 | 9/2001 |
| WO | 0191721 | A2 | 12/2001 |
| WO | 0205789 | A2 | 1/2002 |
| WO | 0205820 | A1 | 1/2002 |
| WO | 0207711 | A1 | 1/2002 |
| WO | 2006017462 | A2 | 2/2002 |
| WO | 0243657 | A2 | 6/2002 |
| WO | 02062315 | A1 | 8/2002 |
| WO | 02074238 | A2 | 9/2002 |
| WO | 02091965 | A1 | 11/2002 |
| WO | 03011259 | A1 | 2/2003 |
| WO | 03015749 | A1 | 2/2003 |
| WO | 03030881 | A1 | 4/2003 |
| WO | 03030882 | A1 | 4/2003 |
| WO | 03030883 | A1 | 4/2003 |
| WO | 03043659 | A1 | 5/2003 |
| WO | 2004009445 | A2 | 1/2004 |
| WO | 2004035407 | A1 | 4/2004 |
| WO | 2004043165 | A1 | 5/2004 |
| WO | 2004045305 | A2 | 6/2004 |
| WO | 2004045537 | A2 | 6/2004 |
| WO | 2004052335 | A1 | 6/2004 |
| WO | 2004060298 | A2 | 7/2004 |
| WO | 2004087084 | A1 | 10/2004 |
| WO | 2004113193 | A1 | 12/2004 |
| WO | 2005020933 | A2 | 3/2005 |
| WO | 2005035776 | A2 | 4/2005 |
| WO | 2005039499 | A2 | 5/2005 |
| WO | 2005074867 | A1 | 8/2005 |
| WO | 2005102287 | A2 | 11/2005 |
| WO | 2005102863 | A1 | 11/2005 |
| WO | 2005123074 | A1 | 12/2005 |
| WO | 2006004480 | A1 | 1/2006 |
| WO | 2006031209 | A1 | 3/2006 |
| WO | 2006037979 | A2 | 4/2006 |
| WO | 2006039264 | A1 | 4/2006 |
| WO | 2006037425 | A1 | 8/2006 |
| WO | 2006085210 | A1 | 8/2006 |
| WO | 2006133948 | A2 | 12/2006 |
| WO | 2007015105 | A2 | 2/2007 |
| WO | 2007067494 | A1 | 6/2007 |
| WO | 2007070632 | A2 | 6/2007 |
| WO | 2008011194 | A2 | 1/2008 |
| WO | 2008025791 | A1 | 3/2008 |
| WO | 2008036299 | A2 | 3/2008 |
| WO | 2008040534 | A2 | 4/2008 |
| WO | 2009044118 | A2 | 4/2009 |
| WO | 2009052421 | A1 | 4/2009 |
| WO | 2009027625 | A2 | 5/2009 |
| WO | 2009105540 | A1 | 8/2009 |

OTHER PUBLICATIONS

Bhumkar et al., "Chitosan Reduced Gold Nanoparticles as Novel Carriers for Transmucosal Delivery of Insulin", Pharmaceutical Research; 24(8): 1415-1426 (2007).

Bowen P., "Particle Size Distribution Measurement from Millimeters to Nanometers and from Rods to Platelets", Journal of Dispersion Science and Technology; 23(5): 631-662 (2002).

Trademark Reg. No. 2,944,841—registered Apr. 26, 2005 to Reynolds Metal Co for "Ez Slide".

Hariharan et al., "Thin Film Technology, Orally Dissolving Film Strips (ODFS): The Final Evolution of Orally Dissolving Dosage Forms," Drug Delivery Technology; 9(2): 24-29 (2009).

Joshi et al., "Gold Nanoparticles as Carrier for Efficient Transmucosal Insulin Delivery", Langmuir; 22: 300-305 (2006).

Ojeda et al., "Preparation of multifunctional glyconanoparticles as a platform for potential carbohydrate-based anticancer vaccines", Carbohydrate Research; 342: 448-459 (2007).

U.S. Department of Health and Human Services Food and Drug Administration Center for Drug Evaluation and Research (CDER) "Guidance for Industry—Incorporation of Physical-Chemical Identifiers into Solid Oral Dosage Form Drug Products for Anticounterfeiting" Silver Spring, MD; 1-8 (Jul. 9, 2009).

Boo, Woong Jae, "Characterization of Thin Film Properties of Melamine Based Dendrimer Nanoparticles", Thesis for Texas A&M University, Dec. 2003.

(56) References Cited

OTHER PUBLICATIONS

Blank, Z. et al., "Structural studies of organic gels by SEM", J. Material Science 9:1815-1822 (1974).
CAS Presents, "Common Chemistry", http://www.commonchemistry.org.ChemicalDetail.aspx?ref=25322-68-3 &terms=polyeth..2009-10-28.
Huus et al., "Thermal Dissociation and Unfolding of Insulin", Biochemistry, 44: 11171-11177 (2005).
Steiner et al., "Organic Derivatives of Alginic Acid", Industrial and Engineering Chemistry; 43(9): 2073-2077 (1951).
"Cellulose" Kirk-Othmer Concise Encyclopeida of Chemical Technology; Abridged version of the 24 Volume, NY, Wiley; 227-228 (1978-1984).
Barton, S. et al "Citric Buffer Calculation", Version 1.1, Nov. 19, 2000.
Bodmeier, Roland, "Evaluation of Drug-Containing Polymer Films Prepared from Aqueous Latexes", Pharmaceutical Research, vol. 6, No. 8 (1989).
Cholewinski et al., Pharmaceutica Acta Helvetiae, 71:405-419, 1996.
Croscarmellose sodium http://ww.nbent.com/crosscarmellose.htm (Mar. 29, 2005).
Di Donato et al., J. Biol. Chem, 268(7): 4745-4751, 1993.
Eiamtrakarn et al., "Gastrointestinal Mucoadhesive Path System (GI-MAPS) for oral administration of G-CSF, a model protein", Bipmaterials 23: 145-152 (2002).
Endo and Ueda, Fabad J. Pharm. Sci., 29:27-38, 2004.
Engel, June V PhD, "The Benefits of Eating Fibre" http://www.diabetes.ca/common/PrintVersion.asp?ID=45493 May 11, 2005.
Flick, E., Water-Soluble Resins—An Industrial Guide, 1991 (2nd Ed.) William Andrew Publishing/Noyes, pp. 389-392.
Goldberg et al., "Biotechnology and Food Ingredients", Springer: 352 (1991).
Hadvary et al., "Inhibition of pancreatic lipase in vitro by the covalent inhibitor tetrahydrolistatin", Biochem J.; 256: 357-361 (1988).
Ko et al., "Behavior of etrahydrolipstatin in biological model membranes and emulsions", J. of Lipid Research; 38:1544-1552 (1997).
Kuhtreiber. In Cell Encapsulation and Therapeutics . Copyright 1999.
Lazaridou et al.; Thermophysical properties of chitosan, chitosanstarch and chitosan-pullulan films near the glass transition; Elsevier Science Ltd.; 2002; pp. 179-190.
Leathers, Appl. Microbiol. Biotechnol., 62: 468-473, 2003.
LePearson, S. Le et al., "Near infrared drying of pharmaceutical thin films: experimental analysis of internal mass transport," Chemical Engineering and Processing; (1998) pp. 257-263, 37.
Mahmood et al., "A limited sampling method for the estimation of AUC and Cmax of cabamazepine and carbamazepine epoxide folowing a single and multiple dose of a sustained-release product", BR J Clin Pharmacol; 45:241-246 (1998).
mix. http://www.askoxford.com/concise_oed/mixx?view=uk. Accessed Dec. 23, 2004.
Oriski, S.C., "Johnson debuts cutter for new Saran film" Packaging World Oct. 1, 2004, http://www.packworld.com/view-18051.
Peh Kok Khiang et al., "Polymeric Films as Vehicle for Buccal Delivery: Swelling, Mechanical, and Bioadhesive Properties," J Pharm Pharmaceut Sci (1999) pp. 53-61, 2:2.
Repka et al., "Bioadhesive properties of hydroxypropylcellulose topical films produced by hot-melt extrusion," Journal of Controlled Release, 70: 341-351 (2001).
Repka et al., "Influence of Vitamin E TPGS on the properties of hydrophilic films produced by hot-melt extrusion," Int. J. Pharmaceutics, 202: 63-70 (2000).
Senel, S., et al., "Chitosan films and hydrogels of chlorhexidine gluconate for oral mucosal delivery", Int. J. Pharmaceutics, 193: pp. 197-203 (2000).
Stella, V., et al., "Gliadin Films. I: Preparation and in vitro evaluation as a carrier for controlled drug release", Int., J. Pharmaceutics, 121: pp. 117-121 (1995).
Sudafed & Sudafed PE, http://www.sudafed.com/products/pe_quickstrips.html (Aug. 17, 2007).
Well—Definition of from the American Heritage College Dictionary, 3rd Ed., p. 1531 (1993).
Bauer, K.H. et al., "Pharmazeutische Technologie", pp. 208-209 (1997).
Pinnamanemi, S. et al., "Formulation approaches for orally administered poorly soluble drugs", Pharmazie 57(5): 291-300 (2002).
Chaumeil, J.C. "Micronization: A Method of Improving the Bioavailability of Poorly Soluble Drugs", Methods and Findings in Experimental and Clinical Pharmacology 20(3): 211-215 (1998).
Voigt, R. et al., "Pharmaseutische Technology fur Studium und Berf", pp. 179-180 (1995).
Nanda, A. et al., "An update on taste masking technologies for oral pharmaceuticals", Indian J Pharma Sci 64(1): 10-17 (2002).
Bronschein, M. et al., "Micro- und Nanopartikeln als Arzneliestofftragersysteme unter besonderer Berucksichtigung der Herstellungsmethoden", Die Pharmazie 44(9): 585-593 (1989).
Cohen E. et al., "Modern Coating and Drying Technology", pp. 268-277 (1992).
Index of Transaction History for Ex Parte Reexamination Control No. 90/012,098, current as of Jun. 4, 2014.
Index of Documents for Inter Partes Review Case No. IPR2013-00316, current as of Jun. 4, 2014.
Index of Transaction History for Ex Parte Reexamination Control No. 90/012,097, current as of Jun. 4, 2014.
Index of Documents for Inter Partes Review Case No. IPR2013-00315, current as of Jun. 4, 2014.
Index of Transaction History for Inter Partes Reexamination Control No. 95/002,171, current as of Jun. 4, 2014.
Index of Transaction History for Inter Partes Reexamination Control No. 95/001,753, current as of Jun. 4, 2014.
Index of Transaction History for Inter Partes Reexamination Control No. 95/002,170, current as of Jun. 4, 2014.
Index of Documents for Inter Partes Review Case No. IPR2014-00794, current as of Jun. 4, 2014.

500

500

Normalized to GAPDH, most of the ISGs are induced.

| Ex. | Polymer Component Reference | % Solids of solution | Viscosity (cp) at 5 rpm | % moisture | Film thickness (mils) | Film strength | Tear Resistance | Tendency to go to roof of mouth | 180° bend test | Film molding | Dis-solution (sec) | Rating of dissolution in mouth | Time in oven (min) |
|---|---|---|---|---|---|---|---|---|---|---|---|---|---|
| EI | PEO/PVP (60/40) | 45.0 | 14800 | 2.21 | 3.8 | Adequate | Excellent | Low | Passed | No | 3 | Fast to Moderate | 9 |
| EJ | PEO/PVP (40/60) | 50.0 | 6600 | 2.86 | 4 | Weak | Low to moderate | High | Passed | No | 3 | Fast | 8 |
| EK | PEO/Starch (80/20) | 40.0 | 3440 | 2.27 | 4.5 | Adequate to good | Excellent | High | Passed | No | 3 | Fast to Moderate | 8 |
| EL | PEO/CMC (80/20) | 37.5 | 121,200 | 1.96 | 4.1 | Good | Excellent | High | Passed | No | 5 | Slow | 9 |
| EM | PEO/CMC (60/40) | 30.0 | 82,000 | 4.21 | 3.45 | Weak | Good | High | Passed | No | 3 | Slow to Moderate | 9 |
| EN | PEO/CMC (40/60) | 30.0 | 185,000 | 3.07 | 3.5 | Adequate | Very low | High | Failed | No | 4 | Slow | 9 |
| EO | PEO/HPC (80/20) | 37.5 | 21,200 | 1.65 | 4 | Good | Excellent | High | Passed | No | 4 | Fast | 8 |
| EP | PEO/HPC (60/40) | 37.5 | 17,000 | 2.84 | 3.8 | Adequate | Excellent | High | Passed | No | 4 | Fast | 9 |
| EQ | PEO/HPC (40/60) | 42.5 | 43,400 | 2.83 | 4.5 | Poor to adequate | Poor to good | High | Passed | No | 7 | Fast to Moderate | 7 |
| ER | PEO/HPC (20/80) | 42.5 | 46,400 | 2.33 | 4.4 | Adequate to good | Poor | Low | Passed | No | 14-15 | Slow | 9 |
| ES | PEO/HPMC (80/20) | 37.5 | 29,000 | 2.14 | 4.4 | Adequate | Good | High | Passed | Yes | 4 | Fast to Moderate | 8 |
| ET | PEO/HPMC (60/40) | 37.5 | 47,000 | 2.37 | 3.9 | Poor to adequate | Slight | High | Passed | Yes | 3 | Fast to Moderate | 9 |
| EU | PEO/HPMC (40/60) | 35.0 | 54,800 | 3.55 | 4.5 | Adequate to good | Low | Low | Passed | Yes | 8 | Slow | 8 |
| EV | PEO/HPMC (20/80) | 35.0 | 96,600 | 4.43 | 4.5 | Good | Low | Low | Passed | No | 22 | Slow | 10 |
| EW | PEO/PVA (80/20) | 37.5 | 41,600 | 2.92 | 9 | Weak | Moderate | High | Passed | No | 3 | Moderate | 10 |

FIG. 38

PROCESS FOR MANUFACTURING A RESULTING MULTI-LAYER PHARMACEUTICAL FILM

CROSS-REFERENCE TO RELATED APPLICATIONS

This application is a continuation of U.S. application Ser. No. 13/853,276, filed Mar. 29, 2013, which is a continuation of U.S. application Ser. No. 13/035,328, filed Feb. 25, 2012 now abandoned, which is a continuation of U.S. application Ser. No. 12/614,928, filed Nov. 9, 2009, now U.S. Pat. No. 7,897,080, which is a continuation of U.S. application Ser. No. 10/856,176, filed May 28, 2004, now U.S. Pat. No. 7,666,337, which claims the benefit of U.S. Provisional Application No. 60/473,902, filed May 28, 2003 and is a continuation-in-part of U.S. application Ser. No. 10/768,809, filed Jan. 30, 2004, now U.S. Pat. No. 7,357,891, which claims benefit to U.S. Provisional Application No. 60/443,741 filed Jan. 30, 2003 and is a continuation-in-part of:

(a) PCT/US02/32575 filed Oct. 11, 2002, which claims priority to: (1) U.S. application Ser. No. 10/074,272, filed Feb. 14, 2002, now U.S. Pat. No. 7,425,292, which claims benefit to U.S. Provisional Application No. 60/328,868, filed Oct. 12, 2001 and (2) U.S. Provisional Application No. 60/386,937, filed Jun. 7, 2002;

(b) PCT/US02/32594, filed Oct. 11, 2002, which claims priority to: (1) U.S. Provisional Application No. 60/414,276, filed Sep. 27, 2002, (2) U.S. application Ser. No. 10/074,272, filed Feb. 14, 2002, which claims benefit to U.S. Provisional Application No. 60/328,868, filed Oct. 12, 2001 and (3) U.S. Provisional Application No. 60/386,937, filed Jun. 7, 2002; and (c) PCT/US02/32542, filed Oct. 11, 2002, which claims priority to: (1) U.S. Provisional Application No. 60/371,940, filed Apr. 11, 2002, (2) U.S. application Ser. No. 10/074,272, filed Feb. 14, 2002, which claims benefit to U.S. Provisional Application No. 60/328,868, filed Oct. 12, 2001 and (3) U.S. Provisional Application No. 60/386,937, filed Jun. 7, 2002.

FIELD OF THE INVENTION

The invention relates to rapidly dissolving films and methods of their preparation. The films contain a polymer component, which includes polyethylene oxide optionally blended with cellulosic polymers. The films may also contain an active ingredient that is evenly distributed throughout the film. The even or uniform distribution is achieved by controlling one or more parameters, and particularly the elimination of air pockets prior to and during film formation and the use of a drying process that reduces aggregation or conglomeration of the components in the film as it forms into a solid structure.

BACKGROUND OF THE RELATED TECHNOLOGY

Active ingredients, such as drugs or pharmaceuticals, may be prepared in a tablet form to allow for accurate and consistent dosing. However, this form of preparing and dispensing medications has many disadvantages including that a large proportion of adjuvants that must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy the controlled release properties.

As an alternative to tablets and pills, films may be used to carry active ingredients such as drugs, pharmaceuticals, and the like. However, historically films and the process of making drug delivery systems therefrom have suffered from a number of unfavorable characteristics that have not allowed them to be used in practice.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

Examination of films made in accordance with the process disclosed in Fuchs, however, reveals that such films suffer from the aggregation or conglomeration of particles, i.e., self-aggregation, making them inherently non-uniform. This result can be attributed to Fuchs' process parameters, which although not disclosed likely include the use of relatively long drying times, thereby facilitating intermolecular attractive forces, convection forces, air flow and the like to form such agglomeration.

The formation of agglomerates randomly distributes the film components and any active present as well. When large dosages are involved, a small change in the dimensions of the film would lead to a large difference in the amount of active per film. If such films were to include low dosages of active, it is possible that portions of the film may be substantially devoid of any active. Since sheets of film are usually cut into unit doses, certain doses may therefore be devoid of or contain an insufficient amount of active for the recommended treatment. Failure to achieve a high degree of accuracy with respect to the amount of active ingredient in the cut film can be harmful to the patient. For this reason, dosage forms formed by processes such as Fuchs, would not likely meet the stringent standards of governmental or regulatory agencies, such as the U.S. Federal Drug Administration ("FDA"), relating to the variation of active in dosage forms. Currently, as required by various world regulatory authorities, dosage forms may not vary more than 10% in the amount of active present. When applied to dosage units based on films, this virtually mandates that uniformity in the film be present.

The problems of self-aggregation leading to non-uniformity of a film were addressed in U.S. Pat. No. 4,849,246 to Schmidt ("Schmidt"). Schmidt specifically pointed out that the methods disclosed by Fuchs did not provide a uniform film and recognized that that the creation of a non-uniform film necessarily prevents accurate dosing, which as discussed above is especially important in the pharmaceutical area. Schmidt abandoned the idea that a mono-layer film, such as described by Fuchs, may provide an accurate dosage form and instead attempted to solve this problem by forming a multi-layered film. Moreover, his process is a multi-step process that adds expense and complexity and is not practical for commercial use.

Other U.S. patents directly addressed the problems of particle self-aggregation and non-uniformity inherent in conventional film forming techniques. In one attempt to overcome non-uniformity, U.S. Pat. No. 5,629,003 to Horstmann et al. and U.S. Pat. No. 5,948,430 to Zerbe et al. incorporated additional ingredients, i.e. gel formers and polyhydric alcohols respectively, to increase the viscosity of the film prior to drying in an effort to reduce aggregation of the components in the film. These methods have the disadvantage of requiring additional components, which translates to additional cost and manufacturing steps. Furthermore, both methods employ the use the conventional time-consuming drying methods such as a high-temperature air-bath using a drying oven, drying tunnel, vacuum drier, or other such drying equipment. The long length of drying time aids in promoting the aggregation of the active and other adjuvant, notwithstanding the use of viscosity modifiers. Such processes also run the risk of exposing the active, i.e., a drug, or vitamin C, or other components to prolonged exposure to moisture and elevated temperatures, which may render it ineffective or even harmful.

In addition to the concerns associated with degradation of an active during extended exposure to moisture, the conventional drying methods themselves are unable to provide uniform films. The length of heat exposure during conventional processing, often referred to as the "heat history", and the manner in which such heat is applied, have a direct effect on the formation and morphology of the resultant film product. Uniformity is particularly difficult to achieve via conventional drying methods where a relatively thicker film, which is well-suited for the incorporation of a drug active, is desired. Thicker uniform films are more difficult to achieve because the surfaces of the film and the inner portions of the film do not experience the same external conditions simultaneously during drying. Thus, observation of relatively thick films made from such conventional processing shows a non-uniform structure caused by convection and intermolecular forces and requires greater than 10% moisture to remain flexible. The amount of free moisture can often interfere over time with the drug leading to potency issues and therefore inconsistency in the final product.

Conventional drying methods generally include the use of forced hot air using a drying oven, drying tunnel, and the like. The difficulty in achieving a uniform film is directly related to the rheological properties and the process of water evaporation in the film-forming composition. When the surface of an aqueous polymer solution is contacted with a high temperature air current, such as a film-forming composition passing through a hot air oven, the surface water is immediately evaporated forming a polymer film or skin on the surface. This seals the remainder of the aqueous film-forming composition beneath the surface, forming a barrier through which the remaining water must force itself as it is evaporated in order to achieve a dried film. As the temperature outside the film continues to increase, water vapor pressure builds up under the surface of the film, stretching the surface of the film, and ultimately ripping the film surface open allowing the water vapor to escape. As soon as the water vapor has escaped, the polymer film surface reforms, and this process is repeated, until the film is completely dried. The result of the repeated destruction and reformation of the film surface is observed as a "ripple effect" which produces an uneven, and therefore non-uniform film. Frequently, depending on the polymer, a surface will seal so tightly that the remaining water is difficult to remove, leading to very long drying times, higher temperatures, and higher energy costs.

Other factors, such as mixing techniques, also play a role in the manufacture of a pharmaceutical film suitable for commercialization and regulatory approval. Air can be trapped in the composition during the mixing process or later during the film making process, which can leave voids in the film product as the moisture evaporates during the drying stage. The film frequently collapse around the voids resulting in an uneven film surface and therefore, non-uniformity of the final film product. Uniformity is still affected even if the voids in the film caused by air bubbles do not collapse. This situation also provides a non-uniform film in that the spaces, which are not uniformly distributed, are occupying area that would otherwise be occupied by the film composition. None of the above-mentioned patents either addresses or proposes a solution to the problems caused by air that has been introduced to the film.

Therefore, there is a need for methods and compositions for film products, which use a minimal number of materials or components, and which provide a substantially non-self-aggregating uniform heterogeneity throughout the area of the films. Desirably, such films are produced through a selection of a polymer or combination of polymers that will provide a desired viscosity, a film-forming process such as reverse roll coating, and a controlled, and desirably rapid, drying process which serves to maintain the uniform distribution of non-self-aggregated components without the necessary addition of gel formers or polyhydric alcohols and the like which appear to be required in the products and for the processes of prior patents, such as the aforementioned Horstmann and Zerbe patents. Desirably, the films will also incorporate compositions and methods of manufacture that substantially reduce or eliminate air in the film, thereby promoting uniformity in the final film product.

SUMMARY OF THE INVENTION

The present invention is directed to rapid-dissolve film products containing at least one water-soluble polymer including polyethylene oxide alone or in combination with a hydrophilic cellulosic polymer, wherein the film product is free of added plasticizers.

Another embodiment of the rapid-dissolve film product includes at least one water-soluble polymer containing about 20% to 100% by weight polyethylene oxide, about 0% to 80% by weight hydroxypropylmethyl cellulose, and about 0% to 80% by weight hydroxypropyl cellulose; an active component; sucralose; precipitated calcium carbonate;

at least one flavoring; simethicone; water; and at least one colorant, wherein the film product is free of added plasticizers, surfactants, and polyalcohols.

Yet another embodiment of the present invention is directed to an edible water-soluble delivery system in the form of a film composition, which contains at least one water-soluble polymer comprising polyethylene oxide alone or in combination with a polymer selected from the group consisting of hydroxypropylmethyl cellulose and hydroxypropyl cellulose, wherein the edible water-soluble delivery system is essentially free of organic solvents, plasticizers, surfactants, and polyalcohols.

The present invention is also directed to processes for making a film having a substantially uniform distribution of components, including the steps of: (a) combining at least one water-soluble polymer comprising polyethylene oxide alone or in combination with a hydrophilic cellulosic polymer, a solvent, and an active component to form a matrix with a uniform distribution of the components; (b) forming a film from the matrix; and (c) drying the film, wherein the film is free of added plasticizers.

BRIEF DESCRIPTION OF THE DRAWINGS

FIG. 38 is presents the components and properties of films prepared in accordance with the method of the present invention.

DETAILED DESCRIPTION OF THE INVENTION

Figure 1:
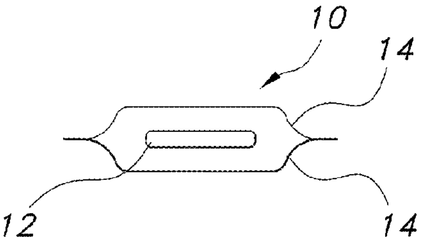
FIG. 1 shows a side view of a package containing a unit dosage film of the present invention.

For the purposes of the present invention the term non-self-aggregating uniform heterogeneity refers to the ability of the films of the present invention, which are formed from one or more components in addition to a polar solvent, to provide a substantially reduced occurrence of, i.e. little or no, aggregation or conglomeration of components within the film as is normally experienced when films are formed by conventional drying methods such as a high-temperature air-bath using a drying oven, drying tunnel, vacuum drier, or other such drying equipment. The term heterogeneity, as used in the present invention, includes films that will incorporate a single component, such as a polymer, as well as combinations of components, such as a polymer and an active. Uniform heterogeneity includes the substantial absence of aggregates or conglomerates as is common in conventional mixing and heat drying methods used to form films.

Furthermore, the films of the present invention have a substantially uniform thickness, which is also not provided by the use of conventional drying methods used for drying water-based polymer systems. The absence of a uniform thickness detrimentally affects uniformity of component distribution throughout the area of a given film.

The film products of the present invention are produced by a combination of a properly selected polymer and a polar solvent, optionally including an active ingredient as well as other fillers known in the art. These films provide a non-self-aggregating uniform heterogeneity of the components within them by utilizing a selected casting or deposition method and a controlled drying process. Examples of controlled drying processes include, but are not limited to, the use of the apparatus disclosed in U.S. Pat. No. 4,631,837 to Magoon ("Magoon"), herein incorporated by reference, as well as hot air impingement across the bottom substrate and bottom heating plates. Another drying technique for obtaining the films of the present invention is controlled radiation drying, in the absence of uncontrolled air currents, such as infrared and radio frequency radiation (i.e. microwaves).

The objective of the drying process is to provide a method of drying the films that avoids complications, such as the noted "rippling" effect, that are associated with conventional drying methods and which initially dry the upper surface of the film, trapping moisture inside. In conventional oven drying methods, as the moisture trapped inside subsequently evaporates, the top surface is altered by being ripped open and then reformed. These complications are avoided by the present invention, and a uniform film is provided by drying the bottom surface of the film first or otherwise preventing the formation of polymer film formation (skin) on the top surface of the film prior to drying the depth of the film. This may be achieved by applying heat to the bottom surface of the film with substantially no top air flow, or alternatively by the introduction of controlled microwaves to evaporate the water or other polar solvent within the film, again with substantially no top air flow. Yet alternatively, drying may be achieved by using balanced fluid flow, such as balanced air flow, where the bottom and top air flows are controlled to provide a uniform film. In such a case, the air flow directed at the top of the film should not create a condition which would cause movement of particles present in the wet film, due to forces generated by the air currents. Additionally, air currents directed at the bottom of the film should desirably be controlled such that the film does not lift up due to forces from the air. Uncontrolled air currents, either above or below the film, can create non-uniformity in the final film products. The humidity level of the area surrounding the top surface may also be appropriately adjusted to prevent premature closure or skinning of the polymer surface.

This manner of drying the films provides several advantages. Among these are the faster drying times and a more uniform surface of the film, as well as uniform distribution of components for any given area in the film. In addition, the faster drying time allows viscosity to quickly build within the film, further encouraging a uniform distribution of components and decrease in aggregation of components in the final film product. Desirably, the drying of the film will occur within about ten minutes or fewer, or more desirably within about five minutes or fewer.

The present invention yields exceptionally uniform film products when attention is paid to reducing the aggregation of the compositional components. By avoiding the introduction of and eliminating excessive air in the mixing process, selecting polymers and solvents to provide a controllable viscosity and by drying the film in a rapid manner from the bottom up, such films result.

The products and processes of the present invention rely on the interaction among various steps of the production of the films in order to provide films that substantially reduce the self-aggregation of the components within the films. Specifically, these steps include the particular method used to form the film, making the composition mixture to prevent air bubble inclusions, controlling the viscosity of the film forming composition and the method of drying the film. More particularly, a greater viscosity of components in the mixture is particularly useful when the active is not soluble in the selected polar solvent in order to prevent the active from settling out. However, the viscosity must not be too great as to hinder or prevent the chosen method of casting, which desirably includes reverse roll coating due to its ability to provide a film of substantially consistent thickness.

In addition to the viscosity of the film or film-forming components or matrix, there are other considerations taken into account by the present invention for achieving desirable film uniformity. For example, stable suspensions are achieved which prevent solid (such as drug particles) sedimentation in non-colloidal applications. One approach provided by the present invention is to balance the density of the particulate ($\rho_p$) and the liquid phase ($\rho_1$) and increase the viscosity of the liquid phase ($\mu$). For an isolated particle, Stokes law relates the terminal settling velocity (Vo) of a rigid spherical body of radius (r) in a viscous fluid, as follows:

$$V_o=(2gr^r)(\rho_p-\rho_1)/9\mu,$$

At high particle concentrations, however, the local particle concentration will affect the local viscosity and density. The viscosity of the suspension is a strong function of solids volume fraction, and particle-particle and particle-liquid interactions will further hinder settling velocity.

Stokian analyses has shown that the incorporation of a third phase, dispersed air or nitrogen, for example, promotes suspension stability. Further, increasing the number of particles leads to a hindered settling effect based on the solids volume fraction. In dilute particle suspensions, the rate of sedimentation, v, can be expressed as:

$$v/V_o=1/(1+\kappa\phi)$$

where $\kappa$=a constant, and $\phi$ is the volume fraction of the dispersed phase. More particles suspended in the liquid phase results in decreased velocity. Particle geometry is also an important factor since the particle dimensions will affect particle-particle flow interactions.

Similarly, the viscosity of the suspension is dependent on the volume fraction of dispersed solids. For dilute suspensions of non-interaction spherical particles, an expression for the suspension viscosity can be expressed as:

$$\mu/\mu_o=1+2.5\phi$$

where $\mu_o$ is the viscosity of the continuous phase and $\phi$ is the solids volume fraction. At higher volume fractions, the viscosity of the dispersion can be expressed as $$\mu/\mu_o=1+2.5\phi+C_1\phi^2+C_2\phi^3+\ldots$$

where C is a constant.

The viscosity of the liquid phase is critical and is desirably modified by customizing the liquid composition to a viscoelastic non-Newtonian fluid with low yield stress values. This is the equivalent of producing a high viscosity continuous phase at rest. Formation of a viscoelastic or a highly structured fluid phase provides additional resistive forces to particle sedimentation. Further, flocculation or aggregation can be controlled minimizing particle-particle interactions. The net effect would be the preservation of a homogeneous dispersed phase.

The addition of hydrocolloids to the aqueous phase of the suspension increases viscosity, may produce viscoelasticity and can impart stability depending on the type of hydrocolloid, its concentration and the particle composition, geometry, size, and volume fraction. The particle size distribution of the dispersed phase needs to be controlled by selecting the smallest realistic particle size in the high viscosity medium, i.e., <500 μm. The presence of a slight yield stress or elastic body at low shear rates may also induce permanent stability regardless of the apparent viscosity. The critical particle diameter can be calculated from the yield stress values. In the case of isolated spherical particles, the maximum shear stress developed in settling through a medium of given viscosity can be given as $$\tau_{max}=3V\mu/2r$$

For pseudoplastic fluids, the viscosity in this shear stress regime may well be the zero shear rate viscosity at the Newtonian plateau.

A stable suspension is an important characteristic for the manufacture of a pre-mix composition which is to be fed into the film casting machinery film, as well as the maintenance of this stability in the wet film stage until sufficient drying has occurred to lock-in the particles and matrix into a sufficiently solid form such that uniformity is maintained. For viscoelastic fluid systems, a rheology that yields stable suspensions for extended time period, such as 24 hours, must be balanced with the requirements of high-speed film casting operations. A desirable property for the films is shear thinning or pseudoplasticity, whereby the viscosity decreases with increasing shear rate. Time dependent shear effects such as thixotropy are also advantageous. Structural recovery and shear thinning behavior are important properties, as is the ability for the film to self-level as it is formed.

The rheology requirements for the inventive compositions and films are quite severe. This is due to the need to produce a stable suspension of particles, for example 30-60 wt %, in a viscoelastic fluid matrix with acceptable viscosity values throughout a broad shear rate range. During mixing, pumping, and film casting, shear rates in the range of $10\text{-}10^5$ $sec.^{-1}$ may be experienced and pseudoplasticity is the preferred embodiment.

In film casting or coating, rheology is also a defining factor with respect to the ability to form films with the desired uniformity. Shear viscosity, extensional viscosity, viscoelasticity, structural recovery will influence the quality of the film. As an illustrative example, the leveling of shear-thinning pseudoplastic fluids has been derived as $$\alpha^{(n-1/n)}=\alpha_o^{(n-1/n)}-((n-1)/(2n-1))(\tau/K)^{1/n}(2\pi/\lambda)^{(3+n)/n}h^{(2n+1)/n}t$$

where $\alpha$ is the surface wave amplitude, $\alpha_o$ is the initial amplitude, $\lambda$ is the wavelength of the surface roughness, and both "n" and "K" are viscosity power law indices. In this example, leveling behavior is related to viscosity, increasing as n decreases, and decreasing with increasing K.

Desirably, the films or film-forming compositions of the present invention have a very rapid structural recovery, i.e. as the film is formed during processing, it doesn't fall apart or become discontinuous in its structure and compositional uniformity. Such very rapid structural recovery retards particle settling and sedimentation. Moreover, the films or film-forming compositions of the present invention are desirably shear-thinning pseudoplastic fluids. Such fluids with consideration of properties, such as viscosity and elasticity, promote thin film formation and uniformity.

Thus, uniformity in the mixture of components depends upon numerous variables. As described herein, viscosity of the components, the mixing techniques and the rheological properties of the resultant mixed composition and wet casted film are important aspects of the present invention. Additionally, control of particle size and particle shape are further considerations. Desirably, the size of the particulate a particle size of 150 microns or less, for example 100 microns or less. Moreover, such particles may be spherical, substantially spherical, or non-spherical, such as irregularly shaped particles or ellipsoidally shaped particles. Ellipsoidally shaped particles or ellipsoids are desirable because of their ability to maintain uniformity in the film forming matrix as they tend to settle to a lesser degree as compared to spherical particles.

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture is desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles or volatile materials such as flavor oils. The actives are added to smaller mixes of the masterbatch just prior to casting. Thus, the masterbatch pre-mix can be allowed to stand for a longer time without concern for instability in drug or other ingredients.

When the matrix is formed including the film-forming polymer and polar solvent in addition to any additives and the active ingredient, this may be done in a number of steps. For example, the ingredients may all be added together or a pre-mix may be prepared. The advantage of a pre-mix is that all ingredients except for the active may be combined in advance, with the active added just prior to formation of the film. This is especially important for actives that may degrade with prolonged exposure to water, air or another polar solvent.

Figure 6:
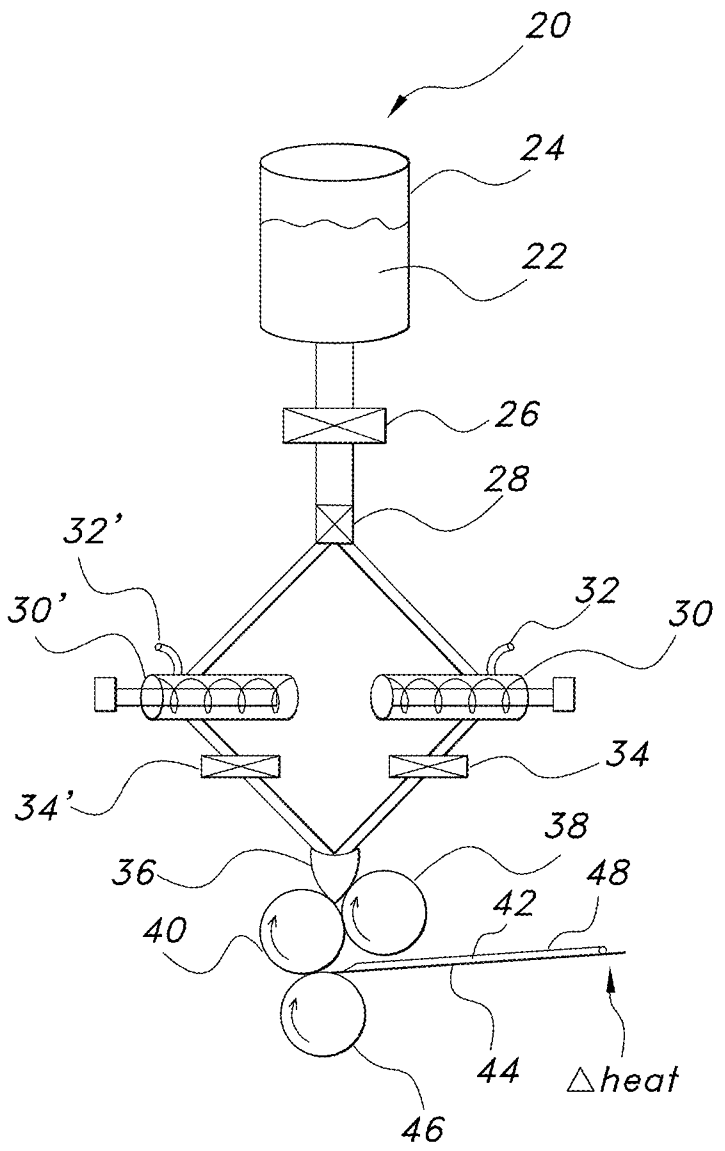
FIG. 6 is a schematic view of an apparatus suitable for preparation of a pre-mix, addition of an active, and subsequent formation of the film.

FIG. 6 shows an apparatus 20 suitable for the preparation of a pre-mix, addition of an active and subsequent formation of a film. The pre-mix or master batch 22, which includes the film-forming polymer, polar solvent, and any other additives except a drug active is added to the master batch feed tank 24. The components for pre-mix or master batch 22 are desirably formed in a mixer (not shown) prior to their addition into the master batch feed tank 24. Then a pre-determined amount of the master batch is controllably fed via a first metering pump 26 and control valve 28 to either or both of the first and second mixers, 30, 30'. The present invention, however, is not limited to the use of two mixers, 30, 30', and any number of mixers may suitably be used. Moreover, the present invention is not limited to any particular sequencing of the mixers 30, 30', such as parallel sequencing as depicted in FIG. 6, and other sequencing or arrangements of mixers, such as series or combination of parallel and series, may suitably be used. The required amount of the drug or other ingredient, such as a flavor, is added to the desired mixer through an opening, 32, 32', in each of the mixers, 30, 30'. Desirably, the residence time of the pre-mix or master batch 22 is minimized in the mixers 30, 30'. While complete dispersion of the drug into the pre-mix or master batch 22 is desirable, excessive residence times may result in leaching or dissolving of the drug, especially in the case for a soluble drug. Thus, the mixers 30, 30' are often smaller, i.e. lower residence times, as compared to the primary mixers (not shown) used in forming the pre-mix or master batch 22. After the drug has been blended with the master batch pre-mix for a sufficient time to provide a uniform matrix, a specific amount of the uniform matrix is then fed to the pan 36 through the second metering pumps, 34, 34'. The metering roller 38 determines the thickness of the film 42 and applies it to the application roller. The film 42 is finally formed on the substrate 44 and carried away via the support roller 46.

While the proper viscosity uniformity in mixture and stable suspension of particles, and casting method are important in the initial steps of forming the composition and film to promote uniformity, the method of drying the wet film is also important. Although these parameters and properties assist uniformity initially, a controlled rapid drying process ensures that the uniformity will be maintained until the film is dry.

The wet film is then dried using controlled bottom drying or controlled microwave drying, desirably in the absence of external air currents or heat on the top (exposed) surface of the film 48 as described herein. Controlled bottom drying or controlled microwave drying advantageously allows for vapor release from the film without the disadvantages of the prior art. Conventional convection air drying from the top is not employed because it initiates drying at the top uppermost portion of the film, thereby forming a barrier against fluid flow, such as the evaporative vapors, and thermal flow, such as the thermal energy for drying. Such dried upper portions serve as a barrier to further vapor release as the portions beneath are dried, which results in non-uniform films. As previously mentioned some top air flow can be used to aid the drying of the films of the present invention, but it must not create a condition that would cause particle movement or a rippling effect in the film, both of which would result in non-uniformity. If top air is employed, it is balanced with the bottom air drying to avoid non-uniformity and prevent film lift-up on the carrier belt. A balance top and bottom air flow may be suitable where the bottom air flow functions as the major source of drying and the top air flow is the minor source of drying. The advantage of some top air flow is to move the exiting vapors away from the film thereby aiding in the overall drying process. The use of any top air flow or top drying, however, must be balanced by a number of factors including, but not limited, to rheological properties of the composition and mechanical aspects of the processing. Any top fluid flow, such as air, also must not overcome the inherent viscosity of the film-forming composition. In other words, the top air flow cannot break, distort or otherwise physically disturb the surface of the composition. Moreover, air velocities are desirably below the yield values of the film, i.e., below any force level that can move the liquids in the film-forming compositions. For thin or low viscosity compositions, low air velocity must be used. For thick or high viscosity compositions, higher air velocities may be used. Furthermore, air velocities are desirable low so as to avoid any lifting or other movement of the film formed from the compositions.

Moreover, the films of the present invention may contain particles that are sensitive to temperature, such as flavors, which may be volatile, or drugs, proteins, or antigens, which may have a low degradation temperature. In such cases, the drying temperature may be decreased while increasing the drying time to adequately dry the uniform films of the present invention. Furthermore, bottom drying also tends to result in a lower internal film temperature as compared to top drying. In bottom drying, the evaporating vapors more readily carry heat away from the film as compared to top drying which lowers the internal film temperature. Such lower internal film temperatures often result in decreased drug degradation and decreased loss of certain volatiles, such as flavors.

During film preparation, it may be desirable to dry films at high temperatures. High heat drying produces uniform films, and leads to greater efficiencies in film production. Films containing sensitive active components, however, may face degradation problems at high temperatures. Degradation is the "decomposition of a compound . . . exhibiting well-defined intermediate products." The American Heritage Dictionary of the English Language ($4^{th}$ ed. 2000). Degradation of an active component is typically undesirable as it may cause instability, inactivity, and/or decreased potency of the active component. For instance, if the active component is a drug or bioactive material, this may adversely affect the safety or efficacy of the final pharmaceutical product. Additionally, highly volatile materials will tend to be quickly released from this film upon exposure to conventional drying methods.

Degradation of an active component may occur through a variety of processes, such as, hydrolysis, oxidation, and light degradation, depending upon the particular active component. Moreover, temperature has a significant effect on the rate of such reactions. The rate of degradation typically doubles for every 10° C. increase in temperature. Therefore, it is commonly understood that exposing an active component to high temperatures will initiate and/or accelerate undesirable degradation reactions.

Proteins are one category of useful active ingredients that will degrade, denature, or otherwise become inactive when they are exposed to high temperatures for extended periods of time. Proteins serve a variety of functions in the body such as enzymes, structural elements, hormones and immunoglobulins. Examples of proteins include enzymes such as pancreatin, trypsin, pancrelipase, chymotrypsin, hyaluronidase, sutilains, streptokinaw, urokinase, altiplase, papain, bromelainsdiastase, structural elements such as collagen and albumin, hormones such as thyroliberin, gonadoliberin, adrenocorticottropin, corticotrophin, cosyntropin, sometrem, somatropion, prolactin, thyrotropin, somatostatin, vasopres sin, felypressin, lypressin, insulin, glucagons, gastrin, pentagastrin, secretin, cholecystokinin-pancreozymin, and immunomodulators which may include polysaccharides in addition to glycoproteins including cytokines which are useful for the inhibition and prevention of malignant cell growth such as tumor growth. A suitable method for the production of some useful glycoproteins is disclosed in U.S. Pat. No. 6,281,337 to Cannon-Carlson, et al., which in incorporated herein in its entirety.

Temperatures that approach 100° C. will generally cause degradation of proteins as well as nucleic acids. For example some glycoproteins will degrade if exposed to a temperature of 70° C. for thirty minutes. Proteins from bovine extract are also known to degrade at such low temperatures. DNA also begins to denature at this temperature.

Applicants have discovered, however, that the films of the present invention may be exposed to high temperatures during the drying process without concern for degradation, loss of activity or excessive evaporation due to the inventive process for film preparation and forming. In particular, the films may be exposed to temperatures that would typically lead to degradation, denaturization, or inactivity of the active component, without causing such problems. According to the present invention, the manner of drying may be controlled to prevent deleterious levels of heat from reaching the active component.

As discussed herein, the flowable mixture is prepared to be uniform in content in accordance with the teachings of the present invention. Uniformity must be maintained as the flowable mass was formed into a film and dried. During the drying process of the present invention, several factors produce uniformity within the film while maintaining the active component at a safe temperature, i.e., below its degradation temperature. First, the films of the present invention have an extremely short heat history, usually only on the order of minutes, so that total temperature exposure is minimized to the extent possible. The films are controllably dried to prevent aggregation and migration of components, as well as preventing heat build up within. Desirably, the films are dried from the bottom. Controlled bottom drying, as described herein, prevents the formation of a polymer film, or skin, on the top surface of the film. As heat is conducted from the film bottom upward, liquid carrier, e.g., water, rises to the film surface. The absence of a surface skin permits rapid evaporation of the liquid carrier as the temperature increases, and thus, concurrent evaporative cooling of the film. Due to the short heat exposure and evaporative cooling, the film components such as drag or volatile actives remain unaffected by high temperatures. In contrast, skinning on the top surface traps liquid carrier molecules of increased energy within the film, thereby causing the temperature within the film to rise and exposing active components to high, potentially deleterious temperatures.

Second, thermal mixing occurs within the film due to bottom heating and absence of surface skinning. Thermal mixing occurs via convection currents in the film. As heat is applied to the bottom of the film, the liquid near the bottom increases in temperature, expands, and becomes less dense. As such, this hotter liquid rises and cooler liquid takes its place. While rising, the hotter liquid mixes with the cooler liquid and shares thermal energy with it, i.e., transfers heat. As the cycle repeats, thermal energy is spread throughout the film.

Robust thermal mixing achieved by the controlled drying process of the present invention produces uniform heat diffusion throughout the film. In the absence of such thermal mixing, "hot spots" may develop. Pockets of heat in the film result in the formation of particle aggregates or danger areas within the film and subsequent non-uniformity. The formation of such aggregates or agglomerations is undesirable because it leads to non-uniform films in which the active may be randomly distributed. Such uneven distribution may lead to large differences in the amount of active per film, which is problematic from a safety and efficacy perspective.

Furthermore, thermal mixing helps to maintain a lower overall temperature inside the film. Although the film surfaces may be exposed to a temperature above that at which the active component degrades, the film interior may not reach this temperature. Due to this temperature differential, the active does not degrade.

For instance, the films of the present invention desirably are dried for 10 minutes or less. Drying the films at 80° C. for 10 minutes produces a temperature differential of about 5° C. This means that after 10 minutes of drying, the temperature of the inside of the film is 5° C. less than the outside exposure temperature. In many cases, however, drying times of less than 10 minutes are sufficient, such as 4 to 6 minutes. Drying for 4 minutes may be accompanied by a temperature differential of about 30° C., and drying for 6 minutes may be accompanied by a differential of about 25° C. Due to such large temperature differentials, the films may be dried at efficient, high temperatures without causing heat sensitive actives to degrade.

Figure 7:
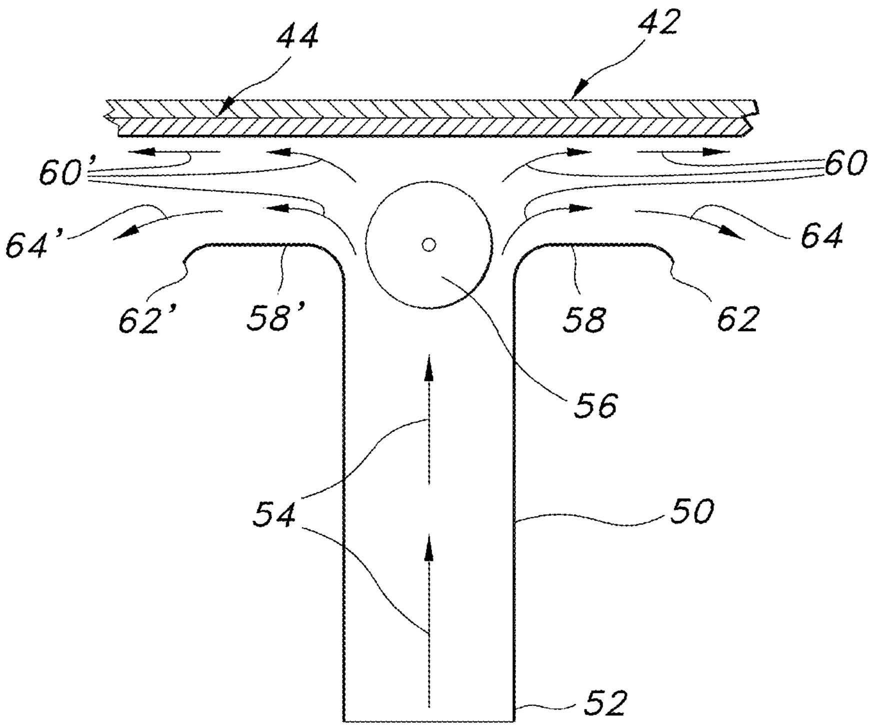
FIG. 7 is a schematic view of an apparatus suitable for drying the films of the present invention.
Figure 8:
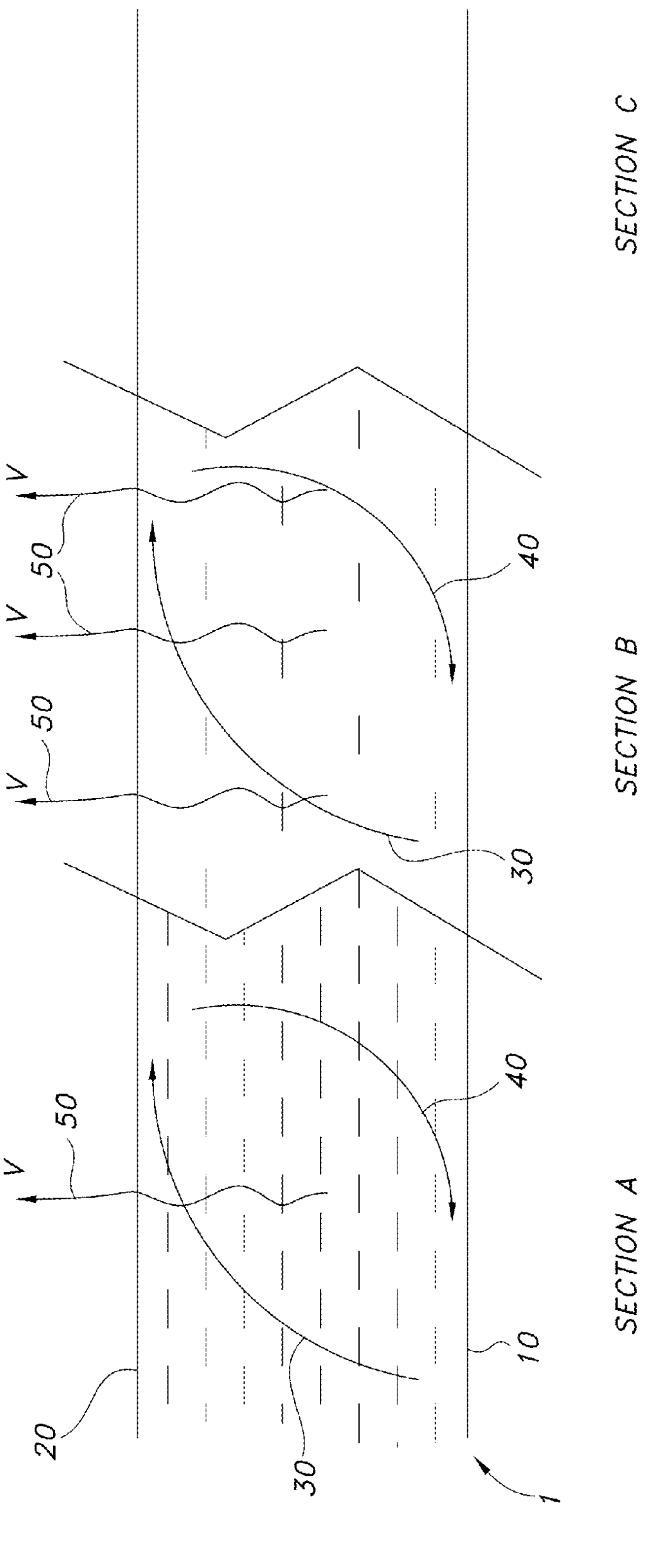
FIG. 8 is a sequential representation of the drying process of the present invention.
Figure 9:
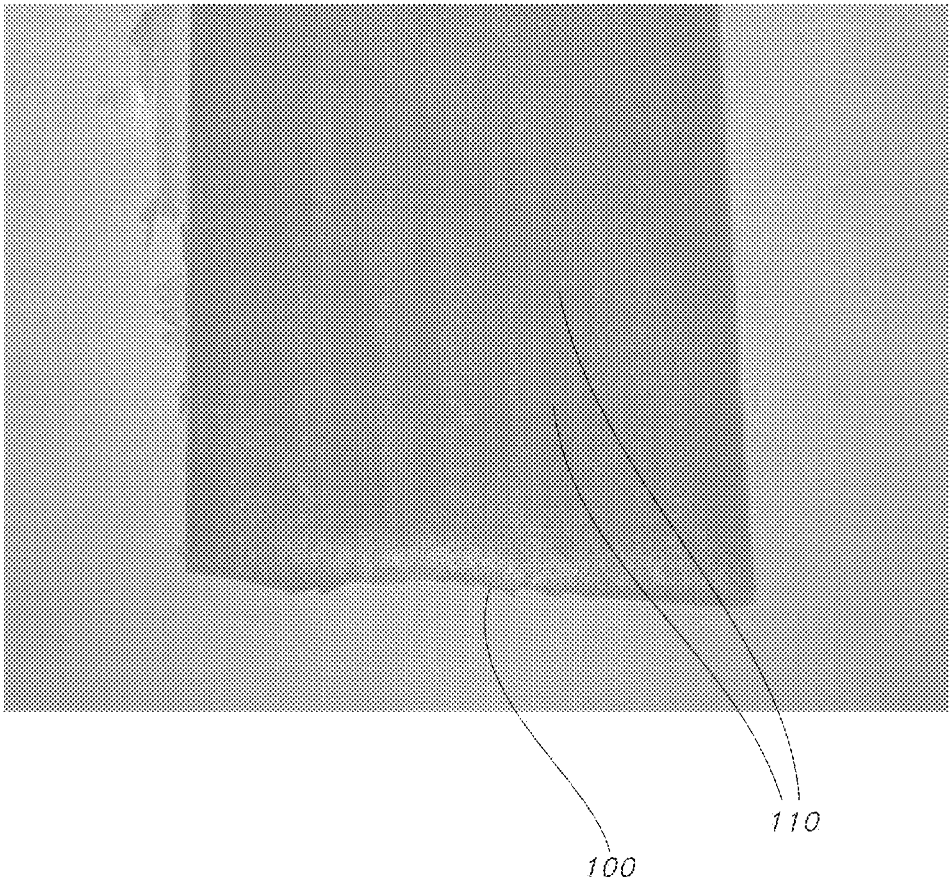
FIG. 9 is a photographic representation of a film dried by conventional drying processes.
Figure 10:
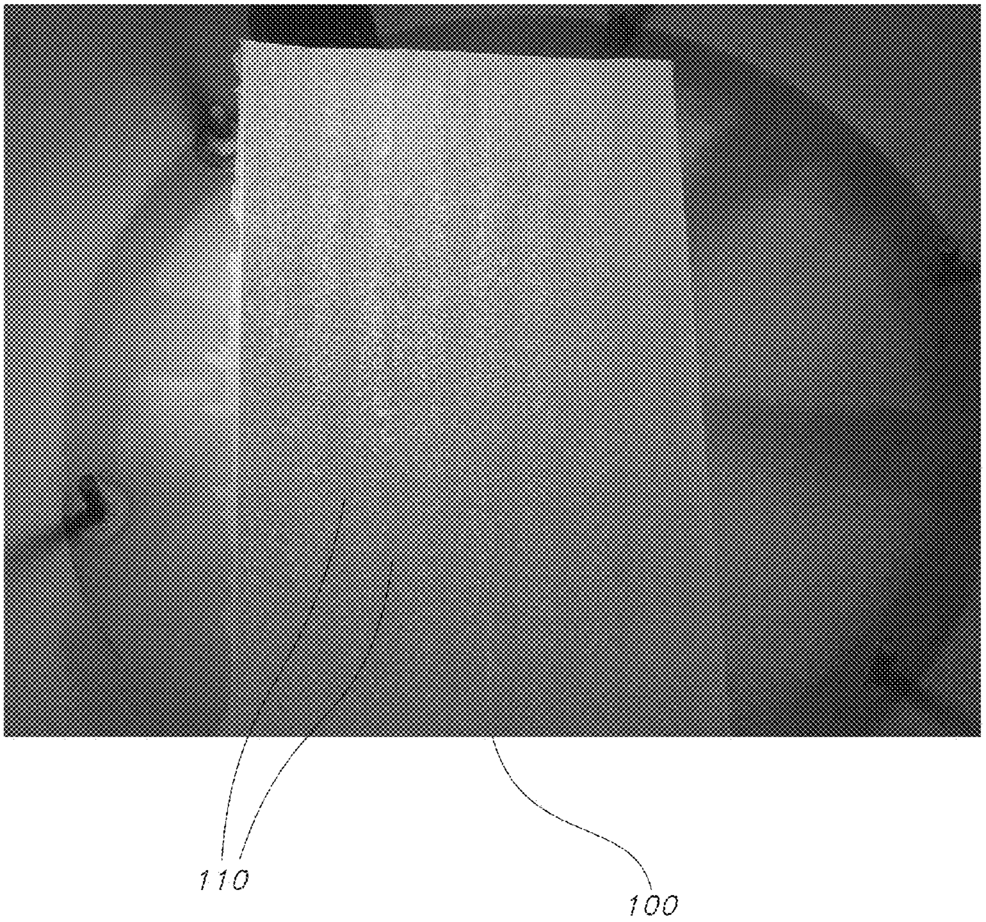
FIG. 10 is a photographic representation of a film dried by conventional drying processes.
Figure 11:
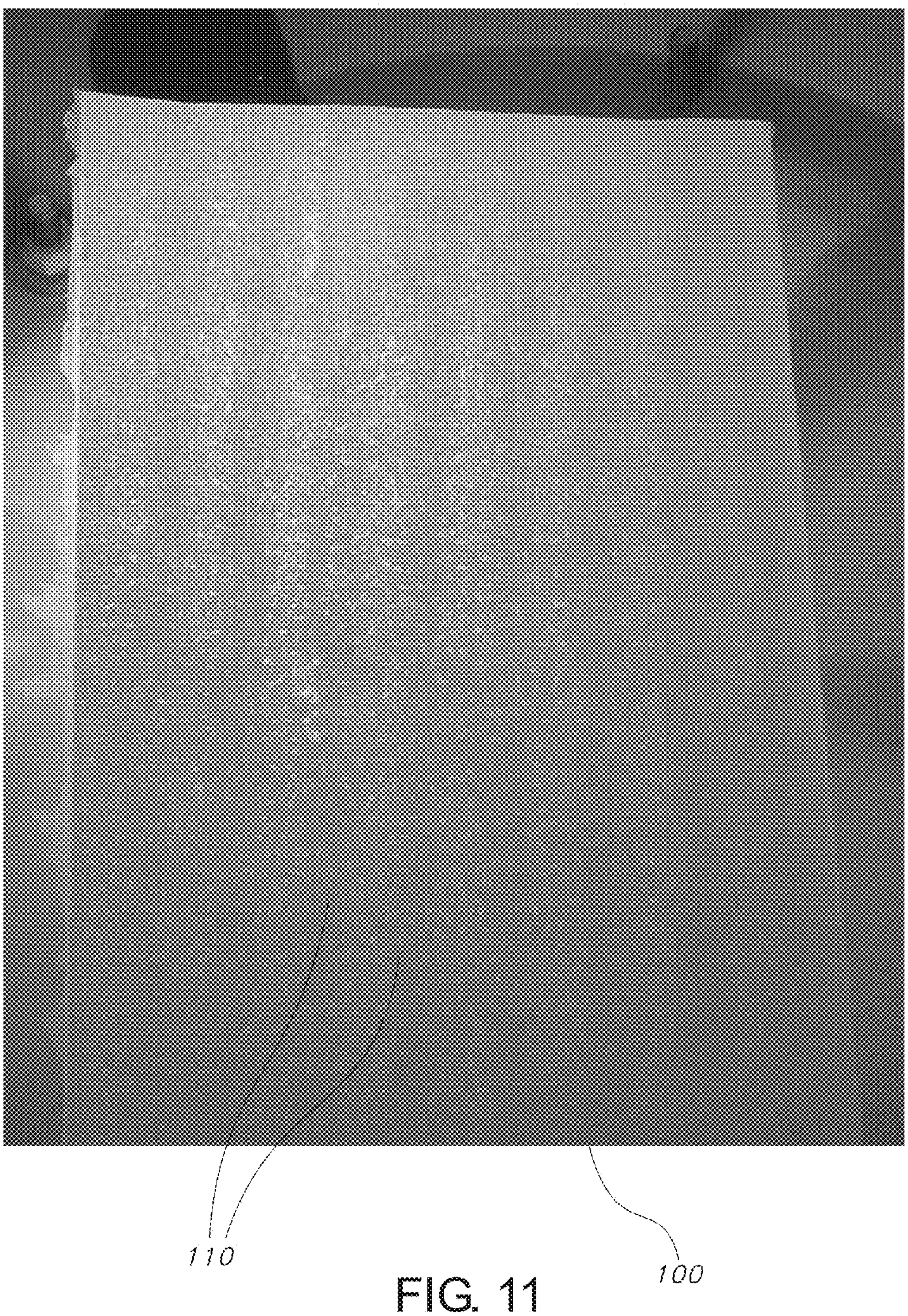
FIG. 11 is a photographic representation of a film dried by conventional drying processes.
Figure 12:
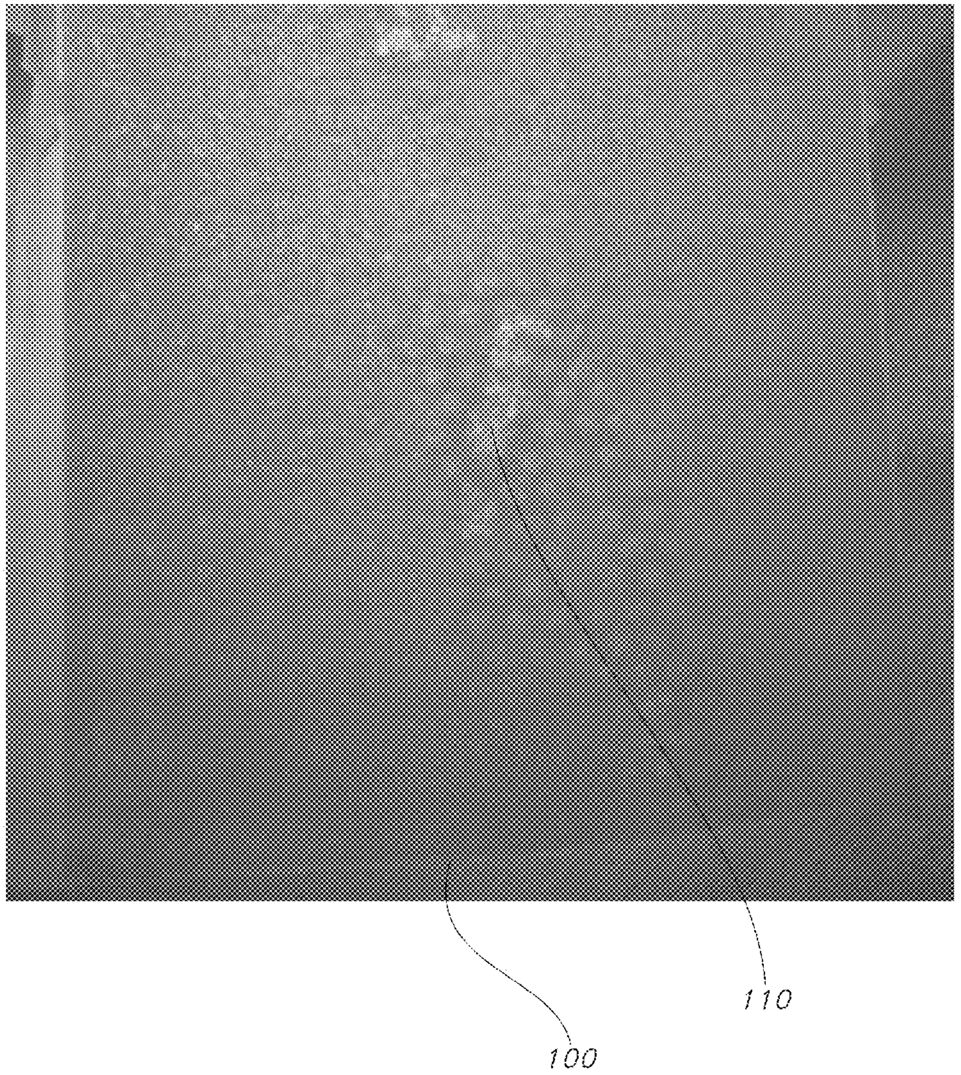
FIG. 12 is a photographic representation of a film dried by conventional drying processes.
Figure 13:
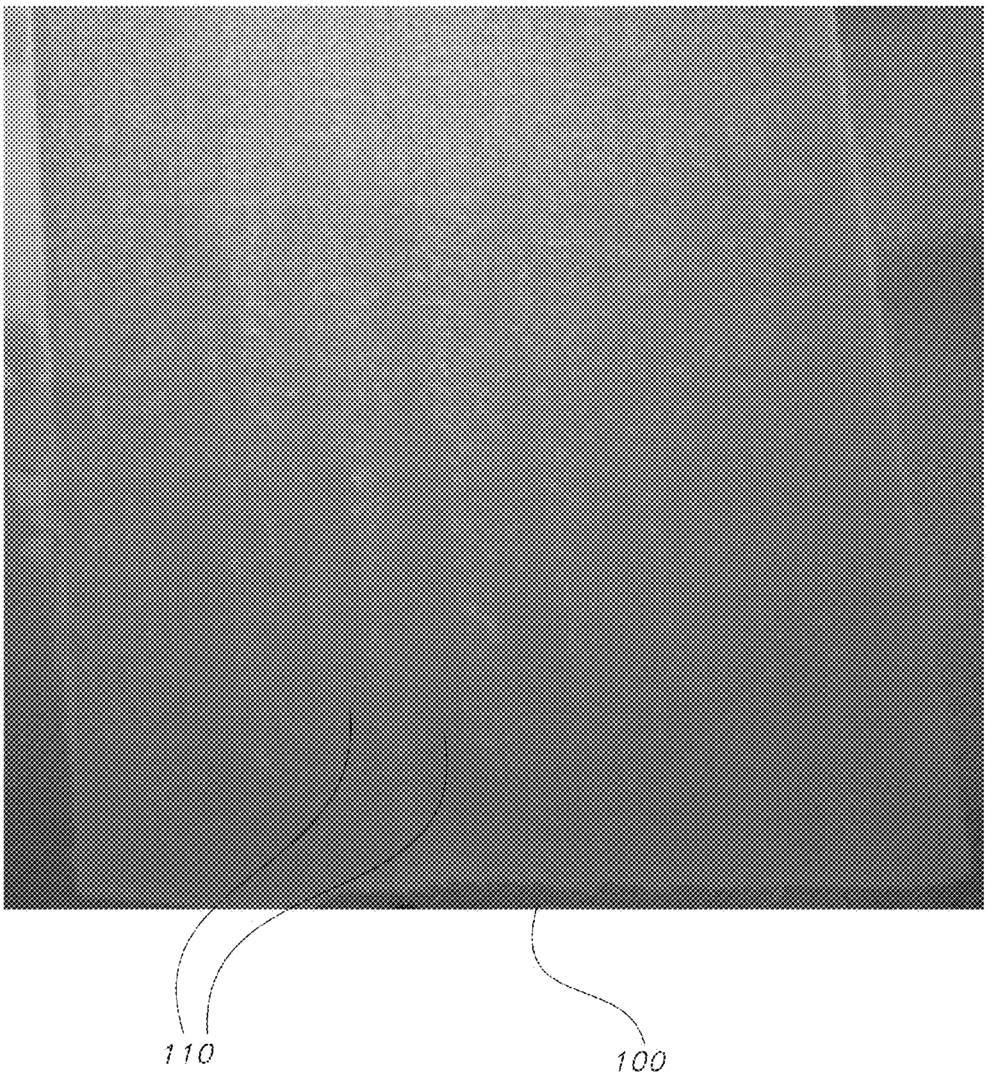
FIG. 13 is a photographic representation of a film dried by conventional drying processes.
Figure 14:
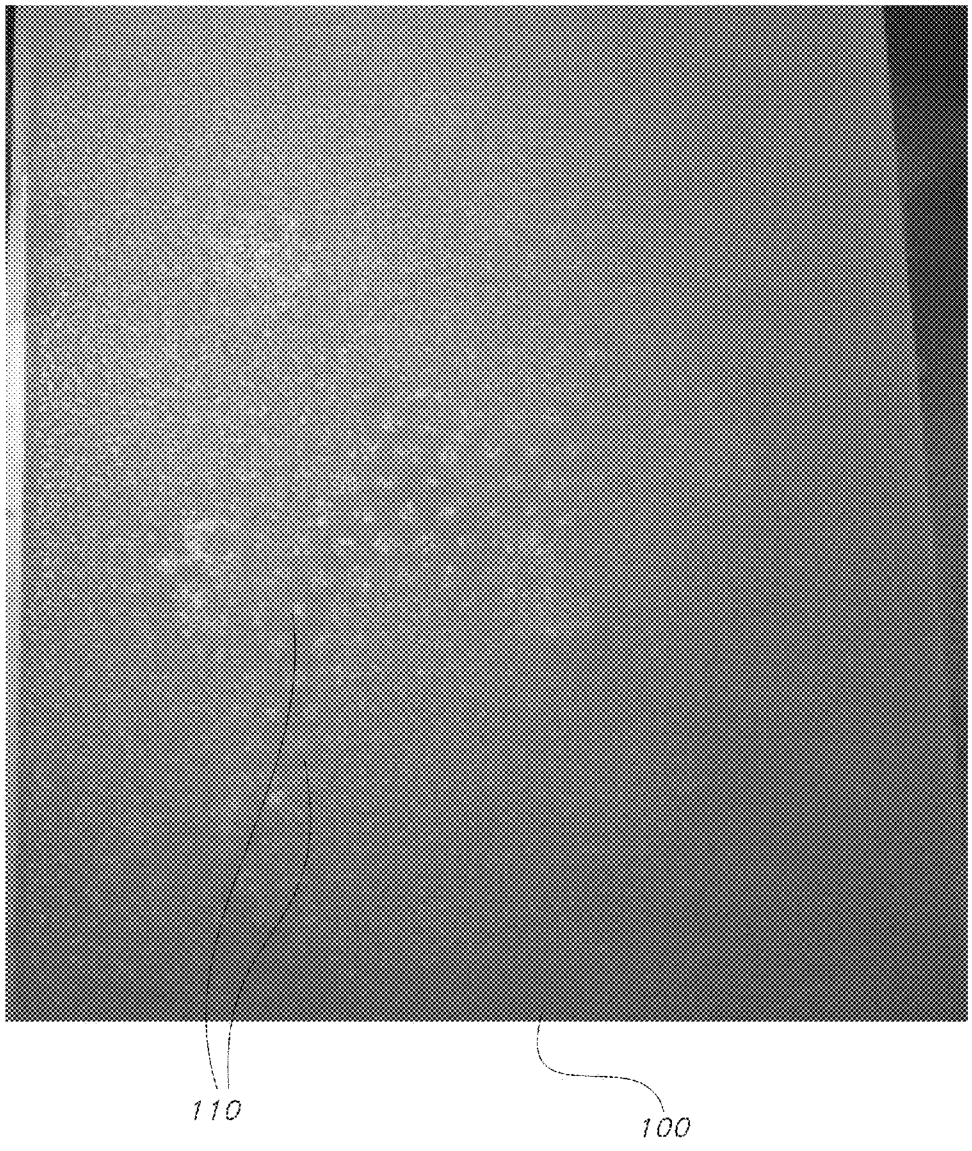
FIG. 14 is a photographic representation of a film dried by conventional drying processes.
Figure 15:
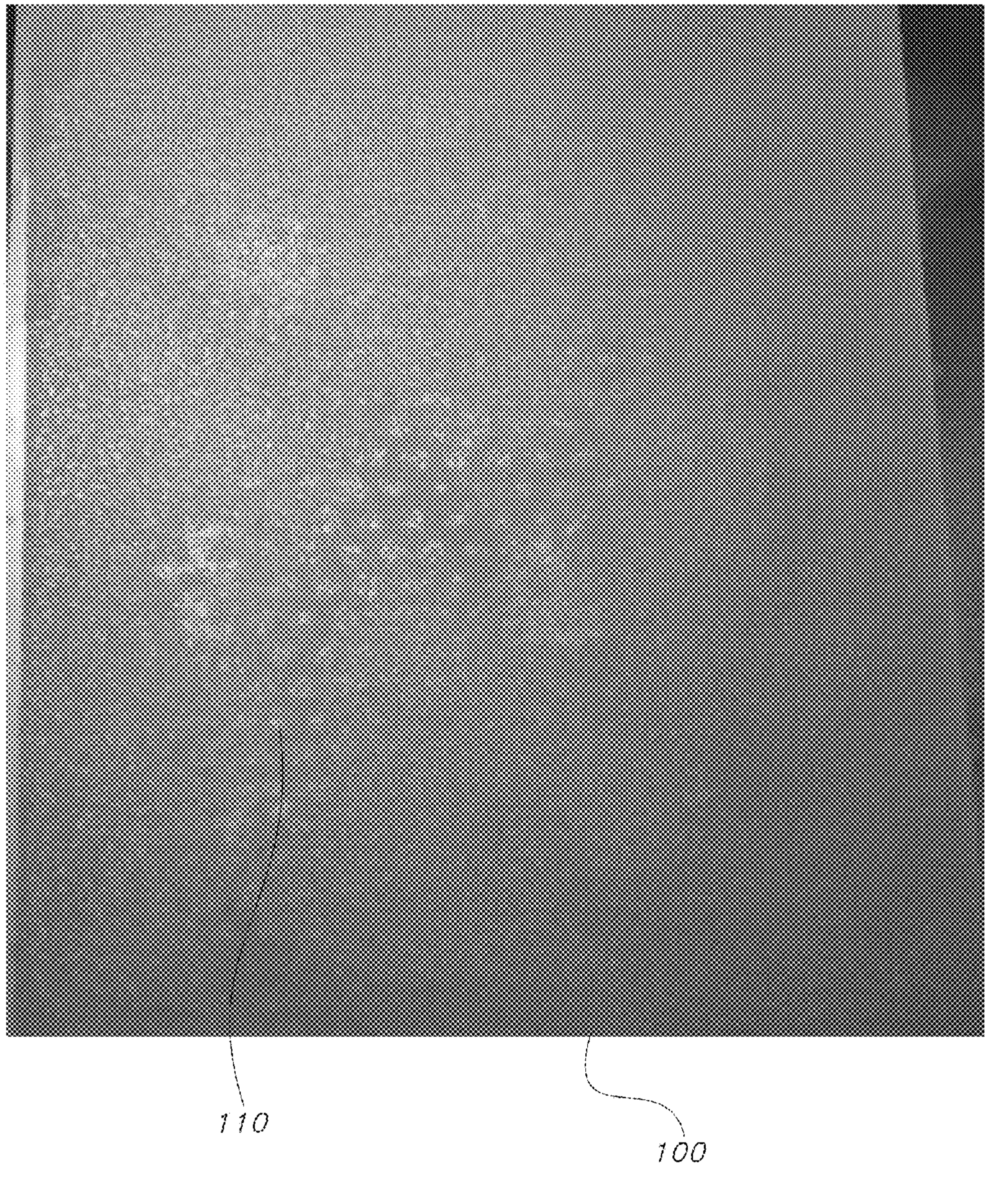
FIG. 15 is a photographic representation of a film dried by conventional drying processes.
Figure 16:
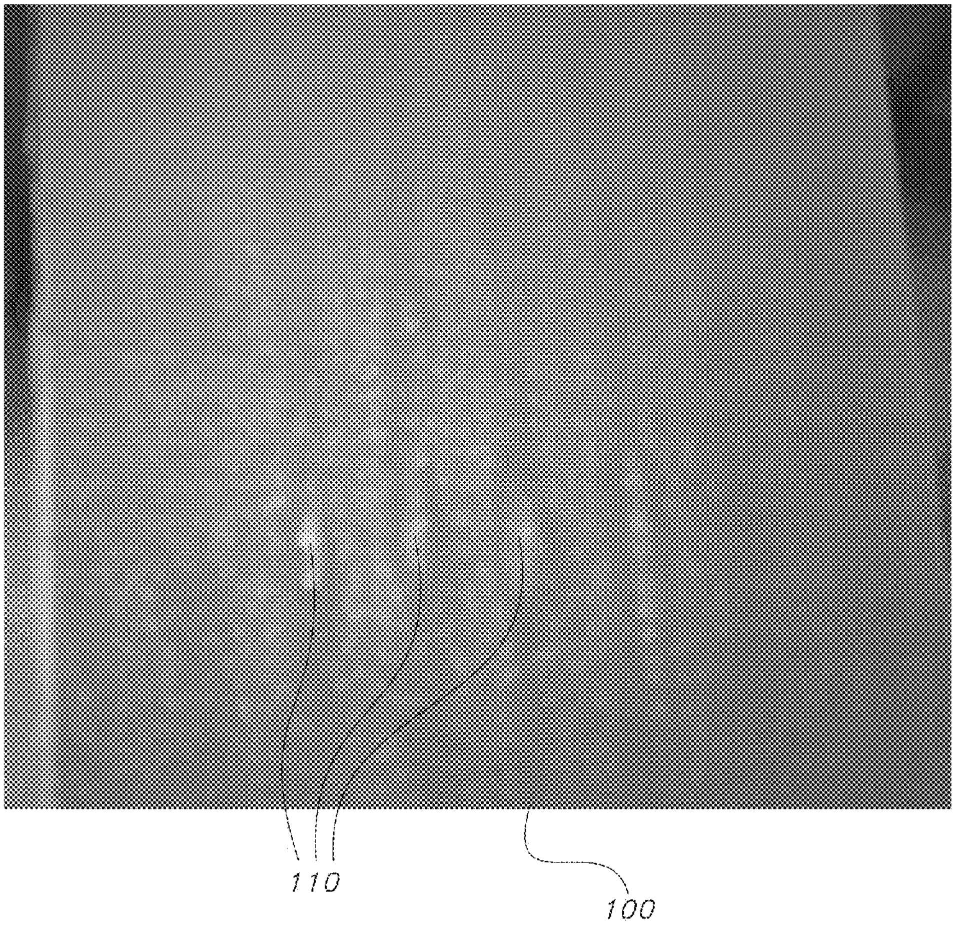
FIG. 16 is a photographic representation of a film dried by conventional drying processes.

FIG. 8 is a sequential representation of the drying process of the present invention. After mechanical mixing, the film may be placed on a conveyor for continued thermal mixing during the drying process. At the outset of the drying process, depicted in Section A, the film 1 preferably is heated from the bottom 10 as it is travels via conveyor (not shown). Heat may be supplied to the film by a heating mechanism, such as, but not limited to, the dryer depicted in FIG. 7. As the film is heated, the liquid carrier, or volatile ("V"), begins to evaporate, as shown by upward arrow 50. Thermal mixing also initiates as hotter liquid, depicted by arrow 30, rises and cooler liquid, depicted by arrow 40, takes its place. Because no skin forms on the top surface 20 of the film 1, as shown in Section B the volatile liquid continues to evaporate 50 and thermal mixing 30/40 continues to distribute thermal energy throughout the film. Once a sufficient amount of the volatile liquid has evaporated, thermal mixing has produced uniform heat diffusion throughout the film 1. The resulting dried film 1 is a visco-elastic solid, as depicted in Section C. The components desirably are locked into a uniform distribution throughout the film. Although minor amounts of liquid carrier, i.e., water, may remain subsequent to formation of the visco-elastic, the film may be dried further without movement of the particles, if desired.

Furthermore, particles or particulates may be added to the film-forming composition or matrix after the composition or matrix is cast into a film. For example, particles may be added to the film 42 prior to the drying of the film 42. Particles may be controllably metered to the film and disposed onto the film through a suitable technique, such as through the use of a doctor blade (not shown) which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent is a taste-masked or a controlled-release pharmaceutical agent. Useful organoleptic agents include flavors and sweeteners. Useful cosmetic agents include breath freshening or decongestant agents, such as menthol, including menthol crystals.

Although the inventive process is not limited to any particular apparatus for the above-described desirable drying, one particular useful drying apparatus 50 is depicted in FIG. 7. Drying apparatus 50 is a nozzle arrangement for directing hot fluid, such as but not limited to hot air, towards the bottom of the film 42 which is disposed on substrate 44. Hot air enters the entrance end 52 of the drying apparatus and travels vertically upward, as depicted by vectors 54, towards air deflector 56. The air deflector 56 redirects the air movement to minimize upward force on the film 42. As depicted in FIG. 7, the air is tangentially directed, as indicated by vectors 60 and 60', as the air passes by air deflector 56 and enters and travels through chamber portions 58 and 58' of the drying apparatus 50. With the hot air flow being substantially tangential to the film 42, lifting of the film as it is being dried is thereby minimized. While the air deflector 56 is depicted as a roller, other devices and geometries for deflecting air or hot fluid may suitable be used. Furthermore, the exit ends 62 and 62' of the drying apparatus 50 are flared downwardly. Such downward flaring provides a downward force or downward velocity vector, as indicated by vectors 64 and 64', which tend to provide a pulling or drag effect of the film 42 to prevent lifting of the film 42. Lifting of the film 42 may not only result in non-uniformity in the film or otherwise, but may also result in non-controlled processing of the film 42 as the film 42 and/or substrate 44 lift away from the processing equipment.

Monitoring and control of the thickness of the film also contributes to the production of a uniform film by providing a film of uniform thickness. The thickness of the film may be monitored with gauges such as Beta Gauges. A gauge may be coupled to another gauge at the end of the drying apparatus, i.e. drying oven or tunnel, to communicate through feedback loops to control and adjust the opening in the coating apparatus, resulting in control of uniform film thickness.

The film products are generally formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain the uniformity of the film, more specifically, a non-self-aggregating uniform heterogeneity. The resulting film will desirably contain less than about 10% by weight solvent, more desirably less than about 8% by weight solvent, even more desirably less than about 6% by weight solvent and most desirably less than about 2%. The solvent may be water, a polar organic solvent including, but not limited to, ethanol, isopropanol, acetone, methylene chloride, or any combination thereof.

In alternative embodiments, the film products of the present invention may be formed by extrusion rather than casting methods. Extrusion is particularly useful for film compositions containing polyethylene oxide-based polymer components, as discussed below. For instance, a single screw extrusion process may be employed in accordance with the present invention. According to such an extrusion process, pressure builds in the polymer melt so that it may be extruded through a die or injected into a mold.

Figure 37:
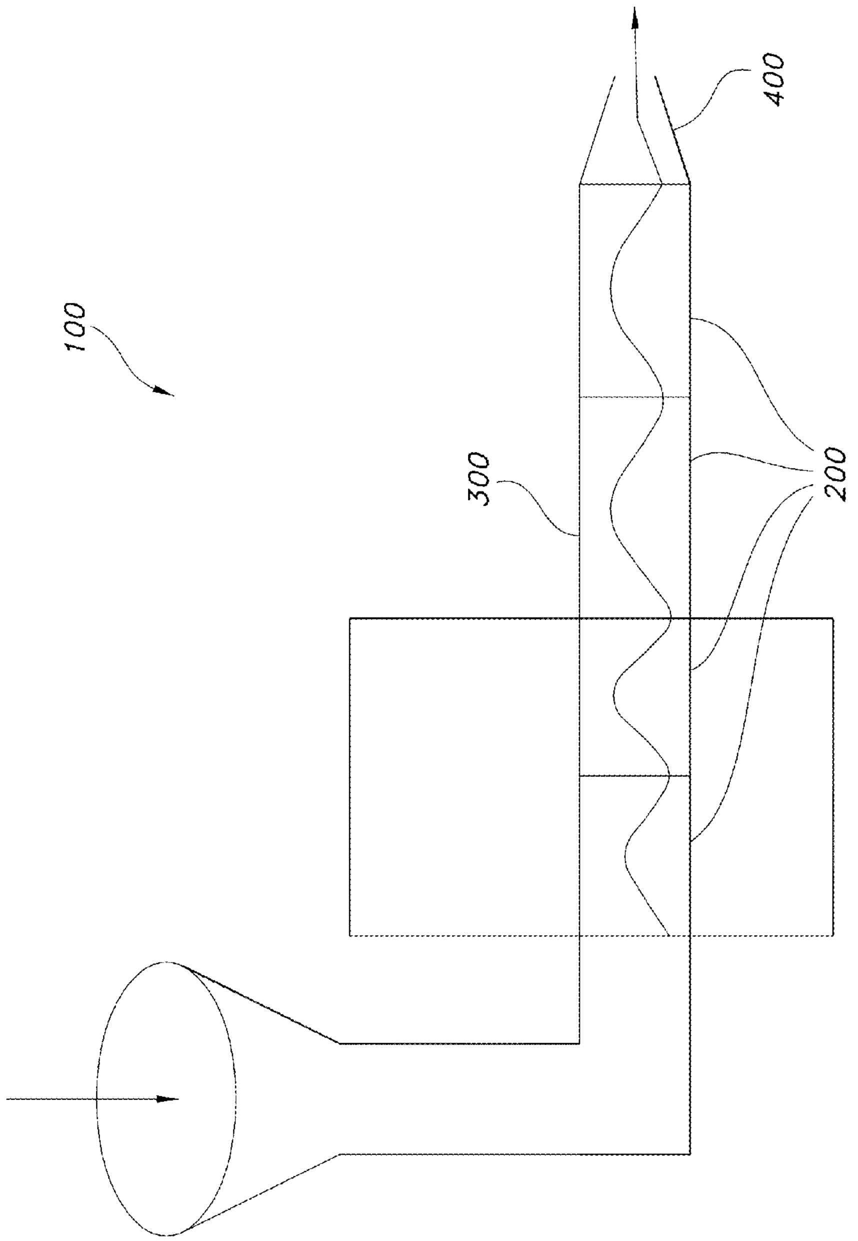
FIG. 37 is a schematic representation of a extrusion device for use in producing films of the present invention.

As further explanation, a single screw extruder for use in the process of the present invention may include a barrel 300 containing a number of zones 200, as shown in the extruder 100 depicted in FIG. 37. These zones 200 may have varying temperatures and pressures. For instance, it may be desirable for the zones to increase in temperature as the composition proceeds through the barrel 300 to the extrusion die 400. Any number of zones may be included in accordance with the present invention. In addition, the speed of extrusion may be controlled to produce desired film properties. For example, the extrusion composition may be held for an extended time period in the screw mixing chamber. Although this discussion is directed to single screw extrusion, other forms of extrusion are known to those skilled in the art and are considered well within the scope of the present invention.

Consideration of the above discussed parameters, such as but not limited to rheology properties, viscosity, mixing method, casting method and drying method, also impact material selection for the different components of the present invention. Furthermore, such consideration with proper material selection provides the compositions of the present invention, including a pharmaceutical and/or cosmetic dosage form or film product having no more than a 10% variance of a pharmaceutical and/or cosmetic active per unit area. In other words, the uniformity of the present invention is determined by the presence of no more than a 10% by weight of pharmaceutical and/or cosmetic variance throughout the matrix. Desirably, the variance is less than 5% by weight, less than 2% by weight, less than 1% by weight, or less than 0.5% by weight.

Film-Forming Polymers

The polymer may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Additionally, polyethylene oxide (PEO), when used alone or in combination with a hydrophilic cellulosic polymer, achieves flexible, strong films. Additional plasticizers or polyalcohols are not needed for flexibility. Non-limiting examples of suitable cellulosic polymers for combination with PEO include HPC and HPMC. PEO and HPC have essentially no gelation temperature, while HPMC has a gelation temperature of 58-64° C. (Methocel EF available from Dow Chemical Co.). Moreover, these films are sufficiently flexible even when substantially free of organic solvents, which may be removed without compromising film properties. As such, if there is no solvent present, then there is no plasticizer in the films. PEO based films also exhibit good resistance to tearing, little or no curling, and fast dissolution rates when the polymer component contains appropriate levels of PEO.

To achieve the desired film properties, the level and/or molecular weight of PEO in the polymer component may be varied. Modifying the PEO content affects properties such as tear resistance, dissolution rate, and adhesion tendencies. Thus, one method for controlling film properties is to modify the PEO content. For instance, in some embodiments rapid dissolving films are desirable. By modifying the content of the polymer component, the desired dissolution characteristics can be achieved.

In accordance with the present invention, PEO desirably ranges from about 20% to 100% by weight in the polymer component. In some embodiments, the amount of PEO desirably ranges from about 1 mg to about 200 mg. The hydrophilic cellulosic polymer ranges from about 0% to about 80% by weight, or in a ratio of up to about 4:1 with the PEO, and desirably in a ratio of about 1:1.

In some embodiments, it may be desirable to vary the PEO levels to promote certain film properties. To obtain films with high tear resistance and fast dissolution rates, levels of about 50% or greater of PEO in the polymer component are desirable. To achieve adhesion prevention, i.e., preventing the film from adhering to the roof of the mouth, PEO levels of about 20% to 75% are desirable. In some embodiments, however, adhesion to the roof of the mouth may be desired, such as for administration to animals or children. In such cases, higher levels of PEO may be employed. More specifically, structural integrity and dissolution of the film can be controlled such that the film can adhere to mucosa and be readily removed, or adhere more firmly and be difficult to remove, depending on the intended use.

The molecular weight of the PEO may also be varied. High molecular weight PEO, such as about 4 million, may be desired to increase mucoadhesivity of the film. More desirably, the molecular weight may range from about 100,000 to 900,000, more desirably from about 100,000 to 600,000, and most desirably from about 100,000 to 300,000. In some embodiments, it may be desirable to combine high molecular weight (600,000 to 900,000) with low molecular weight (100,000 to 300,000) PEOs in the polymer component.

For instance, certain film properties, such as fast dissolution rates and high tear resistance, may be attained by combining small amounts of high molecular weight PEOs with larger amounts of lower molecular weight PEOs. Desirably, such compositions contain about 60% or greater levels of the lower molecular weight PEO in the PEO-blend polymer component.

To balance the properties of adhesion prevention, fast dissolution rate, and good tear resistance, desirable film compositions may include about 50% to 75% low molecular weight PEO, optionally combined with a small amount of a higher molecular weight PEO, with the remainder of the polymer component containing a hydrophilic cellulosic polymer (HPC or HPMC).

Controlled Release Films

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the films of the present invention may also be chosen to allow for controlled disintegration of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

The actives employed in the present invention may be incorporated into the film compositions of the present invention in a controlled release form. For example, particles of drug may be coated with polymers such as ethyl cellulose or polymethacrylate, commercially available under brand names such as Aquacoat ECD and Eudragit E-100, respectively. Solutions of drug may also be absorbed on such polymer materials and incorporated into the inventive film compositions. Other components such as fats and waxes, as well as sweeteners and/or flavors may also be employed in such controlled release compositions.

The actives may be taste-masked prior to incorporation into the film composition, as set forth in co-pending PCT application titled, Uniform Films For Rapid Dissolve Dosage Form Incorporating Taste-Masking Compositions, (based on U.S. Provisional Application No. Express Mail Label No.: EU552991605 US of the same title, filed Sep. 27, 2003, attorney docket No. 1199-15P) the entire subject matter of which is incorporated by reference herein.

Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

The active components that may be incorporated into the films of the present invention include, without limitation pharmaceutical and cosmetic actives, drugs, medicaments, proteins, antigens or allergens such as ragweed pollen, spores, microorganisms, seeds, mouthwash components, flavors, fragrances, enzymes, preservatives, sweetening agents, colorants, spices, vitamins and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, uterine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relaten®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and $Ca^{H}$-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Clalis®, vardenafils, apomorphines, such as Uprima®, yohimbine hydrochlorides such as Aphrodyne®, and alprostadils such as Caverject®.

The popular $H_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono- or di-basic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

An anti-oxidant may also be added to the film to prevent the degradation of an active, especially where the active is photosensitive.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; Stevia Rebaudiana (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

When the active is combined with the polymer in the solvent, the type of matrix that is formed depends on the solubilities of the active and the polymer. If the active and/or polymer are soluble in the selected solvent, this may form a solution. However, if the components are not soluble, the matrix may be classified as an emulsion, a colloid, or a suspension.

Dosages

The film products of the present invention are capable of accommodating a wide range of amounts of the active ingredient. The films are capable of providing an accurate dosage amount (determined by the size of the film and concentration of the active in the original polymer/water combination) regardless of whether the required dosage is high or extremely low. Therefore, depending on the type of active or pharmaceutical composition that is incorporated into the film, the active amount may be as high as about 300 mg, desirably up to about 150 mg or as low as the microgram range, or any amount therebetween.

The film products and methods of the present invention are well suited for high potency, low dosage drugs. This is accomplished through the high degree of uniformity of the films. Therefore, low dosage drugs, particularly more potent racemic mixtures of actives are desirable.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser, and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

When dispersed in water, simethicone will spread across the surface, forming a thin film of low surface tension. In this way, simethicone reduces the surface tension of bubbles air located in the solution, such as foam bubbles, causing their collapse. The function of simethicone mimics the dual action of oil and alcohol in water. For example, in an oily solution any trapped air bubbles will ascend to the surface and dissipate more quickly and easily, because an oily liquid has a lighter density compared to a water solution. On the other hand, an alcohol/water mixture is known to lower water density as well as lower the water's surface tension. So, any air bubbles trapped inside this mixture solution will also be easily dissipated. Simethicone solution provides both of these advantages. It lowers the surface energy of any air bubbles that trapped inside the aqueous solution, as well as lowering the surface tension of the aqueous solution. As the result of this unique functionality, simethicone has an excellent anti-foaming property that can be used for physiological processes (anti-gas in stomach) as well as any for external processes that require the removal of air bubbles from a product.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Optional Components

A variety of other components and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; and inclusion compounds, such as cyclodextrins and caged molecules, which improve the solubility and/or stability of certain active components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It is further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin is one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ is yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, ethylcellulose, polyacrylamides, polyvinyloxoazolidone, and polyvinylalcohols.

Further potential additives include solubility enhancing agents, such as substances that form inclusion compounds with active components. Such agents may be useful in improving the properties of very insoluble and/or unstable actives. In general, these substances are doughnut-shaped molecules with hydrophobic internal cavities and hydrophilic exteriors. Insoluble and/or instable actives may fit within the hydrophobic cavity, thereby producing an inclusion complex, which is soluble in water. Accordingly, the formation of the inclusion complex permits very insoluble and/or instable actives to be dissolved in water. A particularly desirable example of such agents are cyclodextrins, which are cyclic carbohydrates derived from starch. Other similar substances, however, are considered well within the scope of the present invention.

Forming the Film

The films of the present invention must be formed into a sheet prior to drying. After the desired components are combined to form a multi-component matrix, including the polymer, water, and an active or other components as desired, the combination is formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it is desirable to select a method that will provide a flexible film, such as reverse roll coating. The flexibility of the film allows for the sheets of film to be rolled and transported for storage or prior to being cut into individual dosage forms. Desirably, the films will also be self-supporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. This procedure provides excellent control and uniformity of the resulting films, which is desired in the present invention. In this procedure, the coating material is measured onto the applicator roller by the precision setting of the gap between the upper metering roller and the application roller below it. The coating is transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller is wiped off by a doctor blade and the coating is then deposited onto the substrate as it passes between the engraved roller and a pressure roller.

Offset Gravure is common, where the coating is deposited on an intermediate roller before transfer to the substrate.

In the simple process of immersion or dip coating, the substrate is dipped into a bath of the coating, which is normally of a low viscosity to enable the coating to run back into the bath as the substrate emerges.

In the metering rod coating process, an excess of the coating is deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating is squeezed out by gravity or under pressure through a slot and onto the substrate. If the coating is 100% solids, the process is termed "Extrusion" and in this case, the line speed is frequently much faster than the speed of the extrusion. This enables coatings to be considerably thinner than the width of the slot.

It may be particularly desirable to employ extrusion methods for forming film compositions containing PEO polymer components. These compositions contain PEO or PEO blends in the polymer component, and may be essentially free of added plasticizers, and/or surfactants, and polyalcohols. The compositions may be extruded as a sheet at processing temperatures of less than about 90° C. Extrusion may proceed by squeezing the film composition through rollers or a die to obtain a uniform matrix. The extruded film composition then is cooled by any mechanism known to those of ordinary skill in the art. For example, chill rollers, air cooling beds, or water cooling beds may be employed. The cooling step is particularly desirable for these film compositions because PEO tends to hold heat.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

The drying step is also a contributing factor with regard to maintaining the uniformity of the film composition. A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well. With this method, although the components may aggregate, this will not result in the migration of the active to an adjacent dosage form, since each well may define the dosage unit per se.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film is dried from the bottom of the film to the top of the film. Desirably, substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This is accomplished by forming the film and placing it on the top side of a surface having top and bottom sides. Then, heat is initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried is about 100° C. or less, desirably about 90° C. or less, and most desirably about 80° C. or less.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film.

A specific example of an appropriate drying method is that disclosed by Magoon. Magoon is specifically directed toward a method of drying fruit pulp. However, the present inventors have adapted this process toward the preparation of thin films.

The method and apparatus of Magoon are based on an interesting property of water. Although water transmits energy by conduction and convection both within and to its surroundings, water only radiates energy within and to water. Therefore, the apparatus of Magoon includes a surface onto which the fruit pulp is placed that is transparent to infrared radiation. The underside of the surface is in contact with a temperature controlled water bath. The water bath temperature is desirably controlled at a temperature slightly below the boiling temperature of water. When the wet fruit pulp is placed on the surface of the apparatus, this creates a "refractance window." This means that infrared energy is permitted to radiate through the surface only to the area on the surface occupied by the fruit pulp, and only until the fruit pulp is dry. The apparatus of Magoon provides the films of the present invention with an efficient drying time reducing the instance of aggregation of the components of the film.

Another method of controlling the drying process involves a zone drying procedure. A zone drying apparatus may include a continuous belt drying tunnel having one or more drying zones located within. The conditions of each drying zone may vary, for example, temperature and humidity may be selectively chosen. It may be desirable to sequentially order the zones to provide a stepped up drying effect.

The speed of the zone drying conveyor desirably is continuous. Alternatively, the speed may be altered at a particular stage of the drying procedure to increase or decrease exposure of the film to the conditions of the desired zone. Whether continuous or modified, the zone drying dries the film without surface skinning.

Figure 35:
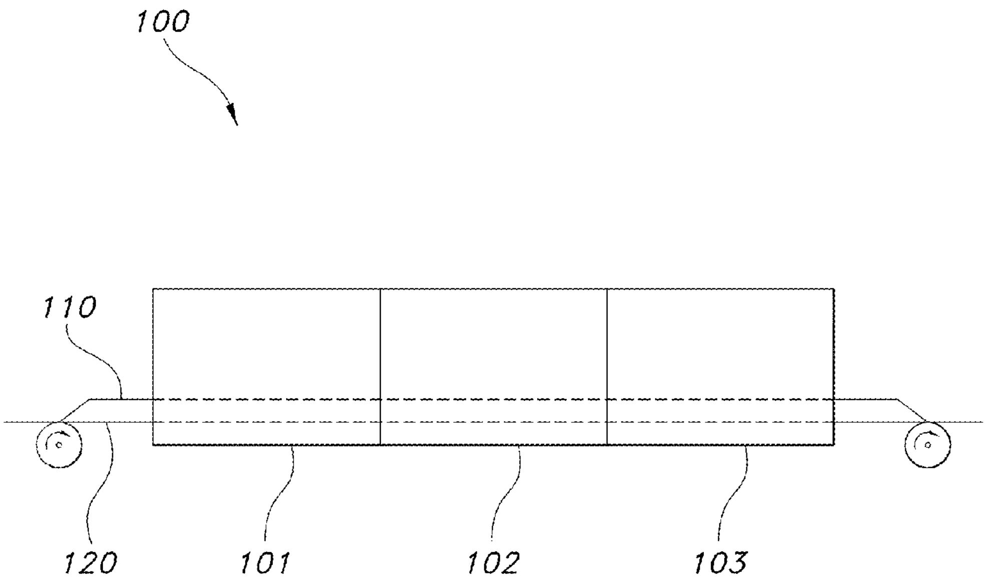
FIG. 35 is a schematic representation of a continuously-linked zone drying apparatus in accordance with the present invention.
Figure 36:
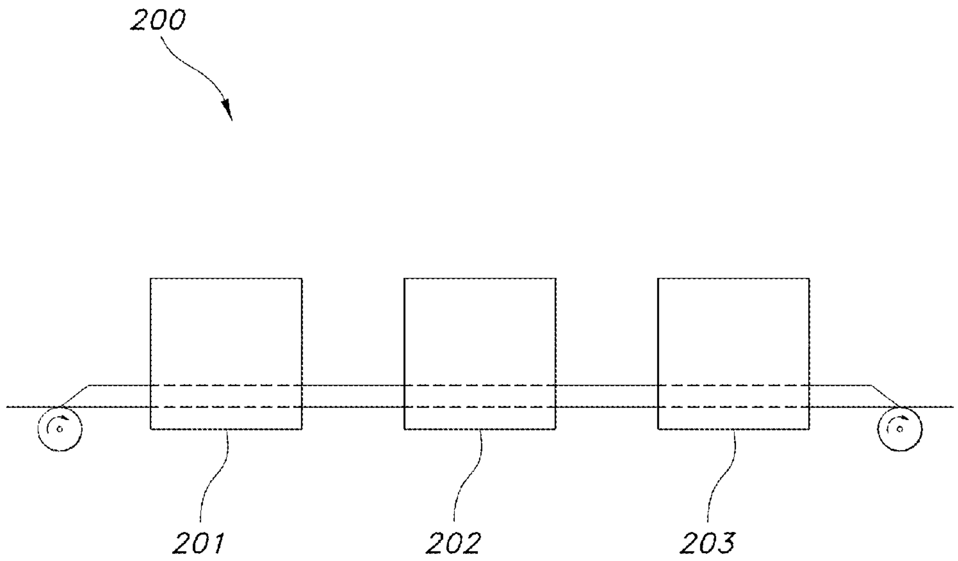
FIG. 36 is a schematic representation of a separate zone drying apparatus in accordance with the present invention.

According to an embodiment of the zone drying apparatus 100, shown in FIG. 35, the film 110 may be fed onto the continuous belt 120, which carries the film through the different drying zones. The first drying zone that the film travels through 101 may be a warm and humid zone. The second zone 102 may be hotter and drier, and the third zone 103 may also be hot and dry. These different zones may be continuous, or alternatively, they may be separated, as depicted by the zone drying apparatus 200 in FIG. 36. The zone drying apparatus, in accordance with the present invention, is not limited to three drying zones. The film may travel through lesser or additional drying zones of varying heat and humidity levels, if desired, to produce the controlled drying effect of the present invention.

To further control temperature and humidity, the drying zones may include additional atmospheric conditions, such as inert gases. The zone drying apparatus further may be adapted to include additional processes during the zone drying procedure, such as, for example, spraying and laminating processes, so long as controlled drying is maintained in accordance with the invention.

The films may initially have a thickness of about 500 μm to about 1,500 μm, or about 20 mils to about 60 mils, and when dried have a thickness from about 3 μm to about 250 μm, or about 0.1 mils to about 10 mils. Desirably, the dried films will have a thickness of about 2 mils to about 8 mils, and more desirably, from about 3 mils to about 6 mils.

Testing Films for Uniformity

It may be desirable to test the films of the present invention for chemical and physical uniformity during the film manufacturing process. In particular, samples of the film may be removed and tested for uniformity in film components between various samples. Film thickness and over all appearance may also be checked for uniformity. Uniform films are desired, particularly for films containing pharmaceutical active components for safety and efficacy reasons.

A method for testing uniformity in accordance with the present invention includes conveying a film through a manufacturing process. This process may include subjecting the film to drying processes, dividing the film into individual dosage units, and/or packaging the dosages, among others. As the film is conveyed through the manufacturing process, for example on a conveyor belt apparatus, it is cut widthwise into at least one portion. The at least one portion has opposing ends that are separate from any other film portion. For instance, if the film is a roll, it may be cut into separate sub-rolls. Cutting the film may be accomplished by a variety of methods, such as with a knife, razor, laser, or any other suitable means for cutting a film.

The cut film then may be sampled by removing small pieces from each of the opposed ends of the portion(s), without disrupting the middle of the portion(s). Leaving the middle section intact permits the predominant portion of the film to proceed through the manufacturing process without interrupting the conformity of the film and creating sample-inducted gaps in the film. Accordingly, the concern of missing doses is alleviated as the film is further processed, e.g., packaged. Moreover, maintaining the completeness of cut portions or sub-rolls throughout the process will help to alleviate the possibility of interruptions in further film processing or packaging due to guilty control issues, for example, alarm stoppage due to notice of missing pieces.

After the end pieces, or sampling sections, are removed from the film portion(s), they may be tested for uniformity in the content of components between samples. Any conventional means for examining and testing the film pieces may be employed, such as, for example, visual inspection, use of analytical equipment, and any other suitable means known to those skilled in the art. If the testing results show non-uniformity between film samples, the manufacturing process may be altered. This can save time and expense because the process may be altered prior to completing an entire manufacturing run. For example, the drying conditions, mixing conditions, compositional components and/or film viscosity may be changed. Altering the drying conditions may involve changing the temperature, drying time, moisture level, and dryer positioning, among others.

Moreover, it may be desirable to repeat the steps of sampling and testing throughout the manufacturing process. Testing at multiple intervals may ensure that uniform film dosages are continuously produced. Alterations to the process can be implemented at any stage to minimize non-uniformity between samples.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces.

The films may be used to orally administer an active. This is accomplished by preparing the films as described above and introducing them to the oral cavity of a mammal. This film may be prepared and adhered to a second or support layer from which it is removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

Another use for the films of the present invention takes advantage of the films' tendency to dissolve quickly when introduce to a liquid. An active may be introduced to a liquid by preparing a film in accordance with the present invention, introducing it to a liquid, and allowing it to dissolve. This may be used either to prepare a liquid dosage form of an active, or to flavor a beverage.

Figure 2:
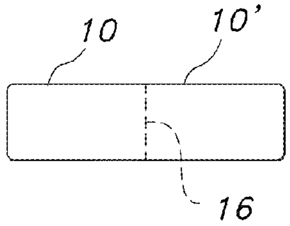
FIG. 2 shows a top view of two adjacently coupled packages containing individual unit dosage forms of the present invention, separated by a tearable perforation.
Figure 3:
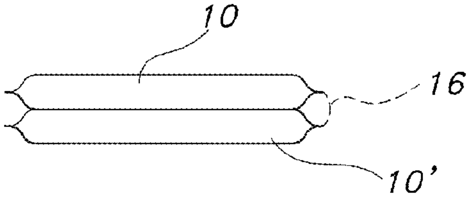
FIG. 3 shows a side view of the adjacently coupled packages of FIG. 2 arranged in a stacked configuration.
Figure 4:
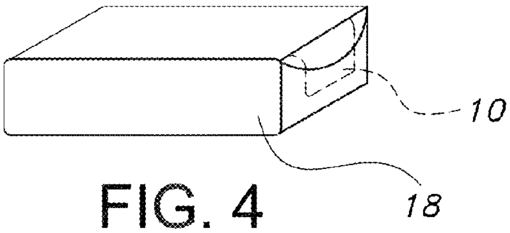
FIG. 4 shows a perspective view of a dispenser for dispensing the packaged unit dosage forms, dispenser containing the packaged unit dosage forms in a stacked configuration.
Figure 5:
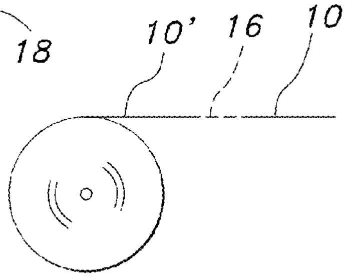
FIG. 5 is a schematic view of a roll of coupled unit dose packages of the present invention.

The films of the present invention are desirably packaged in sealed, air and moisture resistant packages to protect the active from exposure oxidation, hydrolysis, volatilization and interaction with the environment. Referring to FIG. 1, a packaged pharmaceutical dosage unit 10, includes each film 12 individually wrapped in a pouch or between foil and/or plastic laminate sheets 14. As depicted in FIG. 2, the pouches 10, 10' can be linked together with tearable or perforated joints 16. The pouches 10, 10' may be packaged in a roll as depicted in FIG. 5 or stacked as shown in FIG. 3 and sold in a dispenser 18 as shown in FIG. 4. The dispenser may contain a full supply of the medication typically prescribed for the intended therapy, but due to the thinness of the film and package, is smaller and more convenient than traditional bottles used for tablets, capsules and liquids. Moreover, the films of the present invention dissolve instantly upon contact with saliva or mucosal membrane areas, eliminating the need to wash the dose down with water.

Desirably, a series of such unit doses are packaged together in accordance with the prescribed regimen or treatment, e.g., a 10-90 day supply, depending on the particular therapy. The individual films can be packaged on a backing and peeled off for use.

The features and advantages of the present invention are more fully shown by the following examples which are provided for purposes of illustration, and are not to be construed as limiting the invention in any way.

EXAMPLES

Examples A-I

Water soluble thin film compositions of the present invention are prepared using the amounts described in Table 1.

TABLE 1

| | Weight (g) | | | | | | | | |
|---|---|---|---|---|---|---|---|---|---|
| Component | A | B | C | D | E | F | G | H | I |
| Hydroxypropylmethyl cellulose | | 1.76 | | 1.63 | 32.00 | | 3.67 | | 32.00 |
| Peppermint oil | | 0.90 | 1.0 | 1.05 | | 8.0 | 2.67 | | |
| Sweetener | 0.15 | 0.15 | 0.22 | 0.10 | | 4.6 | 1.53 | 0.15 | |
| Polyvinylpyrrolidone | | 0.94 | | 1.05 | | 7.0 | 2.33 | | |
| Tween 80[1] | 0.5 | 0.5 | 2.0 | 0.65 | 11.80 | | 1.35 | 0.5 | 11.80 |
| Simethicone[2] | 0.2 | 0.2 | 0.15 | 0.30 | 1.80 | | 0.21 | 0.2 | 1.80 |
| Listerine[3] | 83.35 | | | | | | | 83.35 | |
| Methylcellulose | 6.0 | | | | | | | | |
| Cornstarch[4] | | | 1.75 | | | | | | |
| Agar | | | 1.25 | | | | | | |
| Water | | 42.24 | 93.63 | 39.22 | 768.0 | 280.0 | 88.24 | | 768.0 |
| Loratadine[5] | | | | | 19.2 | | | | 19.2 |
| Pullulan[6] | | | | | | | | 6.0 | |
| Ibuprofen | | | | | | | | | 38.4 |

[1]Available from ICI Americas

[2]Available from OSI

[3]Available from Pfizer, Inc. including thymol (0.064%), eucalyptol (0.092%), methyl salicylate (0.060%), menthol (0.042%), water (up to 72.8%), alcohol (26.9%), benzoic acid, poloxamer 407, sodium benzoate, and caramel color

[4]Available from Grain Processing Corporation as Pure Cote B792

[5]Available from Schering Corporation as Claritin

[6]Available from Hayashibara Biochemical Laboratories, Inc., Japan

The ingredients of inventive compositions A-I were combined by mixing until a uniform mixture was achieved. The compositions were then formed into a film by reverse roll coating. These films were then dried on the top side of an infrared transparent surface, the bottom side of which was in contact with a heated water bath at approximately 99° C. No external thermal air currents were present above the film. The films were dried to less than about 6% by weight water in about 4 to 6 minutes. The films were flexible, self-supporting and provided a uniform distribution of the components within the film.

The uniform distribution of the components within the film was apparent by examination by either the naked eye or under slight magnification. By viewing the films it was apparent that they were substantially free of aggregation, i.e. the carrier and the actives remained substantially in place and did not move substantially from one portion of the film to another. Therefore, there was substantially no disparity among the amount of active found in any portion of the film.

Uniformity was also measured by first cutting the film into individual dosage forms. Twenty-five dosage forms of substantially identical size were cut from the film of inventive composition (E) above from random locations throughout the film. Then eight of these dosage forms were randomly selected and additively weighed. The additive weights of eight randomly selected dosage forms, are as shown in Table 2 below:

TABLE 2

| | Additive Weight (g) | |
|---|---|---|
| Sample | Trial 1 | Trial 2 |
| 1 | 0.04 | 0.04 |
| 2 | 0.08 | 0.08 |
| 3 | 0.12 | 0.12 |
| 4 | 0.16 | 0.16 |
| 5 | 0.20 | 0.20 |
| 6 | 0.24 | 0.24 |
| 7 | 0.28 | 0.28 |
| 8 | 0.32 | 0.32 |

The individual dosages were consistently 0.04 gm, which shows that the distribution of the components within the film was consistent and uniform. This is based on the simple principal that each component has a unique density. Therefore, when the components of different densities are combined in a uniform manner in a film, as in the present invention, individual dosages forms from the same film of substantially equal dimensions, will contain the same mass.

An alternative method of determining the uniformity of the active is to cut the film into individual doses. The individual doses may then be dissolved and tested for the amount of active in films of particular size. This demonstrates that films of substantially similar size cut from different locations on the same film contain substantially the same amount of active.

When the films formed from inventive compositions A-H are placed on the tongue, they rapidly dissolve, releasing the active ingredient. Similarly, when they are placed in water, the films rapidly dissolve which provides a flavored drink when the active is chosen to be a flavoring.

Examples J-L

Thin films that have a controlled degradation time and include combinations of water soluble and water insoluble polymers and water soluble films that allow controlled release of an active are prepared using approximately the amounts described in Table 3.

TABLE 3

| | Weight (g) | | |
|---|---|---|---|
| Component | J | K | L |
| Hydroxypropylmethyl cellulose | | 1.0 | 1.0 |
| Tween 80[1] | 0.7 | 0.7 | 0.7 |
| Water | | | 5.0 |
| Aquacoat ECD[2] | 17.0 | 17.0 | 17.5 |
| Peppermint oil | 1.0 | 0.4 | 1.1 |

[1]Available from ICI Americas

[2]A 30% by weight aqueous dispersion of ethyl cellulose available from FMC

The components of inventive compositions J-L were combined and formed into films using the methods for preparing inventive compositions A-I above. These films were also flexible, self-supporting and provided a uniform distribution of active which permits accuracy in dosing.

The uniformity of the films prepared from inventive compositions J-L may also be tested by either visual means measuring the weights of individual dosage films, or by dissolving the films and testing for the amount of active as described above.

Examples M-O

An alternative method of preparing films which provides an accurate dosing may be used for any of inventive compositions A-I. The method begins with first combining the ingredients with mixing. The combination of ingredients is then divided among individual wells or molds. In such a method, aggregation of the components during drying is prevented by the individual wells.

TABLE 4

| Component | Weight % M | N | O |
|---|---|---|---|
| 5% Methylcellulose Solution[1] | 73.22 | 44.22 | 74.22 |
| Raspberry Flavor | 3.28 | 3.28 | 3.28 |
| Sweetener Blends | 1.07 | 1.07 | 1.07 |
| Tween-80[2] | 2.47 | 2.47 | 2.47 |
| Polyvinylpyrrolidone | 3.30 | 3.30 | 3.30 |
| Ethanol 95% | 8.24 | 8.24 | 8.24 |
| Propylene Glycol | 1.65 | 1.65 | 1.65 |
| Calcium Carbonate | 4.12 | 4.12 | 4.12 |
| Cornstarch[3] | 1.65 | 1.65 | 1.65 |
| Red Dye[4] | 1.00 | | |
| Corn Syrup[5] | | 30.00 | |

[1] Available from Dow Chemical Co. as Methocel K35
[2] Available from ICI Americas
[3] Available from Grain Processing Corporation as Pure Cote B792
[4] Available from McCormick
[5] Available from Bestfoods, Inc. as Karo Syrup The ingredients in the above Table 4 were combined and formed into a film by casting the combination of ingredients onto the glass surface and applying heat to the bottom side of the glass. This provided inventive compositions M-O.

The film of composition M was examined both prior to and after drying for variations in the shading provided by the red dye. The film was examined both under sunlight and by incandescent bulb light. No variations in shade or intensity of color were observed.

Further testing of the films of composition M included testing of absorption which is directly related to concentration. The film was cut into segments each measuring 1.0 in. by 0.75 in., which were consecutively assigned numbers. Approximately 40 mg of the scrap material from which the segments were cut was dissolved in about 10 ml of distilled water and then quantitatively transferred to a 25 ml volumetric flask and brought to volume. The solution was centrifuged and scanned at 3 nm intervals from 203-1200 nm. The frequency of maximum absorption was found to be 530 nm. The solution was then re-centrifuged at a higher RPM (for the same length of time) and re-scanned, which demonstrated no change in the % transmission or frequency.

Each of the segments were weighed to 0.1 mg and then dissolved in 10 ml distilled water and transferred quantitatively to a 25 ml volumetric flask and brought to volume with distilled water. Each segment solution was then centrifuged as above, and then scanned, at first from 203-1200 nm and later from only 500 nm to 550 nm at a 1 nm scanning speed. The value recorded was the % transmission at the lowest wave length, which was most frequently 530 nm.

The absorption values are shown in Table 5 below:

TABLE 5

| Segment | mg/% A |
|---|---|
| 1-2 | 1.717 |
| 3-4 | 1.700 |
| 5-6 | 1.774 |
| 7* | 1.701 |
| 9-10 | 1.721 |
| 11-12 | 1.729 |
| 13-14 | 1.725 |
| 15-16 | 1.713 |

*segment 8 was lost

The overall average absorption was 1.724. Of the 15 segments tested, the difference between the highest and lowest values was 0.073 units, or 4% based on the average. This shows excellent control over the uniformity of the dye within the composition because the absorption is directly proportional to the concentration of the dye within each segment.

The film of inventive composition N provided a very flexible film. This film was able to be stretched and exhibited a very high tensile strength.

After forming the film of inventive composition O, the film was removed from the glass by very rapidly stripping the length of the glass with a razor. This provided very tightly wound "toothpick-like" dosage forms. Each dosage form consistently weighed 0.02 g. This demonstrates the uniformity of the dosage forms as well as the superior self-supporting properties of the films.

Examples P-W

Compositions P-W were prepared to demonstrate the interaction among various conditions in production of films as they relate to the present invention. The ingredients in the below Table 6 were combined and formed into a film using the process parameters listed in Table 7 below, prepared in a 6 m drying tunnel designed to incorporate bottom drying of the films. Each of the examples shows the effect of different ingredient formulations and processing techniques on the resultant film products.

TABLE 6

| Component | Weight (g) P | Q | R | S | T | U | V | W |
|---|---|---|---|---|---|---|---|---|
| Hydroxy-propylmethyl cellulose | 320 | 320 | 320 | 320 | 320 | 320 | 345 | 345 |
| Water | 1440 | 1440 | 1440 | 1440 | | 1440 | 999 | 999 |
| Sweetener | | | | | | 60 | 60 | 45 |
| Mint Flavor | | | | | | 80 | 80 | |
| Propylene Glycol | 50 | 50 | 50 | 100 | 100 | 100 | 100 | 69.3 |
| Xanthan | 22 | | 11 | 11.23 | 10 | 10 | 10 | 6.9 |
| Water/Ethanol (60/40) | | | | | 1440 | | | |
| Orange Flavor | | | | | | | | 42 |

TABLE 7

| | Film Thickness (Micron) | Top[1] v (m/sec) | Bot.[1] v (m/sec) | T[1] (° C.) | Top[2] v (m/sec) | Bot.[2] v (m/sec) | T[2] (° C.) | Film Weight (g) | Coater Speed m/min | % Moisture |
|---|---|---|---|---|---|---|---|---|---|---|
| P1 | 100 | 0 | 22 | 75 | 0 | 23 | 60 | 109 | 5 | >20 |
| P2 | 350 | 0 | 22 | 75 | 0 | 23 | 60 | n/a | 5 | >20 |
| P3 | 350 | 0 | 40 | 75 | 0 | 40 | 60 | 161 | 3 | >20 |
| P4 | 350 | 0 | 40 | 75 | 0 | 40 | 75 | 191 | 3 | >20 |
| P5 | 350 | 10 | 40 | 75 | 10 | 40 | 75 | 253 | 3 | >20 |
| Q | 350 | 0 | 40 | 75 | 10 | 40 | 75 | n/a | 3 | >20 |
| R | 350 | 0 | 40 | 85 | 10 | 0 | 85 | | 2.5 | >20 |
| S1 | 250 | 0 | 40 | 100 | 0 | 40 | 90 | 163 | 1.5 | <5 |
| S2 | 300 | 0 | 40 | 100 | 0 | 40 | 90 | 193 | 1.5 | <5 |
| S3 | 350 | 0 | 40 | 100 | 0 | 40 | 90 | 225 | 1.5 | <5 |
| T1 | 250 | 0 | 40 | 100 | 0 | 40 | 90 | 64 | 1.5 | <5 |
| T2 | 350 | 0 | 40 | 100 | 0 | 40 | 90 | 83 | 1.5 | <5 |
| U1 | 300 | 0 | 40 | 100 | 0 | 40 | 90 | 208 | 1.5 | 20 |
| U2 | 250 | 0 | 40 | 100 | 0 | 40 | 90 | 177 | 1.5 | 20 |
| U3 | 300 | 0 | 40 | 100 | 0 | 40 | 90 | 212 | 1.3 | 20 |
| V1 | 300 | 0 | 40 | 100 | 0 | 40 | 90 | 237 | 1.3 | 20 |
| V2 | 300 | 0 | 40 | 100 | 0 | 40 | 100 | 242 | 1.3 | 20 |
| V3 | 300 | 0 | 40 | 100 | 0 | 40 | 100 | 221 | 1 | 6 |
| W1 | 300 | 0 | 40 | 93 | 0 | 40 | 90 | 220 | 1.3 | 5 |
| W2 | 250 | 0 | 40 | 90 | 0 | 40 | 90 | 199 | 1.3 | 5 |
| W3 | 200 | 0 | 40 | 90 | 0 | 40 | 90 | 169 | 1.3 | 5 |

[1]First Heater Section (3 m)
[2]Second Heater Section (3 m)

In Table 7, each of the process parameters contributes to different properties of the films. Film thickness refers to the distance between the blade and the roller in the reverse roll coating apparatus. Bottom velocity and top velocity refer to the speed of air current on the bottom and top sides of the film, respectively. The film weight is a measure of the weight of a circular section of the substrate and the film of 100 $cm^2$.

Compositions P-R show the effects of visco-elastic properties on the ability to coat the film composition mixture onto the substrate for film formation. Composition P displayed a stringy elastic property. The wet film would not stay level, the coating was uneven, and the film did not dry. In Composition Q, substantially the same formulation as P was used however the xanthan was not included. This product coated the substrate but would not stay level due to the change in the visco-elastic properties of the wet foam. Composition R was prepared using substantially the same formulation, but incorporated one-half of the amount of xanthan of Composition P. This formulation provided a composition that could be evenly coated. Compositions P-Q demonstrate the importance of proper formulation on the ability of the film matrix to conform to a particular coating technique.

The films produced from Composition S contained a large amount of air in the films. This is shown by the dried film thickness which was the same despite that variation in the coated thickness as in Table 7. Microscopic examination of the film revealed a large number of air bubbles in the film. In order to correct for the addition of air in the films, care must be taken in the mixing process to avoid air inclusion.

Composition T included a change in the solvent to 60/40 water ethanol. Composition T was stirred slowly for 45 min. to deaerate the mixture. The dried weight film products T1 and T2 were consistent with the increase in solids from T1 to T2. The films dried much faster with less than 5% moisture. With the particular combination of ingredients in Composition T, the substitution of part ethanol for part water allowed the film to dry more quickly. The elimination of air from the film as a result of the slow stifling also contributed to the uniformity of the final film product and the faster drying time.

Only water was used as a solvent in Composition U. The dried weight of the U1-U3 changed consistently in accordance with the change in coating thickness indicating that no air bubbles were present. However, these films contained 20% moisture upon exit from the oven, unlike the films of Composition T, which included part ethanol and dried completely.

The amount of solids was increased and the amount of water was decreased in Compositions V1 and V2. The dried weight was greater than U1-U3 due to the increase in solids, however the films still contained 20% moisture upon exit from the oven, similar to Composition U.

The coating line speed was reduced for Composition V3, to prevent premature drying of the exposed top film surface. This film product dried to 6% moisture.

While increasing the amount of solids improved the film weight, longer drying times were required. This was due to the surface of the film sealing preventing easy removal of the water. Therefore, for Compositions W1-W3, the temperature in the first 3 m section of the dryer was decreased. This prevented the premature drying of the top surface of the films. Even at greater film thicknesses, the films were dried to 5% moisture even at faster coater line speeds.

Examples X-AA

TABLE 8

| | Weight (g) | | | |
|---|---|---|---|---|
| Component | X | Y | Z | AA |
| Loratadine | 104.69 | | | |
| Zomig | | 52.35 | | |
| Paxil | | | 104.69 | |
| Hydroxypropyl methylcellulose | 320 | 320 | 320 | 150 |
| Sweetener blend | 60 | 60 | 60 | 0.4 |
| Simethicone | 1.5 | 1.5 | 1.5 | 1.5 |
| Propylene glycol | 100 | 100 | 100 | |
| Water | 1440 | 1440 | 1440 | 790 |
| Cream essence | | | | 0.4 |
| Polyvinyl pyrrolidinone | | | | 4 |
| Ethanol | | | | 40 |
| Cocoa | | | | 55.2 |
| Polyoxyl-40-stearate | | | | 7 |

Compositions X, Y and Z of Table 8 were taste mask coated using a Glatt coater and Eudragit E-100 polymethacrylate polymer as the coating. The coating was spray coated at a 20% level. Therefore 10 mg of drug 12.5 mg of the final dry product must be weighed.

The base formula which excluded the drug additive was mixed with care to not incorporate air. After initial mixing the formula was slowly mixed to deaerate over 30 min. During this time the drug was weighed and prepared for addition to the base mix.

For Composition X, the Loratadine (80% drug) was added slowly to the mix with stirring. After 5 min. of stifling, the total mix was added to the pan of a three roll coater set (reverse roll coater) at 30 micron coating thickness.

The process bottom temperature was set at 90° C. with no top heat or air, the bottom air velocity was set at 40 m/sec., and the line speed was set at 1.3 m/min. Total drying time for the film was 4.6 min.

The liquid was coated at 30 microns and dried in the oven in less than 5 min. The film was flexible and a 1"×0.75" piece weighed 70 mg and contained 10 mg of Loratadine.

The experiment was repeated for Compositions Y and Z, Zomig and Paxil, respectively. Both produced flexible films with the target weight of 70 mg containing 5 mg of Zomig and 70 mg containing 10 mg of Paxil, respectively.

The products were sweet without any noticeable drug after-taste.

The ingredients of Composition AA were mixed in order to reduce air captured in the fluid matrix. After mixing 45 g of loratadine coated at a 80% active level and 20% coating using Eudragit E-100, this mixture was added slowing with mixing until the drug was evenly dispersed, approximately 5 min. The liquid was then deposited into the 3 roll coater (reverse roll coater) and coated at 30 microns at a line speed of 1.3 m/min. The oven temperature was set at 90° C. to apply air and heat to the bottom only, with an air velocity set at 40 m/sec. The dried film was 0.005 inch. thick (5 mil) and was cut into 1 in.×0.75 in. pieces weighing 70 mg+/−0.7 mg, demonstrating the uniformity of the composition of the film. The film was flexible with 5% moisture, free of air bubbles, and had uniform drug distribution as seen under the light microscope, as well as shown by the substantially identical weight measurements of the film pieces.

Examples BA-BI

The incorporation of the anti-foaming/de-foaming agent (i.e., simethicone) provided a film that not only provided a uniform film that substantially reduced or eliminated air bubbles in the film product, but also provided other benefits. The films displayed more desirable organoleptic properties. The films had an improved texture that was less "paper-like" provided a better mouth-feel to the consumer.

The compositions in Table 9 were prepared (including the addition of simethicone in inventive compositions BA-BG) and mixed under vacuum to remove air bubbles.

The resultant uncut films of inventive compositions BA-BG exhibited uniformity in content particularly with respect to the insoluble active, as well as unit doses of ¾" by 1" by 5 mils cut therefrom. The inventive compositions also were observed to have a smooth surface, absent of air bubbles. The significantly higher amounts of simethicone present in inventive compositions BF-BG also provided a very uniform film, but not significantly improved from that of inventive compositions BA-BE.

By contrast, comparative examples BH-BI were observed to have a rougher surface, exhibiting the inclusion of air bubbles in the resultant film which provided a less uniform texture and distribution of the ingredients.

TABLE 9

| Component | BA | BB | BC | BD | BE | BF | BG | BH | BI |
|---|---|---|---|---|---|---|---|---|---|
| Hydroxypropylmethyl cellulose | 0 | 3.77 | 3.70 | 3.84 | 0 | 3.67 | 0 | 0 | 3.84 |
| Peppermint oil | 2.94 | 1.93 | 2.39 | 0 | 0 | 2.67 | 2.94 | 2.67 | 0 |
| Sweetener | 2.20 | 0.32 | 0.23 | 0 | 0.17 | 1.53 | 2.20 | 1.54 | 0 |
| Polyvinylpyrrolidone | 2.68 | 2.01 | 2.39 | 0 | 0 | 2.33 | 2.68 | 2.34 | 0 |
| Tween 80[1] | 2.24 | 1.07 | 1.48 | 1.42 | 0.55 | 1.35 | 2.24 | 0 | 1.42 |
| Simethicone[2] | 0.66 | 0.42 | 0.68 | 0.22 | 0.22 | 5.00 | 2.00 | 0 | 0 |
| Listerine[3] | 0 | 0 | 0 | 0 | 92.41 | 0 | 0 | 0 | 0 |
| Methylcellulose | 4.03 | 0 | 0 | 0 | 0 | 0 | 4.03 | 0 | 0 |
| Cornstarch[4] | 2.68 | 0 | 0 | 0 | 0 | 0 | 2.68 | 0 | 0 |
| Water | 73.53 | 90.47 | 89.14 | 92.22 | 0 | 83.45 | 72.19 | 93.46 | 92.44 |
| Loratadine[5] | 4.29 | 0 | 0 | 2.31 | 0 | 0 | 4.29 | 0 | 2.31 |
| Pullulan[6] | 0 | 0 | 0 | 0 | 6.65 | 0 | 0 | 0 | 0 |
| Calcium Carbonate | 1.43 | 0 | 0 | 0 | 0 | 0 | 1.43 | 0 | 0 |
| Xanthan Gum | 0.30 | 0 | 0 | 0 | 0 | 0 | 0.30 | 0 | 0 |
| Propylene Glycol | 3.02 | 0 | 0 | 0 | 0 | 0 | 3.02 | 0 | 0 |

[1]Available from ICI Americas

[2]Available from OSI

[3]Available from Pfizer, Inc. including thymol (0.064%), eucalyptol (0.092%), methyl salicylate (0.060%), menthol (0.042%), water (up to 72.8%), alcohol (26.9%), benzoic acid, poloxamer 407, sodium benzoate, and caramel color

[4]Available from Grain Processing Corporation as Pure Cote B792

[5]Available from Schering Corporation as Claritin

[6]Available from Hayashibara Biochemical Laboratories, Inc., Japan

Examples CA-CC

The following examples of the present invention describe films and film-forming compositions that use an ethoxylated caster oil as a surfactant, or alternatively are free of surfactants, plasticizers and/or polyalcohols. Desirably, the films or film-forming compositions of the present invention are essentially free of surfactants. Moreover, the films or film-forming compositions of the present invention are desirably formulated to be essentially free of surfactants. Furthermore, the films or film-forming compositions of the present invention are desirably formulated to be essentially free of plasticizers. Still furthermore, the films or film-forming compositions of the present invention are desirably formulated to be essentially free of polyalcohols. Moreover, the films or film-forming compositions of the present invention are desirably formulated to be essentially free of surfactants and plasticizers. Furthermore, the films or film-forming compositions of the present invention are desirably formulated to be essentially free of surfactants, plasticizers and polyalcohols.

TABLE 10

| Component | (parts by wt.) CA |
|---|---|
| POLYMERS: | |
| Hydroxypropylmethyl cellulose | 15.6 |
| Cornstarch[1] | 10.41 |
| Polyvinylpyrrolidone | 10.41 |
| Xanthan Gum | 1.14 |
| SURFACTANT[2]: | 2.0 |
| PLASTICIZER[3]: | 11.67 |
| ANTI-FOAM AGENT[4] | 2.44 |
| OTHER | |
| Spearmint Flavor | 10.43 |
| Loratadine (drug) | 16.62 |
| Calcium Carbonate | 5.54 |
| Sweetener | 9.36 |

[1]Available from Grain Processing Corporation as Pure Cote B792

[2]Ethoxylated caster oil, Cremophor ® EL available from BASF

[3]Propylene Glycol

[4]Silicone Emulsion

The above ingredients were added at 30% to 70% water and stirred until polymers were fully hydrated which took 45 min. The mix was then put under vacuum to eliminate entrapped air. Vacuum was added in a steady manner starting at 500 mm and progressing up to 760 mm over 45 min.

After release of the vacuum, 6 grams of the liquid was added to a coating paper using a 200 micron spiral wound rod and a K Control Coater Model 101 (RK Print Coat Inst. Ltd.). The paper substrate onto which the coating was added was a silicone coated paper. The coated paper was then dried at 90° C. until about 5% moisture remained. The formula coated and dried to a film thickness of approx. 60 microns and quickly dissolved in the mouth.

TABLE 11

| Component | (parts by wt.) CB |
|---|---|
| POLYMERS: | |
| Hydroxypropylmethyl cellulose | 15.6 |
| Cornstarch[1] | 10.41 |
| Polyvinylpyrrolidone | 10.41 |
| PLASTICIZER/SOLVENT[2]: | 22.1 |
| ANTI-FOAM AGENT[3] | 2.44 |
| OTHER | |
| Raspberry Flavor | 0.3 |
| Calcium Carbonate[4] | 30.38 |
| Sweetener | 8.36 |

[1]Available from Grain Processing Corporation as Pure Cote B792

[2]Propylene Glycol

[3]Polydimethyl Siloxane Emulsion

[4]Functioned to mimic drug loading

The above ingredients were added to water at 40% until a homogeneous suspension was made. Vacuum was added over 20 min. starting at 500 mm Hg. and ending at 660 mm Hg. until all air was removed from suspension. Film was made as described in prior experiments. The liquid coated the silicone release substrate and dried to a uniform flexible film. The film passed the 180° bend test without cracking and dissolved in the mouth.

TABLE 12

| Component | (parts by wt.) CC |
|---|---|
| POLYMERS: | |
| Hydroxypropylmethyl cellulose | 7.8 |
| Hydroxypropyl cellulose | 7.8 |
| ANTI-FOAM AGENT[1] | 0.75 |
| OTHER | |
| Peppermint & Bittermint Flavor | 2.25 |
| Tastemasking Flavor[2] | 0.3 |
| Calcium Carbonate[3] | 15.2 |
| Sweeteners | 0.9 |

[1]Polydimethyl Siloxane Emulsion

[2]Prosweet from Virginia Dare

[3]Functioned to mimic drug loading

The above ingredients were added at 30% to 70% water and stirred until polymers were fully hydrated which took 20 min. The mix was then put under vacuum to eliminate entrapped air. Vacuum was added in a steady manner up to 760 mm over 35 min.

After release of the vacuum, the liquid was added to a coating paper using a 350 micron smooth bar and a K Control Coater Model 101 (RK Print Coat Inst. Ltd.). The paper substrate onto which the coating was added was a silicone coated paper. The coated paper was then dried at 90° C. until about 4% moisture remained. The formula coated and dried to a film. The film had an acceptable taste and quickly dissolved in the mouth. The taste-masking flavor is an ingredient that affects the taste receptors to mask the receptors from registering a different, typical undesirable, taste. The film passed the 180° bend test without cracking and dissolved in the mouth.

Example CD

The following example of the present invention describes films and film-forming compositions that use a taste-masked, pharmaceutically active agent which also contains flavors and taste-masking aids. A taste-masking flavor is an ingredient that effects taste receptors to mask the receptors from registering a different, typically undesirable, taste.

TABLE 13

| Component | (grams) CD |
|---|---|
| Hydroxypropylmethyl cellulose | 4.26 |
| Hydroxypropyl cellulose | 1.42 |
| Precipitated calcium Carbonate | 1.22 |
| Sweetner[1] | 0.6 |
| Taste-Masking flavor[2] | 0.08 |
| Taste-masked Acetaminophen[3] | 5.86 |
| Cinnamon Flavor | 0.9 |
| Spearmint Flavor | 0.43 |
| Polydimethylsiloxane emulsion | 0.23 |

[1]Sucralose, available from McNeil Nutritionals

[2]Magna Sweet, available from Mafco Worldwide Corp.

[3]Gutte Enteric, coated acetaminophen, Gatte, LLC

The above ingredients, except for the pharmaceutically active agent and flavors, were added at 35 grams water and stirred until polymers were fully hydrated which took about 20 min. Food coloring (7 drops of red food coloring and 1 drop of yellow fool coloring) was also added. The mix was then put under vacuum to eliminate entrapped air. Vacuum was added in a steady manner starting at 500 mm and progressing up to 760 mm over about 10 to 20 minutes. The taste-masked Acetaminophen was added to the mix in about 4 minutes was stifling under vacuum. The flavors were then added to the mix in about 4 minutes was stifling under vacuum.

After release of the vacuum, the liquid solution was added to a coating paper using a 350 micron smooth bar. The paper substrate onto which the coating was added was a silicone coated paper. The coated paper was then dried at 90° C. for about 11 minutes until about 3% moisture remained.

The formula coated and dried to a film. The film had an acceptable taste and moderately quickly dissolved in the mouth. The film did not curl on standing. The film passed the 180° bend test without cracking and dissolved in the mouth.

Examples CE-CF

Thin film compositions of the present invention were prepared using the amounts described in Table 14.

TABLE 14

| Component | Weight (g) |
|---|---|
| Hydroxypropylmethyl cellulose | 3.92 |
| Pullulan | 3.92 |
| Trehalose[1] | 3.5 |
| Precipitated Calcium Carbonate | 3.85 |
| Propylene Glycol | 1.96 |
| Simethicone[2] | 0.35 |
| Bovine Extract[3] | 32.5 |
| Water | q.s. |

[1]Available from Cargill Inc.
[2]Available from Sentry
[3]Available from Amarillo Biosciences Inc.

The above ingredients were combined by mixing until a uniform mixture was achieved. A sufficient amount of water was present in the film compositions prior to drying, i.e., q.s., which may range between about 200 g to about 1000 g. The bovine extract protein contained in the compositions is a heat sensitive protein. After mixing, the compositions were cast into films on release paper using a K-Control Coater with a 250 micron smooth bar.

Figure 32:
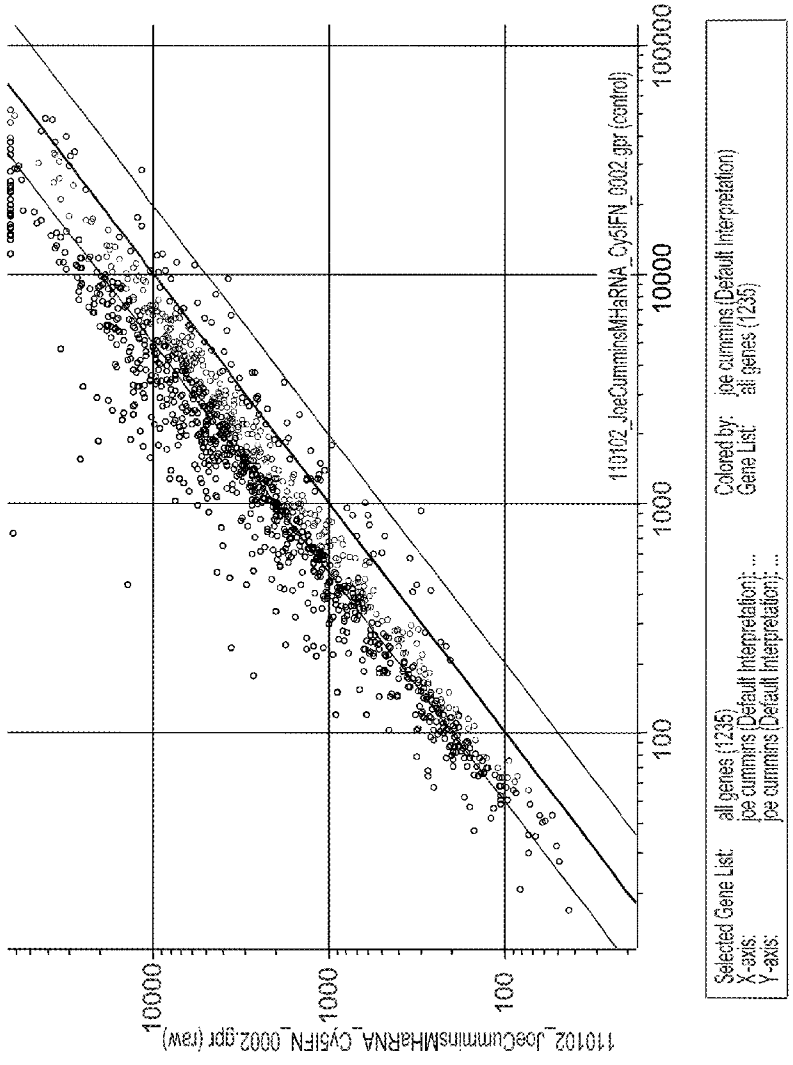
FIG. 32 is a graphical representation of a microarray on the blood of a human after ingestion by the human of a film of the present invention containing a bovine derived protein.

In Example CE, the films subsequently were dried in an oven at approximately 80° C. for about 6 minutes. The films were dried to about 4.3 percent moisture. In Example CF, the films were dried in an oven at approximately 60° C. for about 10 minutes. The films were dried to about 5.06 percent moisture. After drying, the protein derived from bovine extract, which was contained in the films, was tested to determine whether or not it remained substantially active. To test the activity, a film dosage unit of this example was administered to a human. After ingesting the dosage, a microarray on the human's blood was conducted. The results, listed in Appendix A which is incorporated by reference herein, and graphically represented in FIG. 32, demonstrate that the protein was approximately 100 percent active in the final, dried film products of both Examples CE and CF. Therefore, the heat sensitive active did not substantially degrade or denaturize during the drying process.

Example CG

Thin film compositions of the present invention were prepared using the amounts described in Table 15.

TABLE 15

| Component | Weight (g unless otherwise indicated) CG | CH |
|---|---|---|
| Hydroxypropylmethyl cellulose | 4.59 | 9.18 |
| Hydroxypropyl cellulose | 1.53 | 3.06 |
| Sucralose[1] | 0.7 | 1.4 |
| Magna Sweet[2] | 0.09 | 0.18 |
| Precipitated calcium carbonate | 2.0 | 4 |
| Fat-coated dextromethorphan hydrobromide | 5.96 | 11.93 |
| Orange concentrate flavor | 1.05 | 2.1 |
| Prosweet MM24[3] | 0.18 | 0.35 |
| Propylene glycol | 1.22 | 2.45 |
| Simethicone[4] | 0.18 | 0.35 |
| Water | 32.5 | 65 |
| Red food color | | 4 drops |
| Yellow food color | | 6 drops |

[1]Available from McNeil Nutritional
[2]Taste-masking flavor, available from Mafco Worldwide Corp.
[3]Taste-masking flavor, available from Virginia Dare
[4]Available from Sentry The above ingredients in the amounts listed for CG were combined by mixing, and then cast into two films on release paper using a K-Control Coater with a 350 micron smooth bar. The films were subsequently dried according to conventional drying techniques, rather than via the uniform drying process of the present invention. One film was dried in an oven at 80° C. for 9 minutes on a wire rack. The second film was dried in an oven at 80° C. for 9 minutes on a wire screen. Both films were dried to about 2.4 percent moisture.

The resulting dried films showed imprints of the wire rack and screen after drying. These configurations comprise imprints of wire supports typically used in the drying process. Without uniform heat diffusion, the wire supports conducted heat more intensely at the points of contact with the substrate, leading to increased evaporation at these points. This caused more vigorous mixing, thereby pulling more particles to the contact points. The result is increased particle density seen as aggregations at the contact points.

The solution was cast into two more films on release paper using the K-Control Coater with a 350 micron smooth bar. These films were dried by the process of the present invention, under the same time and temperature conditions as above. In particular, the films were dried in an 80° C. air oven for 9 minutes on trays lined with furnace filters, which uniformly disperse heat. The films were dried to about 1.89 percent moisture. The resulting films had no streaks, and were homogenous. Due to uniform heat diffusion throughout the film, no particle aggregations developed.

Example CH

Figure 17:
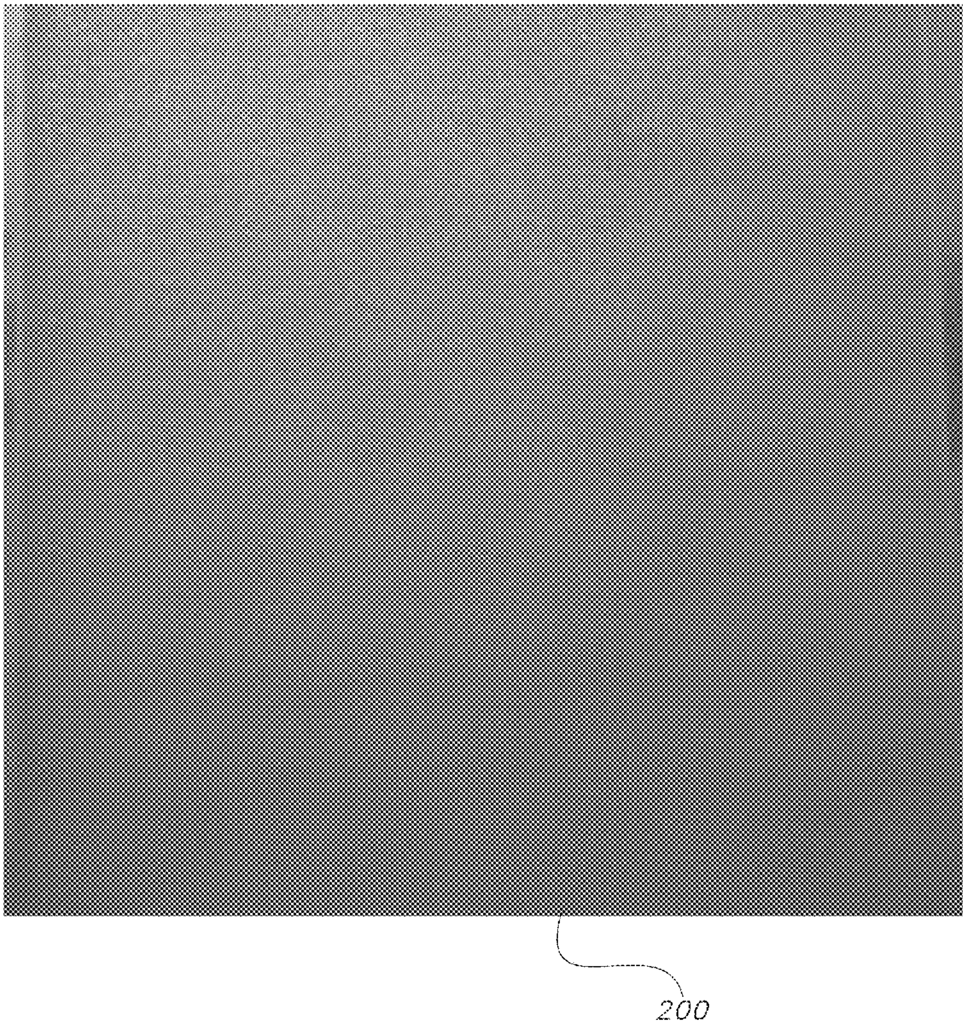
FIG. 17 is a photographic representation of a film dried by the inventive drying process.
Figure 18:
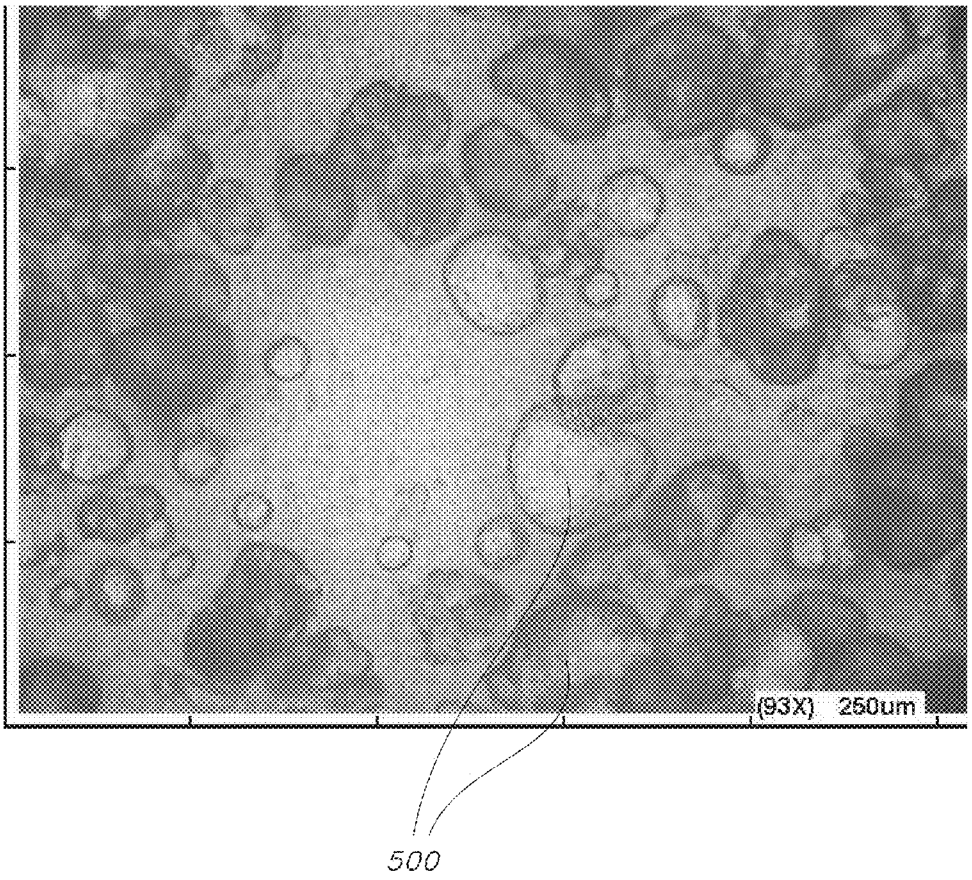
FIG. 18 is a photomicrographic representation of a film containing fat coated particles dried by the inventive drying process.
Figure 19:
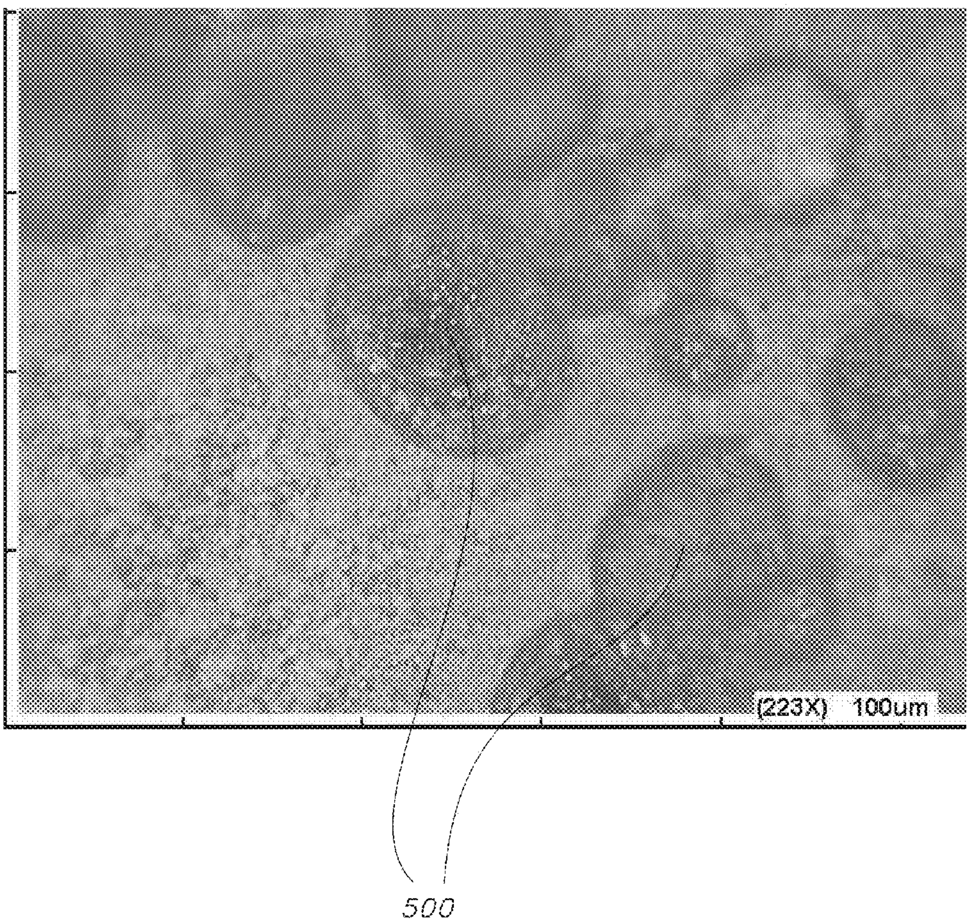
FIG. 19 is a photomicrographic representation of a film containing fat coated particles dried by the inventive drying process.
Figure 20:
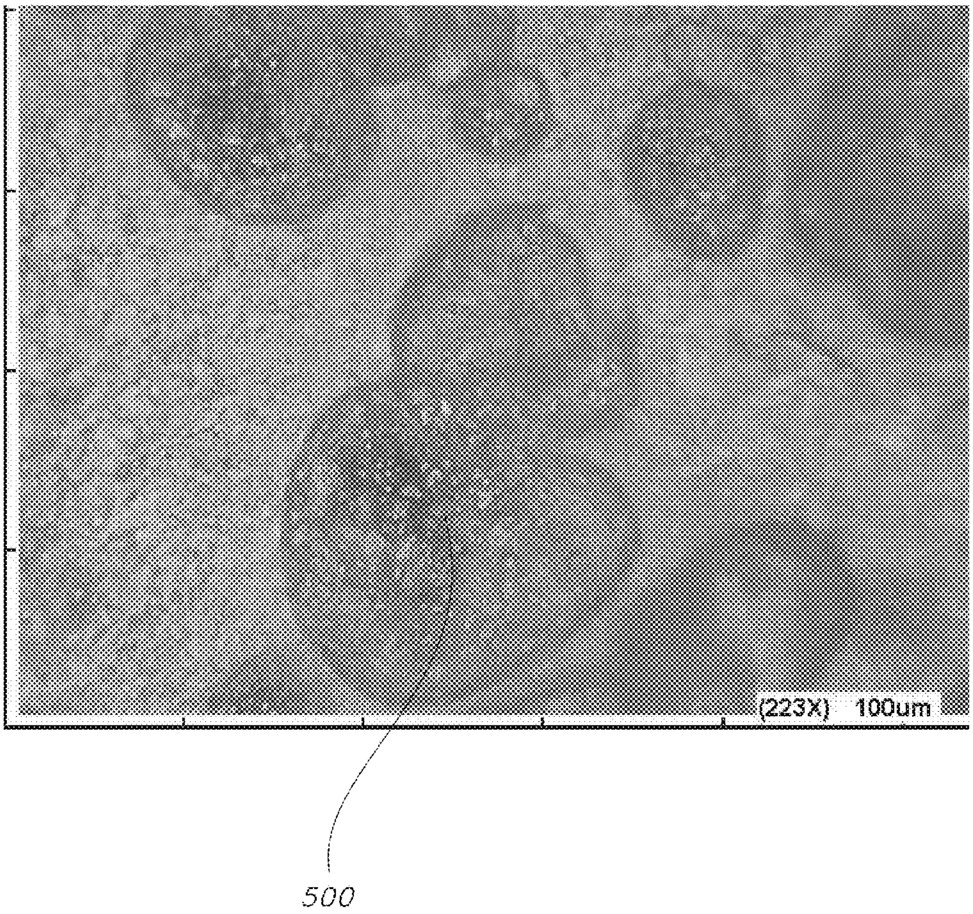
FIG. 20 is a photomicrographic representation of a film containing fat coated particles dried by the inventive drying process.
Figure 21:
FIG. 21 is a photomicrographic representation of a film containing fat coated particles dried by the inventive drying process.
Figure 22:
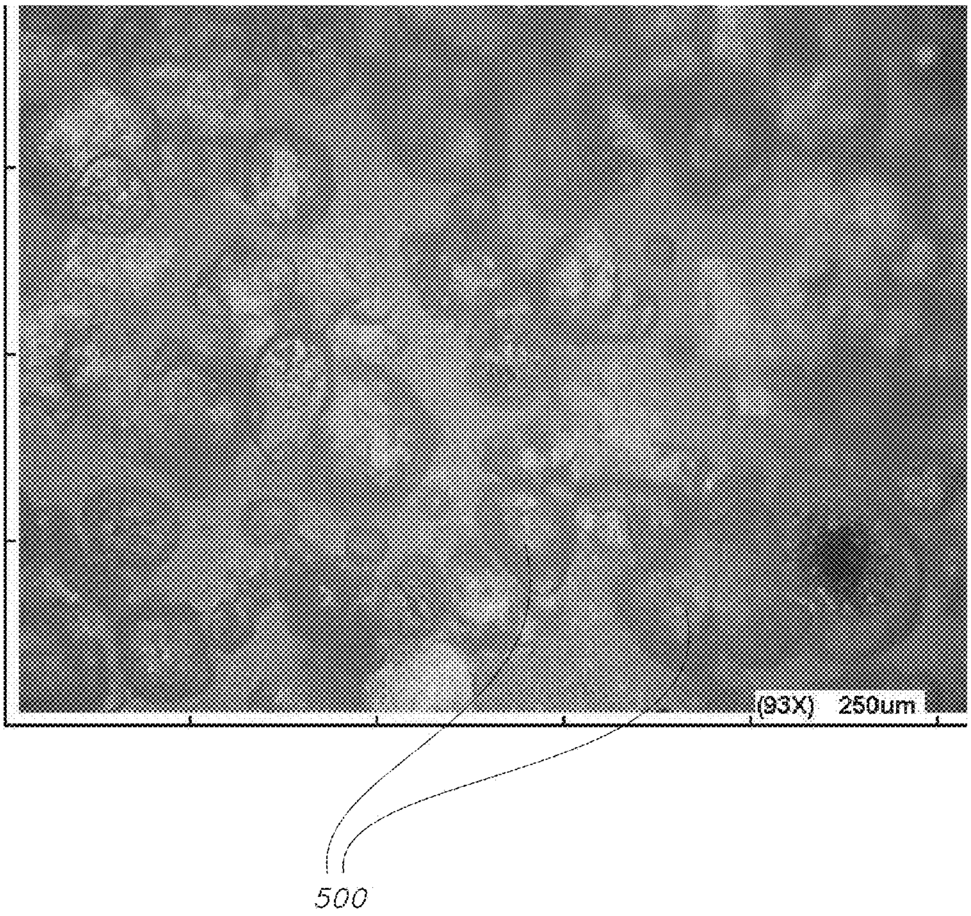
FIG. 22 is a photomicrographic representation of a film containing fat coated particles dried by the inventive drying process.
Figure 23:
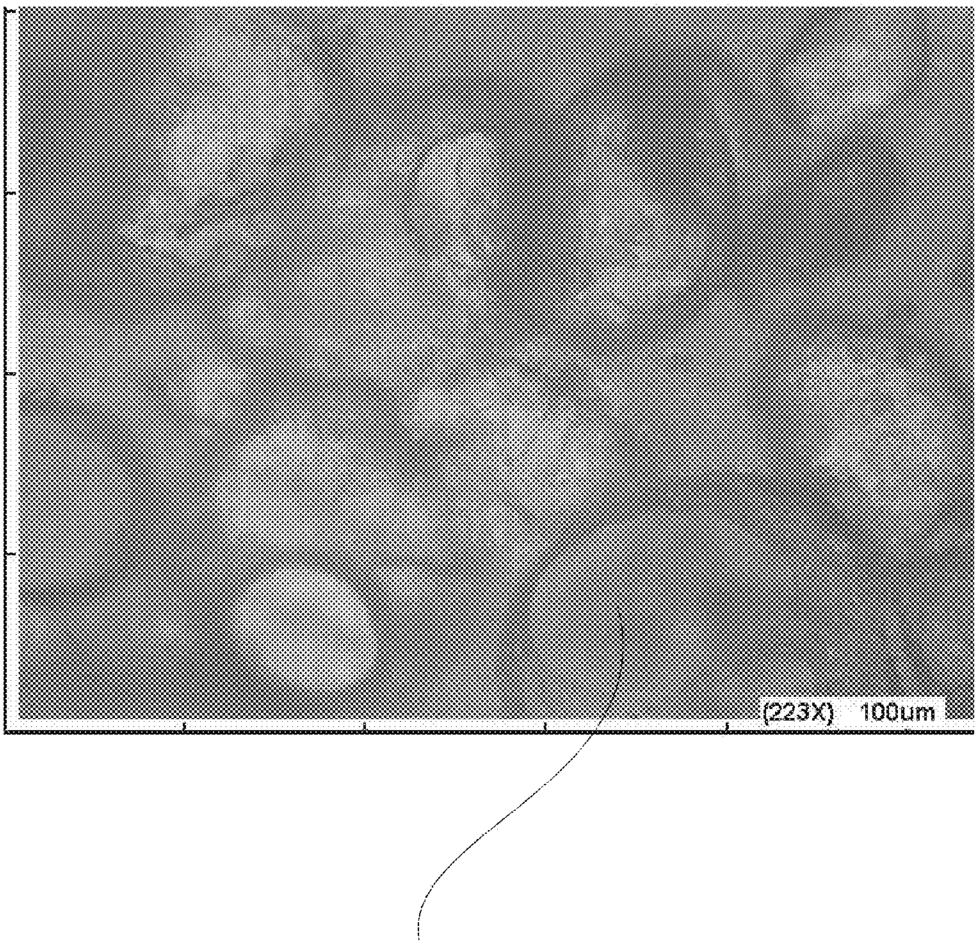
FIG. 23 is a photomicrographic representation of a film containing fat coated particles dried by the inventive drying process.
Figure 24:
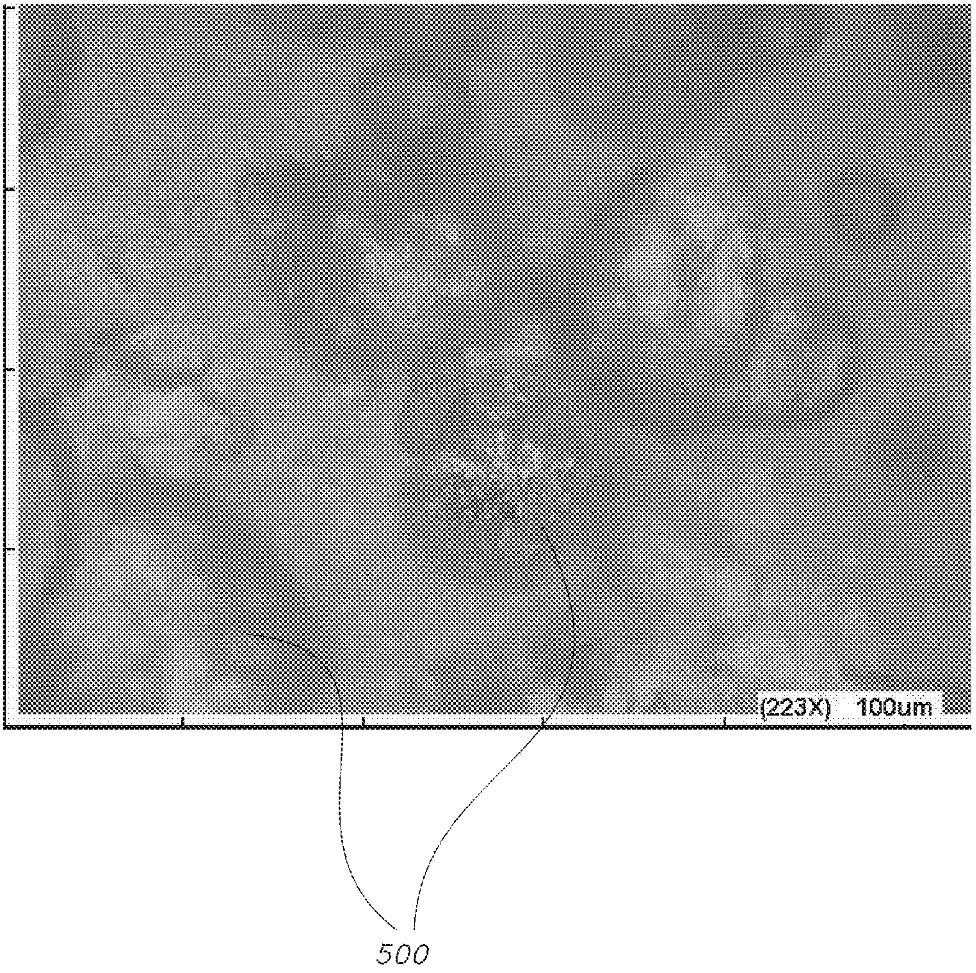
FIG. 24 is a photomicrographic representation of a film containing fat coated particles dried by the inventive drying process.
Figure 25:
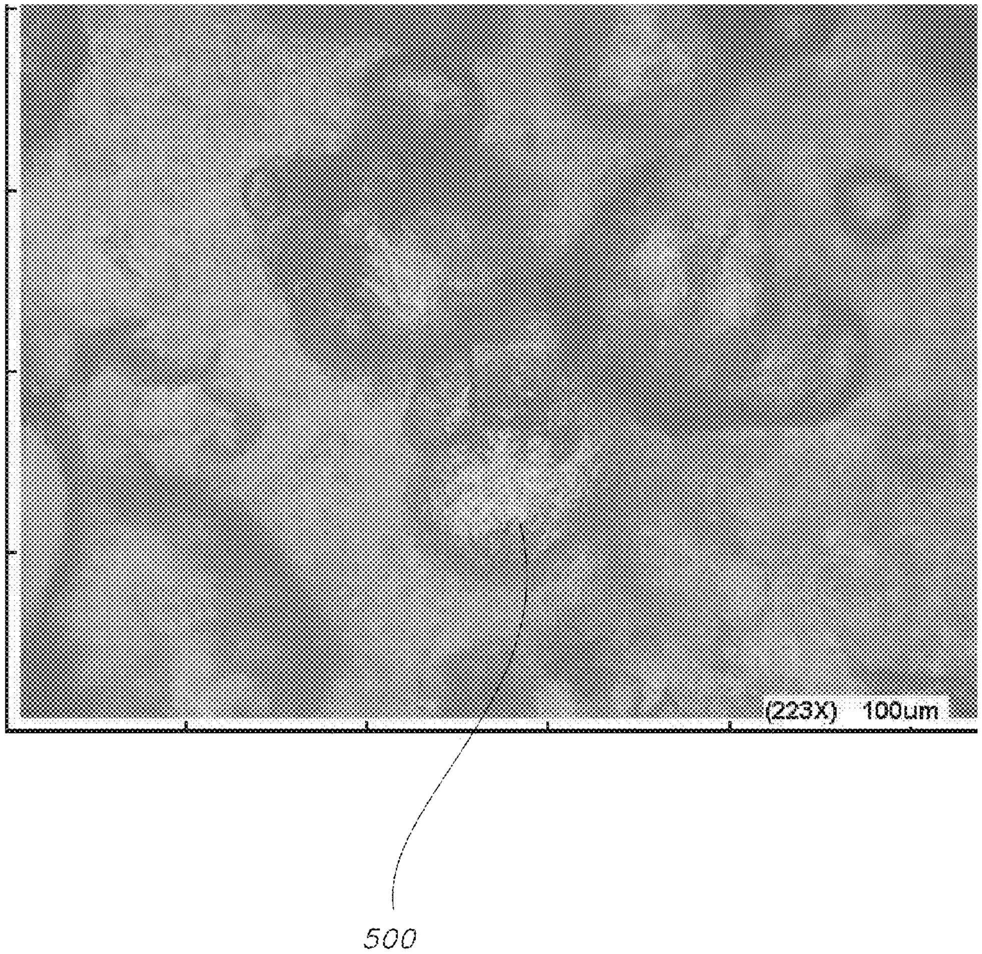
FIG. 25 is a photomicrographic representation of a film containing fat coated particles dried by the inventive drying process.

The ingredients in Table 15, in the amounts listed for CH, were combined by mixing, and then cast into three films on release paper using a K-Control Coater with a 350 micron smooth bar. The films were dried for 9 minutes in an 80° C. air oven on trays lined with furnace filters, which uniformly distribute heat. The films were dried to about 2.20 percent moisture. As depicted in FIG. 17, the dried films 200 had no streaks, and were homogenous, i.e., no particle aggregations developed. The active particles appeared intact in the dried films. The films exhibited adequate strength and passed the 180° bend test without cracking, in which the films are bent in half with pressure.

The mixed solution was cast into three more films on release paper using a K-Control Coater with a 350 micron smooth bar. These films similarly were dried for 9 minutes in an 80° C. air oven, but by conventional top and bottom drying means. Two of the films were dried on wire racks, while the third was dried on a wire screen. All three films were dried to about 2.65 percent moisture. The dried films showed the imprints of the wire racks and screen, for the reasons described above in Example CG.

More particularly, the dried films 100 exhibited aggregations 110 of particles in both line and diamond configurations, as shown in FIGS. 9-16. These configurations comprise imprints of wire supports used in the drying process to display the disuniformity in heat transfer which occurs in conventional top and bottom drying. As discussed above, the wire supports conducted heat more intensely at the points of contact with the substrate, leading to increased evaporation at these points. This caused more vigorous mixing, thereby pulling more particles to the contact points. The resulting increased particle density at the contact points is depicted in FIGS. 9-16.

Figure 26:
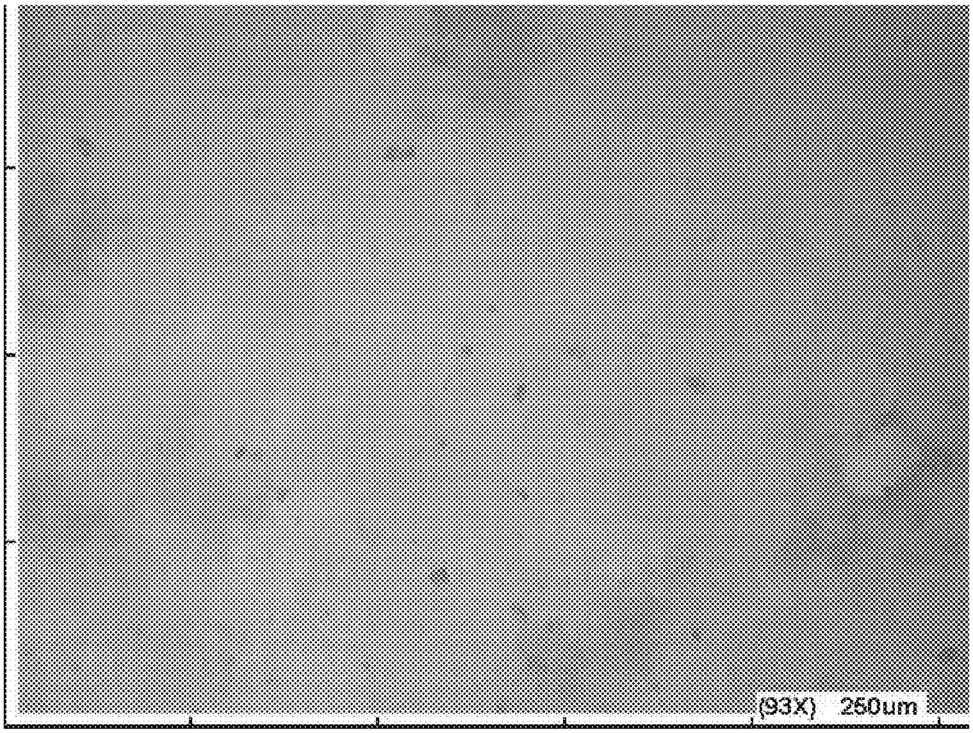
FIG. 26 is a photomicrographic representation of fat coated particles not in film, heated for 9 minutes at 80° C.
Figure 27:
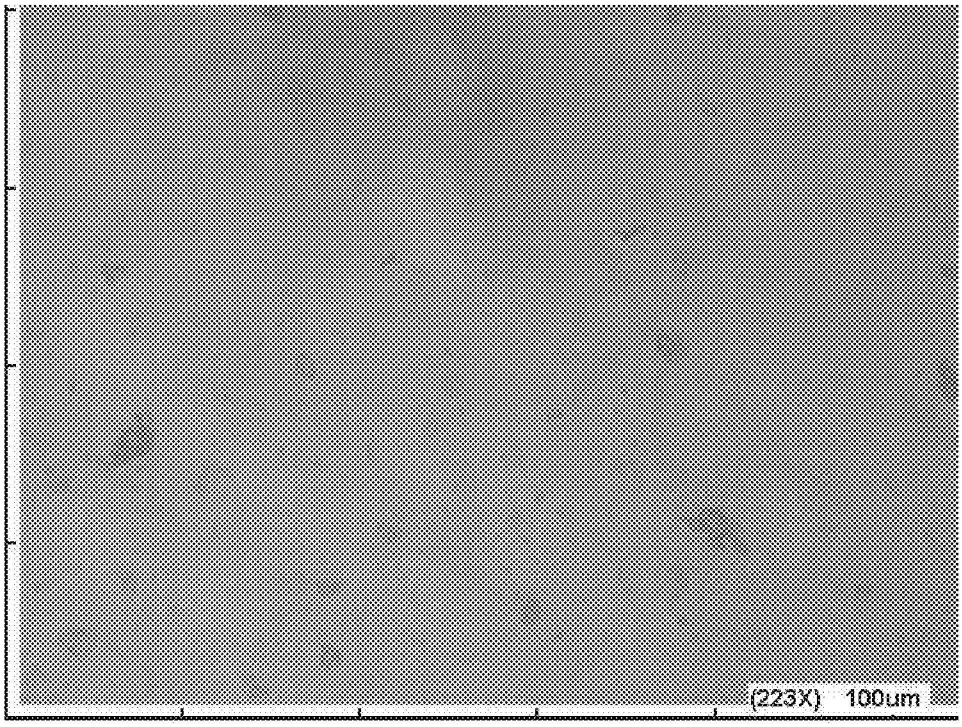
FIG. 27 is a photomicrographic representation of fat coated particles not in film, heated for 9 minutes at 80° C.
Figure 28:
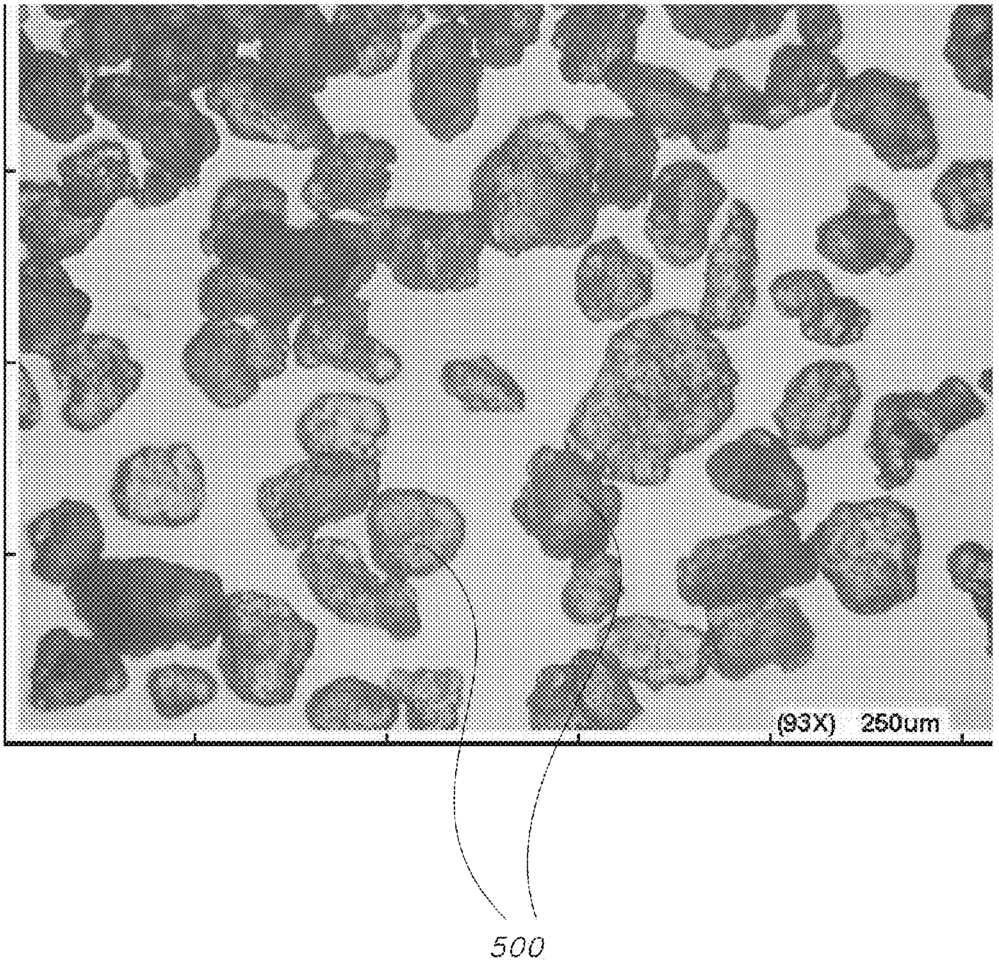
FIG. 28 is a photomicrographic representation of fat coated particles at room temperature prior to processing.
Figure 29:
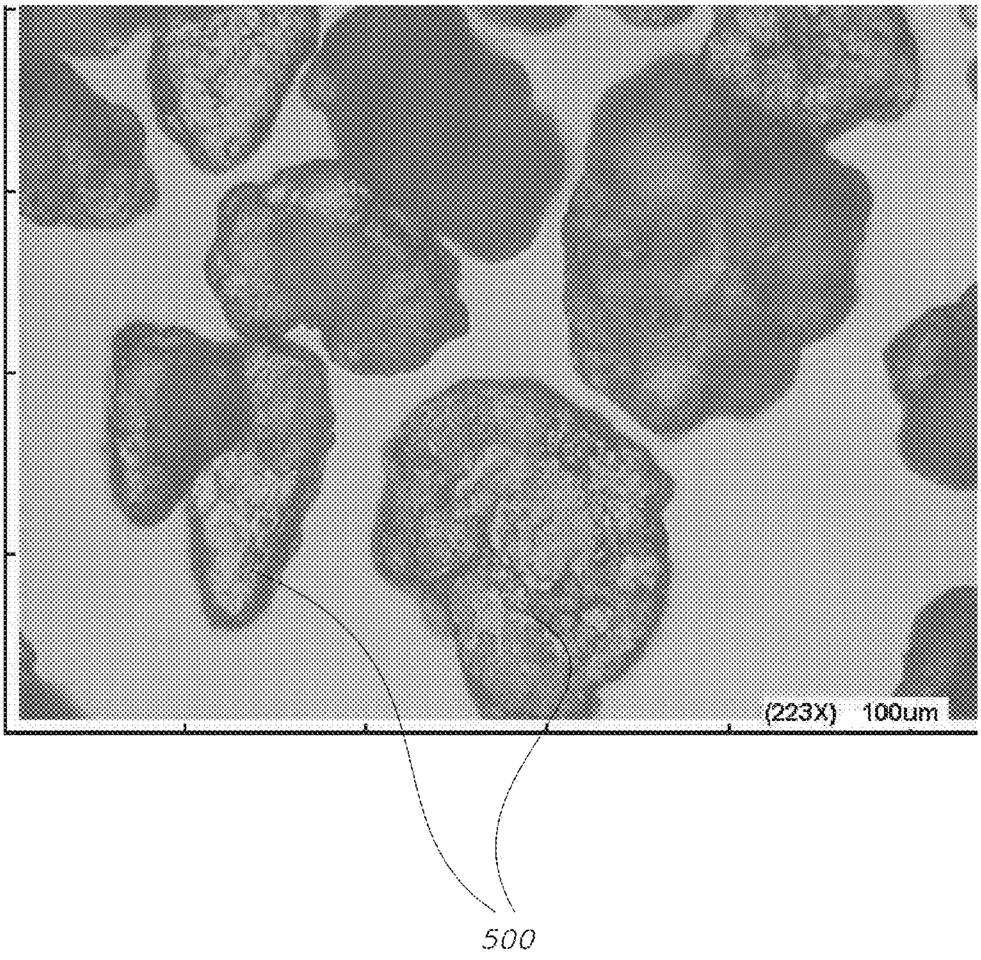
FIG. 29 is a photomicrographic representation of fat coated particles at room temperature prior to processing.
Figure 30:
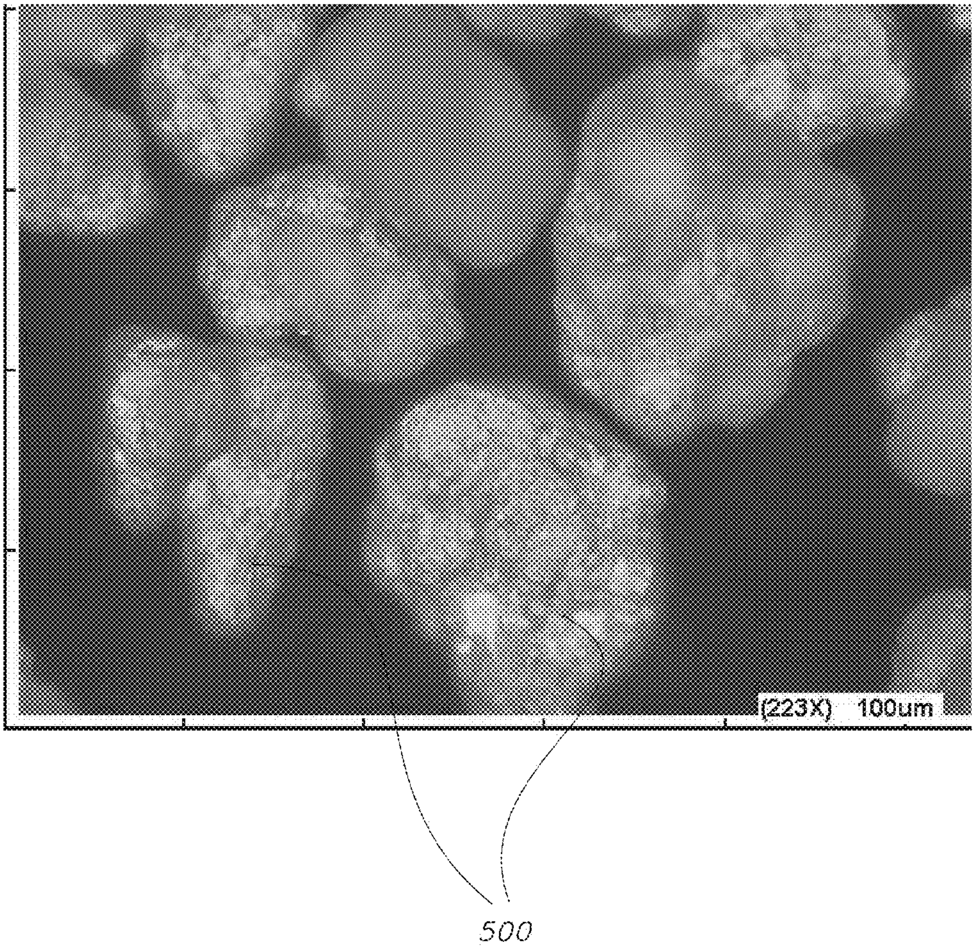
FIG. 30 is a photomicrographic representation of fat coated particles at room temperature prior to processing.
Figure 31:
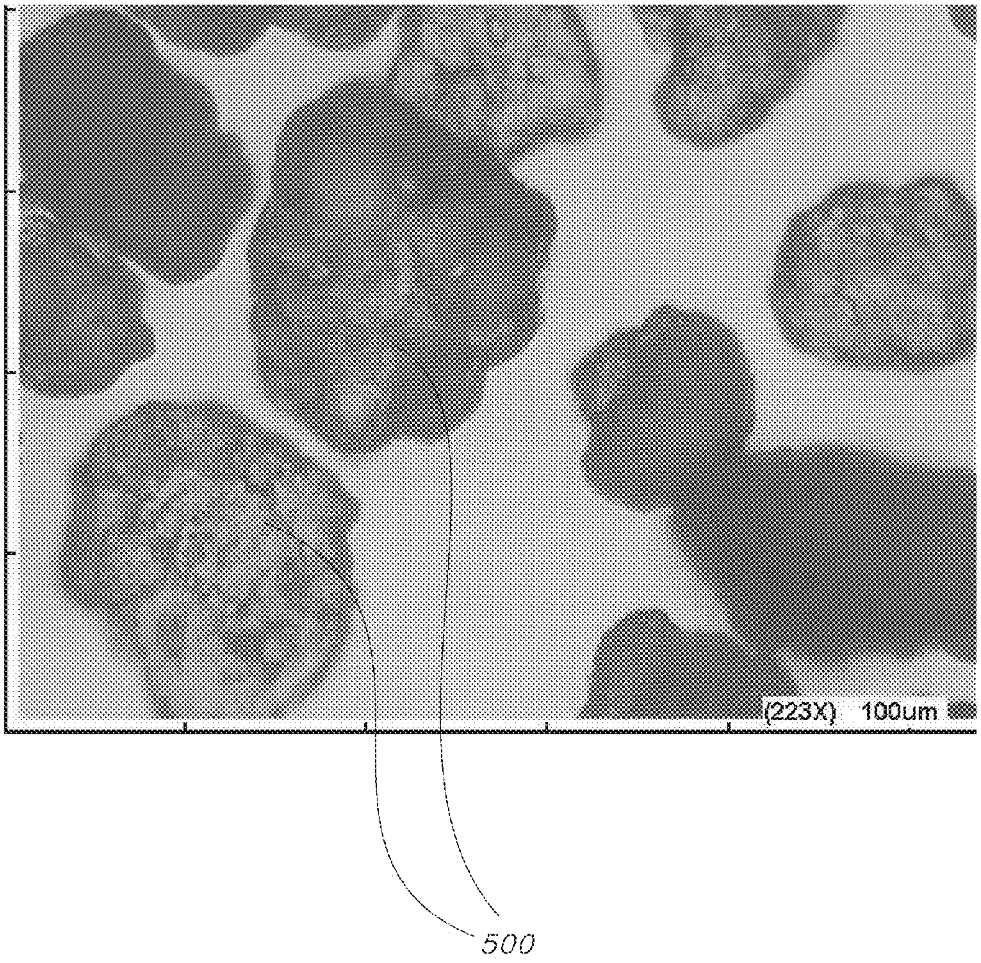
FIG. 31 is a photomicrographic representation of fat coated particles at room temperature prior to processing.

Moreover, the fat-coated dextromethorphan particles contained within the films of this example were not destroyed by the drying processes. FIGS. 28-31 depict fat-coated dextromethorphan particles 500 prior to any processing, and particularly, their substantially spherical shape. After exposure to drying conditions of 80° C. for 9 minutes, the fat-coated drug particles 500 were found to have remained intact within the films, i.e., maintained their spherical shape, as shown in FIGS. 18-25. Although the active particles were exposed to potentially deleterious temperatures, they did not degrade. In contrast, fat-coated dextromethorphan particles placed in an evaporating dish and heated in an air oven at 80° C. for 9 minutes substantially degrade. As seen in FIGS. 26 and 27, the fat-coated dextromethorphan particles appear completely melted after the exposure.

Example CI

Thin film compositions of the present invention were prepared using the amounts described in Table 16.

TABLE 16

| Component | Weight (g unless otherwise indicated) |
|---|---|
| Hydroxypropylcellulose | 6.00 |
| Polyethylene oxide | 2.00 |
| Sucralose[1] | 0.84 |
| Magna sweet[2] | 0.09 |
| Mixture of microcrystalline cellulose and sodium carboxymethylcellulose[3] | 0.18 |
| Precipitated calcium carbonate | 1.55 |
| Sildenafil[4] | 2.91 |
| Peppermint & bittermint flavor | 1.75 |
| Prosweet[5] | 0.44 |
| Masking flavor[6] | 1.31 |
| N,2,3-trimethyl-2-isopropylbutanamide[7] | 0.075 |
| Simethicone[8] | 0.035 |
| Water | 32.5 |
| Blue food coloring | 3 drops |

[1]Available from McNeil Nutritional
[2]Taste-masking flavor, available from Mafco Worldwide Corp.
[3]Avicel CL-611, available from FMC Biopolymer
[4]Available from Pfizer, Inc. as Viagra ®
[5]Taste-masking flavor, available from Virginia Dare
[6]Available from Ungerer and Co.
[7]Cooling agent
[8]Available from Sentry The above ingredients were combined by mixing until a uniform mixture was achieved, and then cast into two films on release paper using a K-Control Coater with a 350 micron smooth bar. One film was dried for 10 minutes in an 80° C. air oven to a moisture level of 3.52%, while the second film was dried for 10 minutes in an 80° C. air oven to a moisture level of 3.95%. The dried films had adequate strength and tear resistance. The films passed the 180° bend test without breaking. The films also dissolved at a moderately fast rate in the mouth and exhibited an acceptable flavor.

As mentioned above, the controlled drying process of the present invention allows for uniform drying to occur, whereby evaporative cooling and thermal mixing contribute to the rapid formation of viscoelastic film and the "locking-in" of uniformity of content throughout the film. One of the additional advantages of the present invention is that the film composition reaches its viscoelastic state, and even the fully dried state, without exposing the components of the composition to temperatures which will cause them to be altered or unusable for their intended purpose. For example, heat sensitive drugs, proteins, flavors, sweeteners, volatile components, antigens, antibodies and the like, readily decompose at certain temperatures become inactive or denature, making them ineffective for their intended use. In the present invention, due to the combination of a short heat history required to dry, and the controlled non-top-skinning drying process, the film composition never need to attain the oven temperature (or other heat source) to reach the dried state. To demonstrate this, films were made in accordance with the present invention and dried as discussed below. A first thermocouple was placed within the film and a second thermocouple was suspended in the oven in order to measure the temperature differential between the oven environment and the film composition during the drying process.

To measure the temperature differentials, a thermocouple, which was connected to a Microtherma 1 thermometer, was placed within the films, and another thermocouple was suspended in the drying oven. Temperature readings in the films and oven were recorded every 30 seconds during the drying of the films.

Figure 33:
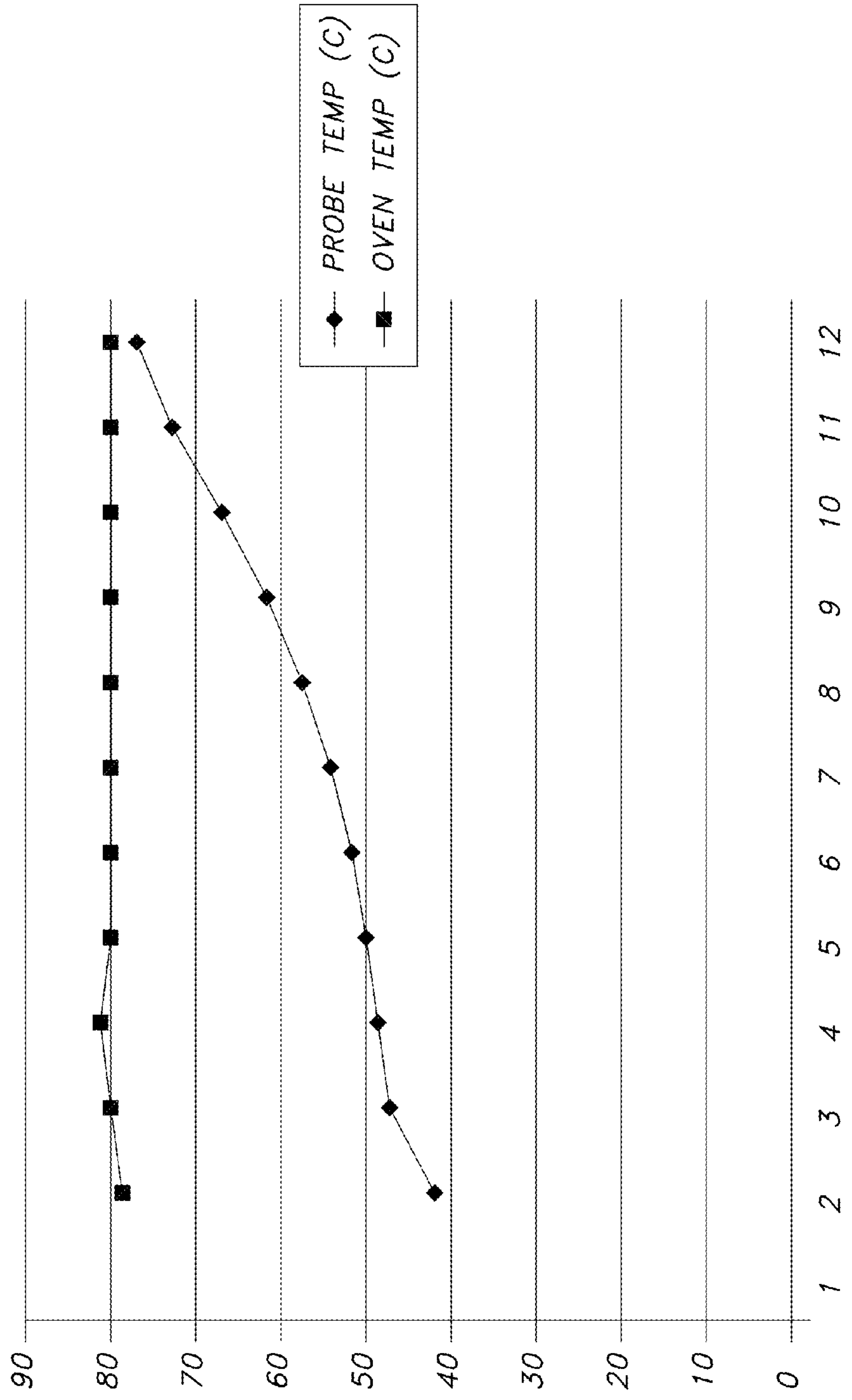
FIG. 33 is a graphical representation of the temperature differential between the inside and outside of a film of the present invention during drying.
Figure 34:
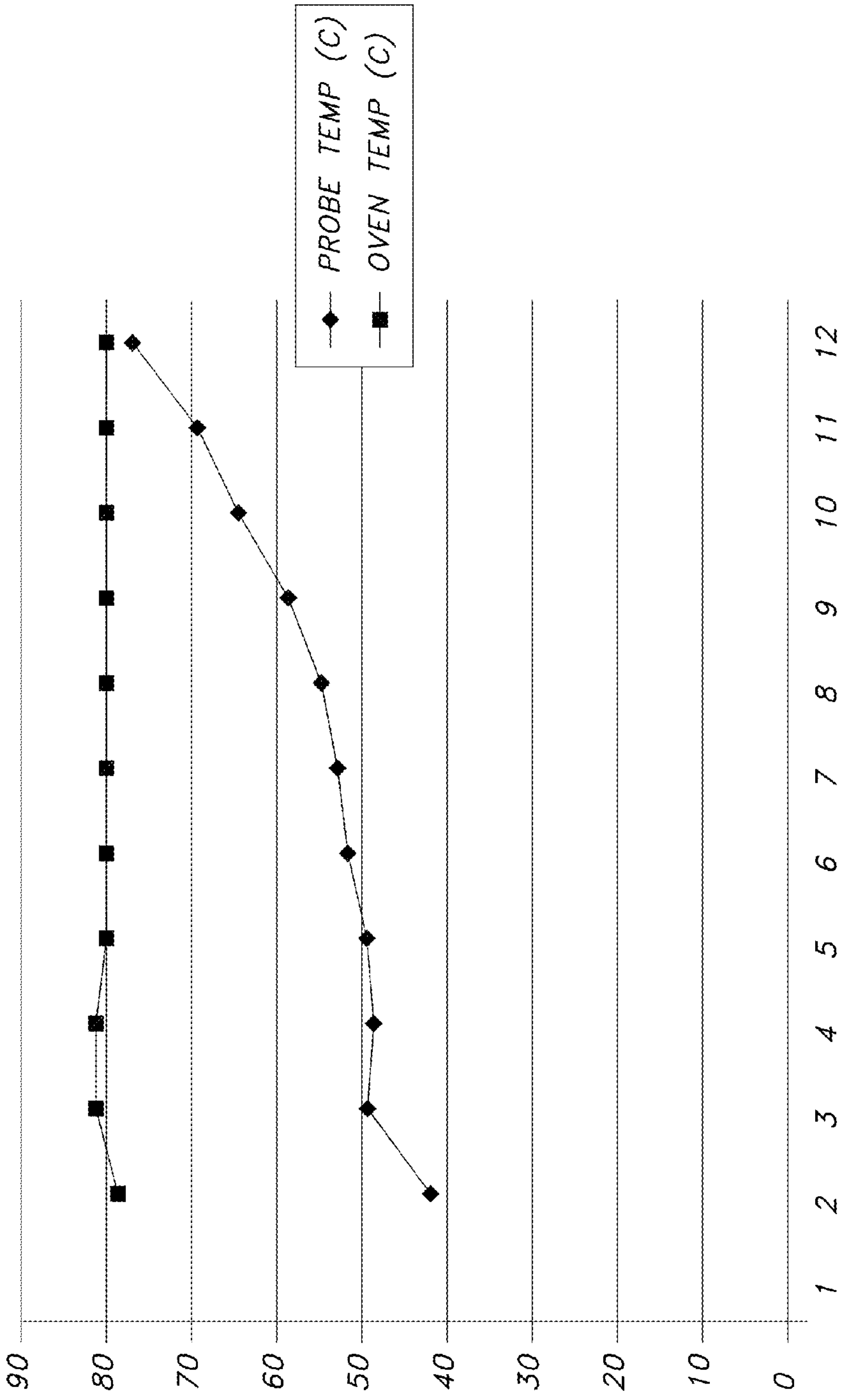
FIG. 34 is a graphical representation of the temperature differential between the inside and outside of a film of the present invention during drying.

The thermocouple results for the first film are listed in Table 17 below, and graphically represented in FIG. 33. The results for the second film are listed in Table 18 below, and graphically represented in FIG. 34. The results show that even after 10 minutes of drying, the temperatures of the film were substantially below (at least about 5° C.) the oven environment. Films dried for less than 10 minutes may experience significantly greater temperature differentials. For example, drying for 4 to 6 minutes, which is a particularly desirable time frame for many films of the present invention, produces differentials of about 25° C. to about 30° C. Accordingly, films may be dried at high, potentially deleterious temperatures without harming heat sensitive actives contained within the films.

TABLE 17

| Time (Min.) | Probe Temp (° C.) | Oven Temp (° C.) |
|---|---|---|
| 0 | 42.7 | 78 |
| 1 | 48.1 | 80 |
| 2 | 48.8 | 81 |
| 3 | 50 | 80 |
| 4 | 51.6 | 80 |
| 5 | 53.6 | 80 |
| 6 | 56.8 | 80 |
| 7 | 61.4 | 80 |
| 8 | 66.8 | 80 |

TABLE 17-continued

| Time (Min.) | Probe Temp (° C.) | Oven Temp (° C.) |
|---|---|---|
| 9 | 72.7 | 80 |
| 10 | 76.1 | 80 |

TABLE 18

| Time (Min.) | Probe Temp (° C.) | Oven Temp (° C.) |
|---|---|---|
| 0 | 44.4 | 77 |
| 1 | 49.8 | 81 |
| 2 | 49.2 | 81 |
| 3 | 49.4 | 80 |
| 4 | 51 | 80 |
| 5 | 52 | 80 |
| 6 | 55 | 80 |
| 7 | 58.9 | 80 |
| 8 | 64.5 | 80 |
| 9 | 69.8 | 80 |
| 10 | 74.4 | 80 |

Examples CJ-DB

The following examples describe film compositions of the present invention, which contain water-soluble polymers including polyethylene oxide (PEO) alone or in combination with hydroxypropyl cellulose (HPC) or hydroxypropylmethyl cellulose (HPMC). Thin film compositions were prepared using the polymer amounts listed in Table 19.

TABLE 19

| Composition | PEO (g) | HPC (g) | HPMC (g) |
|---|---|---|---|
| CJ | | 32 | 8 |
| CK | | 24 | 16 |
| CL | | 16 | 24 |
| CM | | 8 | 32 |
| CN | | | 40 |
| CO | 8 | | 32 |
| CP | 16 | | 24 |
| CQ | 24 | | 16 |
| CR | 32 | | 8 |
| CS | 40 | | |
| CT | 4 | | 36 |
| CV | 6 | | 34 |
| CV | 32 | 8 | |
| CW | 24 | 16 | |
| CX | 16 | 24 | |
| CY | 8 | 32 | |
| CZ | | 40 | |
| DA | 4 | 36 | |
| DB | 6 | 34 | |

The above polymer components were combined with equal amounts of precipitated calcium carbonate (mimics drug loading), simethicone emulsion, and water to form the film compositions. The components were combined by mixing until a uniform mixture was achieved, and then cast into films on release paper using a K-Control Coater with a 350 micron smooth bar. The films then were dried for about 9 minutes at 80° C. in accordance with the present invention. The film compositions were tested for various properties, the results of which are described in Table 20 below.

TABLE 20

| Composition | Composition of Polymer in Film | Solution Coating Rating | Solution Leveling Rating | % Moisture in Film | 180° Bend Test | Dissolution Test (seconds) | Curl Test |
|---|---|---|---|---|---|---|---|
| CJ | 20% HPMC/ 80% HPC | well | well | 2.9 | Failed at crease | 12, 15 | Curl |
| CK | 40% HPMC/ 60% HPC | well | well | 1.70 | Failed at crease | 21, 22 | Curl |
| CL | 60% HPMC/ 40% HPC | well | well | 2.40 | Failed at crease | 24, 27 | Curl |
| CM | 80% HPMC/ 20% HPC | well | well | 2.76 | Failed at crease | 31, 31 | Curl |
| CN | 100% HPMC | reasonably well | well | 2.66 | Failed at crease | 35, 38 | Curl |
| CO | 10% PEO/ 90% HPMC | some streaking | well | 2.27 | Failed at crease | 31, 32 | Curl |
| CP | 15% PEO/ 85% HPMC | well | well | 3.31 | Failed | 24, 27 | Curl |
| CQ | 20% PEO/ 80% HPMC | well | well | 2.06 | Passed | 22, 31 | Slight curl |
| CR | 40% PEO/ 60% HPMC | well | well | 2.01 | Passed | 13, 12 | Slight curl |
| CS | 60% PEO/ 40% HPMC | well | well | 1.40 | Passed | 5, 6 | Very slight curl |
| CT | 80% PEO/ 20% HPMC | well | well | 1.35 | Passed | 5, 6 | Very slight curl |
| CU | 100% PEO | well | well | 0.98 | Passed | 5, 5 | No curl |
| CV | 20% HPC/ 80% PEO | well | well | 1.01 | Passed | 5, 5 | No curl |
| CW | 40% HPC/ 60% PEO | well | well | 2.00 | Passed | 6, 6 | No curl |
| CX | 60% HPC/ 40% PEO | well | well | 0.97 | Passed | 7, 7 | Slight curl |
| CY | 80% HPC/ 20% PEO | well | well | 1.41 | Passed | 12, 12 | Very slight curl |
| CZ | 85% HPC/ 15% PEO | well | well | 1.86 | Failed at crease | 13, 14 | Curl |
| DA | 90% HPC/ 10% PEO | well | well | 1.62 | Failed at crease | 14, 13 | Curl |
| DB | 100% HPC | well | well | 2.01 | Failed at crease | 16, 17 | Curl |

The solution coating rating and solution leveling rating were both based upon panel observations made during casting of the film compositions.

For the 180° bend test, the dried films were placed in a moisture analyzer (HR73 Moisture Analyzer from Mettler Toledo) to obtain percent moisture and to remove any solvent (e.g. water) remaining in the films after drying at 80° C. in accordance with the present invention. The films then were creased to about 180° and observed for break. Films that broke during creasing were considered a failure. If the film did not break during creasing, a 200 g weight was dropped onto the creased film from a height of about 8.5 mm. Films that broke were considered a failure, and those that did not break were considered a pass. It should be noted, however, that this flexibility test is an extreme test. Films that failed this test are still considered operable within the scope of the present invention. More specifically, there may be certain applications that do not require such extreme flexibility properties.

The films also were tested for dissolution rate. An approximately 20 mm by 100 mm piece of film, having a 2.85 g weight attached, was lowered into a 32.5° C. water bath to a depth of about 50 mm. The time required for the film to dissolve and separate into two pieces was determined (in seconds).

For the curl test, samples of film (about 35 mm by 35 mm) were placed on a glass plate in a laboratory window ledge. The film samples were allowed to stand in the window ledge at room conditions for two to three days and then were observed for curling.

In accordance with the present invention, desirable film compositions are flexible, fast dissolving, and not likely to substantially curl. As indicated by the results in Table 20, Compositions CQ-CY performed best, exhibiting good flexibility, dissolution, and curling properties. In particular, Compositions CQ-CY passed the 180° bend test and dissolved at moderate to fast rates. These compositions also exhibited no or only slight curl. Accordingly, it may be desirable to employ polymer components as in Compositions CQ-CY, particularly about 20% to 100% PEO in the polymer component optionally combined with about 0% to 80% HPC or HPMC.

Examples DC-DG

The following examples of the present invention describe films that include PEO or PEO-polymeric blends and an active component. Thin film compositions with these components were prepared using the amounts described in Table 21.

TABLE 21

| Component | Weight (g unless otherwise indicated) | | | | |
|---|---|---|---|---|---|
| | DC | DD | DE | DF | DG |
| PEO[1] | 8.75 | 7 | 1.75 | 7 | 1.75 |
| Sucralose | 0.7 | 0.7 | 0.7 | 0.7 | 0.7 |
| Precipitated calcium carbonate | 3.65 | 3.65 | 3.65 | 3.65 | 3.65 |
| Orange concentrate flavor | 1.05 | 1.05 | 1.05 | 1.05 | 1.05 |
| Vanilla | 0.5 | 0.5 | 0.5 | 0.5 | 0.5 |
| HPMC | | 1.75 | 7.0 | | |
| HPC | | | | 1.75 | 7.0 |
| Simethicone[2] | 0.35 | 0.35 | 0.35 | 0.35 | 0.35 |
| Water | 32.5 | 32.5 | 32.5 | 32.5 | 32.5 |

TABLE 21-continued

| Component | Weight (g unless otherwise indicated) | | | | |
|---|---|---|---|---|---|
| | DC | DD | DE | DF | DG |
| Loratadine[3] | 2.5 | 2.5 | 2.5 | 2.5 | 2.5 |
| Yellow food coloring | 3 drops | 3 drops | 3 drops | 3 drops | 3 drops |
| Red food coloring | 2 drops | 2 drops | 2 drops | 2 drops | 2 drops |

[1]Available from the Dow Chemical Company
[2]Available from Sentry
[3]Available from Schering Corporation as Claritin The above components for each of Compositions DC through DG were combined by mixing until a uniform mixture was achieved, and then cast into films on release paper using a K-Control Coater with a 350 micron smooth bar. The films were dried for about 9 minutes at 80° C. in accordance with the method of the present invention to varying moisture levels.

After drying, the films were tested for various properties, including the 180° bend test, dissolution test, and curl test, as described above in Examples CJ-DB. The films also were tested for resistance to tearing. Tear resistance was measured by a panel test in which members tried to tear the film apart by pulling on opposing ends of the film. Films that tore cleanly received a low grade. Films that stretched a little and began to break received a moderate grade, and films that stretched and were difficult to tear received a high grade.

Composition DC, which included a 100% PEO film base, was dried in accordance with the method of the present invention to about 1.30 percent moisture. The dried film had good strength, and passed the 180° bend test. The film also exhibited good resistance to tearing (high grade). The film dissolved at a fast rate on the tongue, and had a dissolution testing rate of about 3.5 to 4 seconds. The film exhibited no curling.

Composition DD, which included an 80%/20% PEO/HPMC film base, was dried in accordance with the method of the present invention to about 2.30 percent moisture. The dried film exhibited adequate strength, and passed the 180° bend test. The film also exhibited good resistance to tearing. It dissolved at a moderate to fast rate on the tongue, and had a dissolution testing rate of about 5 seconds. The film exhibited slight curling.

Composition DE, which included a 20%/80% PEO/HPMC film base, was dried in accordance with the method of the present invention to about 3.0 percent moisture. The film had good strength, and passed the 180° bend test. The film exhibited moderate tear resistance, dissolved on the tongue at a slow rate, and had a dissolution testing rate of 16 seconds. The film exhibited some curling.

Composition DF, which included an 80%/20% PEO/HPC film base, was dried in accordance with the method of the present invention to about 2.52 percent moisture. The film exhibited good strength, passed the 180° bend test, and exhibited high tear resistance. The film also dissolved at a fast rate on the tongue, and had a dissolution rating of 4 seconds. The film exhibited very slight curling.

Composition DG, which included a 20%/80% PEO/HPC film base, was dried in accordance with the method of the present invention to about 2.81 percent moisture. The film had adequate strength, passed the 180° bend test, and exhibited moderate tear resistance. The film dissolved on the tongue at a fast rate, and had a 10 second dissolution testing rate. The film exhibited no curling.

As indicated above, each of Compositions DC-DG contained about 20% to 100% PEO in the polymer component, optionally in combination with varying levels of HPC or HPMC. The results indicate that varying the polymer component achieved different film properties.

Examples DH-DZ

The following examples of the present invention describe films that include PEO or PEO-HPC polymer blends. The film compositions include PEO of varying molecular weights. Thin film compositions with these components were prepared using the amounts described in Table 22 (listed by weight percent of the polymer component).

TABLE 22

| Composition | 100,000 PEO (wt. %) | 200,000 PEO (wt. %) | 300,000 PEO (wt. %) | 900,000 PEO (wt. %) | HPC (wt. %) |
|---|---|---|---|---|---|
| DH | | | 20 | | 80 |
| DI | | | 50 | | 50 |
| DJ | | | 80 | | 20 |
| DK | | 50 | | | 50 |
| DL | | 67.5 | | | 32.5 |
| DM | | 70 | | | 30 |
| DN | | 75 | | | 25 |
| DO | | 100 | | | |
| DP | 50 | | | | 50 |
| DQ | 100 | | | | |
| DR | | | | 10 | 90 |
| DS | | | | 20 | 80 |
| DT | | 40 | | 10 | 50 |
| DU | 25 | | | 15 | 60 |
| DV | 20 | 80 | | | |
| DW | | 80 | | 20 | |
| DX | | 80 | 20 | | |
| DY | | 50 | 50 | | |
| DZ | | 20 | 80 | | |

The above polymer components were combined with sucralose, precipitated calcium carbonate (mimics drug loading), orange concentrate flavor, Tween 80 (available from ICI Americas), vanilla flavor, simethicone emulsion, water, and yellow and red food coloring to form the film compositions. The components were combined by mixing until a uniform mixture was achieved, and then cast into films on release paper using a K-Control Coater with a 350 micron smooth bar. The solution coating and leveling properties were observed. The films then were dried for about 9 minutes at 80° C. in accordance with the method of the present invention. The film compositions were tested for various properties to determine the effect of varying the PEO molecular weight and level in the polymer component, the results of which are described in Table 23 below.

TABLE 23

| Composition | Film thickness (mils) | % Moisture | Roof of Mouth Tendency | 180° Bend Test | Dissolution Test (seconds) | Tear Resistance |
|---|---|---|---|---|---|---|
| DH | 3.5 | 2.5 | low | passed | 8 | poor |
| DI | 3.8 | 2.01 | low | passed | 7 | moderate |
| DJ | 2.6 | 2.63 | high | passed | 3 | excellent |
| DK | 3.4 | 2.35 | low | passed | 4 | poor |
| DL | 3.5 | 1.74 | low | passed | 4 | good to excellent |
| DM | 3.5 | 1.68 | low | passed | 4 | good to excellent |
| DN | 3.3 | 2.33 | moderate | passed | 3 | good to excellent |
| DO | 3.1 | 2.14 | high | passed | 4 | excellent |
| DP | 4.1 | 1.33 | high | passed | 3.5 | poor |
| DQ | 3.2 | 2.07 | high | passed | 4 | good |
| DR | 3.4 | 1.90 | low | passed | 10 | poor |
| DS | 3.5 | 2.04 | low | passed | 10 | poor |
| DT | 3.3 | 2.25 | moderate | passed | 5 | good |
| DU | 3.6 | 2.84 | low to moderate | passed | 6 | moderate |
| DV | 2.5 | 3.45 | high | passed | 2 | excellent |
| DW | 2.5 | 2.83/1.68 | high | passed | 3-4 | excellent |
| DX | 3.5 | 2.08 | high | passed | 5 | excellent |
| DY | 2.8 | 1.67 | high | passed | 3 | excellent |
| DZ | 2.5 | 1.89/0.93 | high | passed | 3 | excellent |

The films were tested for various properties, including the 180° bend test, dissolution test, and tear resistance, as described above. The films also were tested for adhesion, i.e., tendency to go to the roof of the mouth. Adhesion was rated by a panel test in which films that did not stick to the roof of the mouth received a low grade, films that stuck somewhat received a moderate grade, and films that stuck completely received a high grade.

As indicated above, the level and molecular weight of PEO in the polymer component were varied to achieve different film properties. In general, the higher the level of PEO in the polymer component, the greater the adhesiveness and tear resistance exhibited by the film. Film compositions containing about 50% or greater levels of PEO attained higher tear resistance ratings than those with less than 50% PEO. The tear resistance of lower levels of PEO, however, was shown to be improved by combining small amounts of higher molecular weight PEOs with the lower molecular weight PEOs (e.g. Compositions DT and DU).

Compositions containing about 20% to 75% PEO performed best with respect to adhesion prevention (lower tendencies to go to the roof of the mouth). Compositions containing higher levels of PEO performed well when adhesion was desired.

As regards dissolution rate, polymer components containing about 50% or higher levels of PEO performed best, providing faster dissolving film compositions. In those films containing combinations of varying molecular weight PEOs, those with about 60% or higher of the lower molecular weight PEOs (100,000 to 300,000) in the PEO combination dissolved faster.

Example EA

The following example of the present invention describes films that include PEO and polyvinyl pyrrolidone (PVP) polymeric blends. Thin film compositions with these components were prepared using the amounts described in Table 24. In particular, the polymer component of the films contained about 80% PEO and 20% PVP, or a ratio of 4:1 PEO to PVP.

TABLE 24

| Component | Weight (g unless otherwise noted) |
|---|---|
| PVP | 3.75 |
| PEO | 15 |
| Sucralose[1] | 1.5 |
| Precipitated calcium carbonate | 14.57 |
| Orange concentrate flavor | 2.25 |
| Tween 80[2] | 0.056 |
| Simethicone[3] | 0.38 |
| Water | 62.5 |
| Yellow food color | 6 drops |
| Red food color | 4 drops |

[1]Available from McNeil Nutritionals
[2]Available from Fisher
[3]Available from Sentry The above components were combined by mixing until a uniform mixture was achieved, and then cast into films on release paper using a K-Control Coater with a 350 micron smooth bar. The films were dried for about 9 minutes at 80° C. in accordance with the method of the present invention to a moisture level of about 2.19%. The films exhibited good strength, dissolved in the mouth at a moderate to fast rate, had high tear resistance, a thickness of about 4 mils, good flavor, low tendency to adhere to the roof of the mouth, and passed the 180° bend test. The film had a dissolution rate of 4 seconds, according to the test described above. In addition, the film easily released from the release paper.

Example EB-ED

The following examples of the present invention describe extruded films that include PEO-based polymer components. Film compositions were prepared using the amounts described in Table 25 for Example EC and Table 26 for Example ED.

TABLE 25

| COMPONENT | WEIGHT (g unless otherwise noted) |
|---|---|
| HPC | 73.78 |
| Polyethylene oxide | 153.22 |
| Sucralose | 18.16 |
| Precipitated calcium carbonate | 176.38 |
| Orange concentrated flavor | 27.24 |
| Tween 80 | 0.68 |
| Simethicone | 4.54 |
| Yellow food coloring | 27 drops |
| Red food coloring | 18 drops |

TABLE 26

| COMPONENT | WEIGHT (g unless otherwise noted) |
|---|---|
| Polyethylene oxide | 227 |
| Sucralose | 18.16 |
| Precipitated calcium carbonate | 176.38 |
| Orange concentrated flavor | 27.24 |
| Tween 80 | 0.68 |
| Simethicone | 4.54 |
| Yellow food coloring | 27 drops |
| Red food coloring | 18 drops |

The films of Examples EB-ED were extruded using a single screw extruder in accordance with the specifications provided in Table 27 below (temperatures are in ° F.).

TABLE 27

| Composition | RPM | Temp. Barrel Zn. 1 | Temp. Barrel Zn. 2 | Temp. Barrel Zn. 3 | Temp. Zn. 4 | Temp. Die | Temp. Melt | PSI Pressure P1 | PSI Pressure P2 | Amps |
|---|---|---|---|---|---|---|---|---|---|---|
| EB | 73 | 175 | 181 | 185 | 190 | 190 | 194 | 600 | 1250 | 12 |
| EB | 153 | 177 | 181 | 199 | 211 | 210 | 217 | 175 | 1070 | 7.8 |
| ED | 253 | 175 | 181 | 200 | 211 | 210 | 222 | 0 | 761 | 6.3 |
| ED | 109 | 175 | 181 | 200 | 211 | 210 | 207 | 0 | 1000 | 6.0 |
| EC | 109 | 175 | 181 | 200 | 211 | 210 | 217 | 0 | 875 | 12.1 |
| EC | 149 | 175 | 200 | 226 | 248 | 239 | 258 | 0 | 583 | 7.3 |

More specifically, for Example EB, two pounds of PEO having a molecular weight of about 200,000 were weighed and placed in a polyethylene plastic bag. This PEO flush was then extruded according to the specifications in Table 27.

For Example EC, a blend of the components listed in Table 25 was prepared. The HPC, PEO, sucralose, and precipitated calcium carbonate were placed in a large electric blender and allowed to mix. A solution of orange concentrate flavor and Tween 80 was added to the blender while mixing, after which a solution of simethicone and the food colors was added to the blender while mixing. The blended composition was extruded in accordance with the specifications in Table 27.

For Example ED, a blend of the components listed in Table 26 was prepared. The PEO, sucralose, and precipitated calcium carbonate were placed in a large electric blender and allowed to mix. A solution of orange concentrate flavor and Tween 80 was added to the blender while mixing, after which a solution of simethicone and the food colors was added to the blender while mixing. The blended composition was extruded in accordance with the specifications in Table 27.

The extruded films did not exhibit stickiness to each other during processing. As such, the resulting film could be rolled or wound onto itself without the need for a backing material.

Examples EE-EH

The following examples of the present invention describe films that include a densifying agent. A thin film composition including PEO-polymeric blends and a densifying agent (simethicone) were prepared using the amounts described in Table 28.

TABLE 28

| | Weight (g unless otherwise indicated) | | | |
|---|---|---|---|---|
| Component | EE | EF | EG | EH |
| Hydroxypropylcellulose | 3.05 | 3.05 | 3.05 | 3.05 |
| Polyethylene oxide | 6.33 | 6.33 | 6.33 | 6.33 |
| Sucralose | 0.75 | 0.75 | 0.75 | 0.75 |
| Precipitated calcium carbonate | 7.47 | 7.47 | 7.09 | 7.09 |
| Orange concentrate flavor | 1.12 | 1.12 | 1.12 | 1.12 |
| Tween 80 | 0.028 | 0.028 | 0.028 | 0.028 |
| Simethicone | 0 | 0 | 0.38 | 0.38 |
| Water | 31.25 | 31.25 | 31.25 | 31.25 |
| Yellow food coloring | 3 drops | 3 drops | 3 drops | 3 drops |
| Red food coloring | 2 drops | 2 drops | 2 drops | 2 drops |

The densities of these thin film compositions were measured, the results of which are shown in Table 29.

TABLE 29

| Composition | Average Weight of Film/Density |
|---|---|
| EE | 146.5 mg/1.123 |
| EF | 126.5 mg/0.969 |
| EG | 137 mg/1.057 |
| EH | 146 mg/1.119 |

Vacuum conditions were added to two of the film compositions (EE and EH). Composition EE contained 0% simethicone and vacuum was applied. Composition EF contained 0% simethicone and no vacuum applied. As shown in Table 29 above, the density increased with the addition of vacuum conditions from 0.969 (EF) to 1.123 (EE). Composition EG contained 2% simethicone and no vacuum applied. Composition EH contained 2% simethicone and vacuum was applied. Again, density increased from 1.057 (EG) to 1.119 (EH). Overall, the density of the films increased from 0.969 (EF: no simethicone and no vacuum) to 1.057 (EG: simethicone but no vacuum) to 1.119 (EH: simethicone and vacuum).

Examples EI-EW

The following examples of the present invention describe films that include PEO or PEO-polymeric blends. In particular, PEO was combined with polyvinylpyrrolidone (PVP), starch (pregelatinized modified corn starch), sodium carboxymethyl cellulose (CMC), hydroxypropylcellulose (HPC), hydroxypropylmethyl cellulose (HPMC) or polyvinyl alcohol (PVA) to form the polymer components of the films. Thin film compositions with these components were prepared in accordance with the method of the present invention using the amounts described in FIG. 38.

In addition to the polymer components listed in FIG. 38, each of these film compositions included: about 4% sucralose, about 38.85% calcium carbonate, about 6% orange flavor, about 0.15% Tween 80, about 1% simethicone, and food coloring. The PEO included in the polymer component of these examples had a molecular weight of about 200,000.

FIG. 38 also displays certain properties of these films, including: percent solids of solution; viscosity; percent moisture; film thickness; film strength; tear resistance of the film; tendency of the film to go to the roof of the mouth; the 180° bend test; whether molding, or aggregations, are present in the film; dissolution times of the film; rating of dissolution in the mouth; and time in drying oven. Each of these film property tests is described in detail above. The results of these various tests are indicated in FIG. 38.

Examples EX-FK

The following examples of the present invention describe films that include PEO or PEO-polymeric blends (with HPC) and different active components. Thin film compositions with these components were prepared in accordance with the method of the present invention using the amounts described in Tables 30 and 31.

TABLE 30

| | Weight (in g, unless otherwise indicated) | | | | | | |
|---|---|---|---|---|---|---|---|
| Component | EX | EY | EZ | FA | FB | FC | FD |
| HPC | 5.68 | 5.64 | 6 | 6.73 | 6.22 | 6.22 | |
| PEO | 1.89 | 1.88 | 2 | 2.25 | 1.78 | 1.78 | 9.04 |
| Sucralose | 0.84 | 0.84 | 0.44 | 0.66 | 0.84 | 0.84 | 0.44 |
| Magna Sweet | 0.08 | 0.08 | 0.09 | 0.10 | 0.09 | 0.09 | |
| Avicel CL 611[1] | 0.18 | 0.18 | 0.18 | 0.20 | 0.18 | 0.18 | |
| Precipitated calcium carbonate | 0.67 | | 2.2 | | 0.71 | 3.07 | |
| Dextromethorphan | 5.83 | 6.94 | | | | | |
| Caffeine | | | 3.28 | | | | |
| Tadalafil[2] | | | | 4.92 | | | |
| Sildenafil[3] | | | | | 4.38 | | |
| Loperamide[4] | | | | | | 2.8 | |
| Prosweet | 0.18 | 0.18 | | 0.20 | 0.61 | 0.18 | |
| Taste Masking Flavor | | | 0.87 | | 1.31 | 0.89 | |
| Peppermint | | | 0.87 | | | | |
| Peppermint Bittermask flavor | | | 1.07 | | | | |
| Vanilla flavor | | | | 0.56 | | | |
| Watermelon artificial flavor | 1.23 | 1.23 | | | 1.22 | | |
| Orange flavor | | | | 1.18 | | | |
| Hawaiian punch flavor | | | | | | 1.22 | |
| Strawberry & cream flavor | | | | | | | 1.11 |
| WS-23[5] | 0.075 | 0.075 | 0.075 | 0.084 | 0.075 | 0.075 | |
| WS-3[6] | | | | | | | 0.025 |

TABLE 30-continued

| | Weight (in g, unless otherwise indicated) | | | | | | |
|---|---|---|---|---|---|---|---|
| Component | EX | EY | EZ | FA | FB | FC | FD |
| Simethicone | 0.08 | 0.08 | 0.18 | 0.39 | 0.09 | 0.18 | 46.43 |
| Propylene glycol | 0.76 | 0.38 | 0.25 | 0.22 | | | |
| Water | 32.5 | 32.5 | 32.5 | 32.5 | 32.5 | 32.5 | |
| Green color | 5 drop | 5 drop | | | 5 drop | | |
| Red color | | | | 2 drop | | 5 drop | 7 drop |
| Blue color | | | 3 drop | | | | |
| Yellow color | | | | 3 drop | | | |

[1]Mixture of microcrystalline cellulose and sodium carboxymethylcellulose, available from FMC Biopolymer
[2]Available from Lilly ICOS, LLC, as Cialis ®
[3]Available from Pfizer, Inc. as Viagra ®
[4]Available as Imodium
[5]N-2,3-trimethyl-2-isopropyl butanamide
[6]N-Ethyl-p-menthane-3-carboxamide

TABLE 31

| | Weight (in g, unless otherwise indicated) | | | | | | |
|---|---|---|---|---|---|---|---|
| Component | FE | FF | FG | FH | FI | FJ | FK |
| HPC | 1.28 | 3.05 | 4.5 | 3.29 | 2.6 | 2.92 | 3.29 |
| PEO | 2.66 | 6.33 | 3 | 6.83 | 5.4 | 6.08 | 6.83 |
| Sucralose | 0.31 | 0.9 | 0.6 | | 0.64 | | |
| Magna Sweet | | 0.09 | | | | | |
| Avicel CL 611[1] | | 0.56 | 0.45 | | | | |
| Precipitated calcium carbonate | 1.07 | 2.02 | 0.99 | 6.05 | 0.90 | 2.67 | 1.39 |
| Meloxicam[2] | 1.97 | | | | | | |
| Risperidone[3] | | 0.62 | | | | | |
| Zyrtec ®[4] | | | 3.75 | | | | |
| Five Grass Powder[5] | | | | 2.207 | | | |
| Tea Tree Oil[6] | | | | | 4 | | |
| Antibacterial concentrate[7] | | | | | | 6.12 | |
| Mite extract[8] | | | | | | | 6.87 |
| Prosweet | | 0.66 | | | | | |
| Taste Masking Flavor | | 1.41 | | | | | |
| Peppermint Bittermask flavor | | 2.81 | | | 2.24 | | |
| Orange flavor | 0.47 | | | | | | |
| Strawberry & cream flavor | | | 1.5 | | | | |
| WS-3[9] | 0.020 | 0.081 | 0.038 | | 0.04 | | |
| Tween 80 | 0.012 | 0.028 | 0.022 | | 0.024 | 0.027 | |
| Simethicone | 0.08 | 0.19 | 0.15 | 0.37 | 0.16 | 0.18 | 0.37 |
| Water | 14.63 | 31.25 | 25 | 31.25 | 24 | 22 | 31.25 |
| Red color | 2 drop | | 5 drop | | | | |
| Blue color | | 3 drop | | | 3 drop | | |
| Yellow color | 3 drop | | | | | | |

[1]Mixture of microcrystalline cellulose and sodium carboxymethylcellulose, available from FMC Biopolymer
[2]Available as Mobic ®
[3]Available as Risperdal ®
[4]Available from Pfizer, Inc.
[5]Allergy treatment
[6]Antibiotic
[7]MegaBac ™, available from Nicrosol Technologies
[8]Allergy treatment
[9]N-Ethyl-p-menthane-3-carboxamide The above components were combined by mixing until a uniform mixture was achieved, and then cast into films on release paper using a K-Control Coater with a 250 or 350 micron smooth bar. The films were dried for about 9 to 10 minutes at 80° C. in accordance with the method of the present invention resulting in dried films having adequate to good strength.

While there have been described what are presently believed to be the preferred embodiments of the invention, those skilled in the art will realize that changes and modifications may be made thereto without departing from the spirit of the invention, and it is intended to include all such changes and modifications as fall within the true scope of the invention.

What is claimed is:

1. A process for manufacturing a resulting pharmaceutical film suitable for commercialization and regulatory approval said resulting pharmaceutical film having a substantially uniform distribution of a desired amount of a pharmaceutical active in individual doses of the resulting pharmaceutical film, comprising the steps of:

(a) forming a Non-Newtonian visco-elastic polymer matrix, comprising a polymer selected from the group consisting of hydroxyethylcellulose, hydroxypropylcellulose, polyacrylic acid, sodium carboxymethyl cellulose, ethylcellulose, polyacrylates, cellulosic polymers, carboxymethyl cellulose, polyethylene oxide and combinations thereof; a solvent selected from the group consisting of water, a polar organic solvent and combinations thereof, and the active selected from the group of opiates and opiate-derivatives and combinations thereof, which polymer matrix is a shear-thinning pseudoplastic fluid when exposed to shear rates of $10\text{-}10^5$ $sec^{-1}$, said polymer matrix having a substantially uniform distribution of said pharmaceutical active;

(b) casting said polymer matrix;

(c) conveying said polymer matrix through a drying apparatus and evaporating at least a portion of said solvent to rapidly form a visco-elastic film having said pharmaceutical active uniformly distributed throughout by rapidly increasing the viscosity of said polymer matrix upon initiation of drying within about the first 4 minutes to maintain said substantially uniform distribution of said pharmaceutical active by locking-in or substantially preventing migration of said pharmaceutical active; wherein the temperature of the polymer matrix is 100° C. or less;

(d) forming the resulting pharmaceutical film from said visco-elastic film, wherein the resulting pharmaceutical film having said substantially uniform distribution of pharmaceutical active by said locking-in or substantially preventing migration of said pharmaceutical active is maintained;

(e) sampling the resulting pharmaceutical film at different locations of the resulting pharmaceutical film, wherein said sampled resulting pharmaceutical film has a water content of 10% or less; and (f) performing analytical chemical tests for content uniformity of said pharmaceutical active in substantially equal sized individual dosage units of said sampled resulting pharmaceutical film said tests indicating that uniformity of content in the amount of the active varies by no more than 10% from the desired amount of the active.

2. The process of claim 1, wherein step (d) forming the resulting pharmaceutical film further comprises controlling drying through a process comprising drying at a temperature differential ranging from 5° C. to 30° C. between polymer matrix inside temperature and outside exposure temperature to minimize degradation wherein the water content of said resulting film is 10% or less.

3. The process of claim 1, wherein said drying apparatus uses air currents, which have forces below a yield value of the polymer matrix during drying.

4. A process for manufacturing a resulting multi-layer pharmaceutical film suitable for commercialization and regulatory approval, said resulting multi-layer pharmaceutical film having a substantially uniform distribution of pharmaceutical active, comprising the steps of:

(a) forming a Non-Newtonian visco-elastic polymer matrix, comprising a polymer selected from the group consisting of hydroxyethylcellulose, hydroxypropylcellulose, polyacrylic acid, sodium carboxymethyl cellulose, ethylcellulose, polyacrylates, cellulosic polymers, carboxymethyl cellulose, polyethylene oxide and combinations thereof; a solvent selected from the group consisting of water, and a polar organic solvent and combinations thereof, which polymer matrix is a shear-thinning pseudoplastic fluid when exposed to shear rates of $10\text{-}10^5$ $sec^{-1}$, said polymer matrix having a substantially uniform distribution of said pharmaceutical active;

(b) casting said polymer matrix;

(c) conveying said polymer matrix through a drying apparatus and evaporating at least a portion of said solvent to rapidly form a visco-elastic film within about the first 4 minutes, wherein the temperature of the polymer matrix is 100° C. or less;

(d) depositing a layer comprising a pharmaceutical active selected from the group consisting of opiates and opiate-derivatives and combinations thereof onto said visco-elastic film to form the resulting multi-layer pharmaceutical film;

(e) sampling said resulting pharmaceutical film at different locations of said resulting multi-layer pharmaceutical film, wherein said sampled resulting multi-layer pharmaceutical film has a water content of 10% or less; and (f) performing analytical chemical tests for content uniformity of said pharmaceutical active in substantially equal sized individual dosage units of said sampled resulting multi-layer pharmaceutical film, said tests indicating that the uniformity of content in the amount of the pharmaceutical active varies by no more than 10%.

5. A process for manufacturing a resulting pharmaceutical film suitable for commercialization and regulatory approval said resulting pharmaceutical film having a substantially uniform distribution of a desired amount of a pharmaceutical active in individual doses of the resulting pharmaceutical film, comprising the steps of:

(a) forming a Non-Newtonian visco-elastic polymer matrix by mixing, said matrix comprising a polymer selected from the group consisting of water-soluble polymers, water-swellable polymers and combinations thereof, a solvent selected from the group consisting of water, a polar organic solvent and combinations thereof, and a pharmaceutical active, which polymer matrix is a shear-thinning pseudoplastic fluid when exposed to shear rates of $10\text{-}10^5$ $sec^{-1}$; said polymer matrix having a substantially uniform distribution of said pharmaceutical active;

(b) casting said polymer matrix;

(c) conveying said polymer matrix through a drying apparatus and evaporating at least a portion of said solvent to rapidly form a pharmaceutical film having said pharmaceutical active substantially uniformly distributed throughout, by rapidly increasing the viscosity of said polymer matrix upon initiation of drying within about the first 4 minutes to maintain said substantially uniform distribution of said pharmaceutical active by locking-in or substantially preventing migration of said pharmaceutical active, wherein content uniformity of said pharmaceutical active in substantially equal sized individual dosage units of said pharmaceutical film is such that the amount of pharmaceutical active varies by no more than 10% of the desired amount;

(e) sampling the resulting pharmaceutical film at different locations of the resulting pharmaceutical film, wherein said sampled resulting pharmaceutical film has a water content of 10% or less and a thickness of from about 0.1 mils to about 10 mils; and (f) performing analytical chemical tests for content uniformity of said pharmaceutical active in substantially equal sized individual dosage units of said sampled resulting pharmaceutical film, said tests indicating said substantially uniform distribution of the pharmaceutical active, in that the amount of the pharmaceutical active varies by no more than 10% of the desired amount.

6. The process of claim 5, wherein said polymer comprises a polymer selected from the group consisting of cellulose, a cellulose derivative, pullulan, polyvinyl pyrrolidone, polyvinyl alcohol, polyethylene glycol, carboxyvinyl copolymers, hydroxypropylmethyl cellulose, hydroxyethyl cellulose, hydroxypropyl cellulose, carboxymethyl cellulose, sodium alginate, xanthan gum, tragacanth gum, guar gum, acacia gum, arabic gum, polyacrylic acid, methylmethacrylate copolymer, carboxyvinyl copolymers, starch, gelatin, and combinations thereof, alone or in combination with polyethylene oxide.

7. The process of claim 5, wherein the pharmaceutical active is selected from the group consisting of ace-inhibitors, anti-anginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, antilipid agents, anti-manics, anti-nauseants, anti-stroke agents, anti-thyroid preparations, anti-tumor drugs, anti-viral agents, acne drugs, alkaloids, amino acid preparations, anti-tussives, antiuricemic drugs, anti-viral drugs, anabolic preparations, systemic and non-systemic anti-infective agents, anti-neoplastics, anti-parkinsonian agents, anti-rheumatic agents, appetite stimulants, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-coagulants, anti-thrombotic drugs, hypnotics, anti-emetics, anti-nauseants, neuromuscular drugs, hyper- and hypo-glycemic agents, thyroid and anti-thyroid preparations, diuretics, anti-spasmodics, uterine relaxants, anti-obesity drugs, erythropoietic drugs, cough suppressants, mucolytics, DNA and genetic modifying drugs, and combinations thereof.

8. The process of claim 5, wherein said pharmaceutical active is selected from the group consisting of antigens, allergens, spores, microorganisms, seeds, enzymes, vitamins, bioactive active, amino acid preparations, sildenafils, tadalafils, vardenafils, apomorphines, yohimbine hydrochlorides, alprostadils, anti-diabetic agents, non-steroidal anti-inflammatory agents, biological response modifiers, anti-Alzheimer's agents, anesthetic agents, analgesic agents and combinations thereof.

9. The process of claim 5, wherein the pharmaceutical active is a protein or a glycoprotein.

10. The process of claim 5, wherein the pharmaceutical active is insulin.

11. The process of claim 5, wherein said resulting pharmaceutical film provides administration of said active to an individual through the buccal cavity of said individual.

12. The process of claim 5, wherein said resulting pharmaceutical film provides administration of said active to an individual through gingival application of said resulting pharmaceutical film.

13. The process of claim 5, wherein said pharmaceutical active is a hormone.

14. The process of claim 5, wherein said pharmaceutical active is an opiate or opiate-derivative.

15. The process of claim 5, wherein said pharmaceutical active is taste-masked.

16. The process of claim 5, wherein said pharmaceutical active is coated with a controlled release composition and said controlled release composition provides at least one of the following: an immediate release, a delayed release, a sustained release or a sequential release.

17. The process of claim 5, further comprising a step of providing a second film layer.

18. The process of claim 17, wherein said second film layer is coated onto said resulting pharmaceutical film.

19. The process of claim 17, wherein said resulting pharmaceutical film provides administration of said active to an individual through sublingual application of said resulting pharmaceutical film.

20. The process of claim 17, wherein said second film layer is cast onto said resulting pharmaceutical film.

21. The process of claim 17, wherein said second film layer is extruded onto said resulting pharmaceutical film.

22. The process of claim 17, wherein said second film layer is sprayed onto said resulting pharmaceutical film.

23. The process of claim 17, wherein said second film layer is laminated onto said resulting pharmaceutical film.

24. The process of claim 17, wherein said resulting pharmaceutical film is laminated onto said second film layer.

25. The process of claim 17, wherein said second film layer comprises an active.

26. The process of claim 17, wherein said active in said second film layer is different from said pharmaceutical active in said resulting pharmaceutical film.

27. The process of claim 5, wherein said resulting pharmaceutical film provides administration of said active to an individual through a mucosal membrane of said individual.

28. The process of claim 5, wherein said resulting pharmaceutical film provides administration of said active to an individual by administration within the body of the individual during surgery.

29. The process of claim 5, wherein said pharmaceutical active is in the form of a particle.

30. The process of claim 5, wherein said matrix comprises a dispersion.

* * * * *